United States Patent
Ding et al.

(10) Patent No.: US 7,449,582 B2
(45) Date of Patent: Nov. 11, 2008

(54) COMPOUNDS AND COMPOSITIONS AS PROTEIN KINASE INHIBITORS

(75) Inventors: Qiang Ding, San Diego, CA (US); Yongping Xie, San Diego, CA (US); Nathanael S. Gray, San Diego, CA (US); Shuli You, San Diego, CA (US); Greg Chopiuk, San Diego, CA (US); Jiqing Jiang, San Diego, CA (US); Yi Liu, San Diego, CA (US); Ruo Steensma, La Jolla, CA (US); Xing Wang, San Diego, CA (US); Taebo Sim, San Diego, CA (US)

(73) Assignee: IRM LLC, Hamilton (BM)

( * ) Notice: Subject to any disclaimer, the term of this patent is extended or adjusted under 35 U.S.C. 154(b) by 474 days.

(21) Appl. No.: 10/961,646

(22) Filed: Oct. 8, 2004

(65) Prior Publication Data

US 2005/0187230 A1    Aug. 25, 2005

Related U.S. Application Data

(60) Provisional application No. 60/509,572, filed on Oct. 8, 2003.

(51) Int. Cl.
  *C07D 215/38*    (2006.01)
  *C07D 471/02*    (2006.01)
  *C07D 251/38*    (2006.01)
(52) U.S. Cl. .................. 546/153; 546/157; 546/123; 544/224; 514/264.1; 514/299
(58) Field of Classification Search .............. 546/153, 546/157, 123; 544/224; 514/264.1, 299
See application file for complete search history.

(56) References Cited

U.S. PATENT DOCUMENTS

| 6,506,749 B2 * | 1/2003 | Chen et al. ............... 514/234.2 |
| 6,518,276 B2 * | 2/2003 | Arzeno et al. ............ 514/264.11 |
| 6,753,427 B2 * | 6/2004 | Arzeno et al. ............... 544/279 |
| 6,849,409 B2 * | 2/2005 | Schubart et al. ............... 435/6 |
| 6,861,423 B2 * | 3/2005 | Chen et al. ............... 514/234.2 |

FOREIGN PATENT DOCUMENTS

WO    WO 2002/28853 A1    4/2002

OTHER PUBLICATIONS

Clozel et al., Pharmacology of the Urotensin-II Receptor Antagonist Palosuran (ACT-058362; 1-[2-(4-Benzyl-4-hydroxy-piperidin-1-yl)-ethyl]-3-(2-methyl-quinolin-4-yl)-urea Sulfate Salt): First Demonstration of a Pathophysiological Role of the Eurotensin System, The Journal of Pharmacology and Experimental Therapeutics, 2004, pp. 204-212, The American Society for Pharmacology and Experimental Therapeutics.

* cited by examiner

*Primary Examiner*—D. Margaret Seaman
(74) *Attorney, Agent, or Firm*—Scott W. Reid; Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, CSK, JNK1, JNK2, PDGF-R, p38, p70S6K, TGFβ, SRC, EGFR, c-Kit, trkB, FGFR3, Fes, Lck, Syk, RAF, MKK4, MKK6 and SAPK2β kinases.

5 Claims, No Drawings

COMPOUNDS AND COMPOSITIONS AS PROTEIN KINASE INHIBITORS

CROSS-REFERENCE TO RELATED APPLICATIONS

This application claims the benefit of priority to U.S. Provisional Patent Application 60/509,572 filed 8 Oct. 2003. The full disclosure of this application is incorporated herein by reference in its entirety and for all purposes.

FIELD OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, CSK, JNK1, JNK2, PDGF-R, Bmx, p70S6K, TGFβ, SRC, trkB, FGFR3, Fes, Lck, RAF, MKK4, MKK6 and SAPK2α, SAPK2β kinases.

BACKGROUND

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the receptor kinase for stem cell factor, c-kit, the nerve growth factor receptor, trkB, and the fibroblast growth factor receptor, FGFR3; non-receptor tyrosine kinases such Abl and the fusion kinase BCR-Abl, Fes, Lck and Syk; and serine/threonine kinases such as b-RAF, MAP kinases (e.g., MKK6) and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

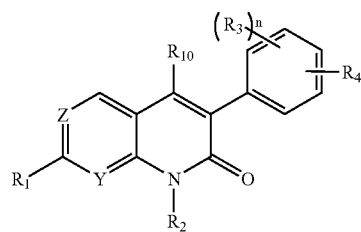

(I)

in which:
n is 0, 1 or 2;
Y is selected from —C(H)= and —N=;
Z is selected from —C(H)= and —N=;
$R_1$ is selected from hydrogen, halo and —$R_4$;
$R_2$ is selected from hydrogen and $C_{1-6}$alkyl;
$R_3$ is selected from halo, nitro, $C_{1-6}$alkyl and $C_{1-6}$alkoxy;
$R_4$ is selected from $C_{3-8}$heterocycloalkyl, —$XNR_5R_6$, —$XNR_5C(O)R_6$, —$XC(O)NR_5R_6$ and —$XNR_5S(O)_{0-2}R_6$; wherein X is a bond or $C_{1-4}$alkylene; $R_5$ is selected from hydrogen and $C_{1-6}$alkyl; $R_6$ is selected from $C_{1-6}$alkyl, $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any aryl, heteroaryl, cycloalkyl and heterocycloalkyl of $R_6$ is optionally substituted by 1 to 3 radicals independently selected from halo, hydroxy, nitro, cyano, $C_{1-6}$alkyl optionally substituted with hydroxy, $C_{1-6}$alkoxy, halo-substituted-$C_{1-6}$alkyl, halo-substituted-$C_{1-6}$alkoxy, —$XOXNR_7R_8$, —$XS(O)_{0-2}R_7$, —$XS(O)_{0-2}NR_7R_8$, —$XOR_7$, —$XC(O)NR_7R_8$, —$XNR_7R_8$, —$XNR_7S(O)_{0-2}R_7$ and —$XR_9$; wherein X is a bond or $C_{1-4}$alkylene; $R_7$ and $R_8$ are independently selected from hydrogen and $C_{1-6}$alkyl; $R_9$ is selected from $C_{6-10}$aryl, $C_{5-10}$heteroaryl $C_{3-12}$cycloalkyl and $C_{3-8}$heterocycloalkyl; wherein any aryl, heteroaryl, cycloalkyl or heterocycloalkyl of $R_9$ is optionally substituted with 1 to 3 $C_{1-6}$alkyl radicals;
$R_{10}$ is selected from hydrogen, halo and $C_{1-6}$alkyl; and the N-oxide derivatives, prodrug derivatives, protected derivatives, individual isomers and mixture of isomers thereof, and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly Abl, BCR-Abl, CSK, JNK1, JNK2, PDGF-R, p38, p70S6K, TGFβ, SRC, EGFR, c-Kit, trkB, FGFR3, Fes, Lck, Syk, RAF, MKK4, MKK6 and/or SAPK2β activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly Abl, BCR-Abl, CSK, JNK1, JNK2, PDGF-R, p38, p70S6K, TGFβ, SRC, EGFR, c-Kit, trkB, FGFR3, Fes, Lck, Syk, RAF, MKK4, MKK6 and/or SAPK2β activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl.

"Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3] dioxole, imidazolyl, benzoimidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Treat", "treating" and "treatment" refer to a method of alleviating or abating a disease and/or its attendant symptoms.

Description of the Preferred Embodiments

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells. The present invention provides compounds, compositions and methods for the treatment of kinase related disease, particularly Abl, BCR-Abl, CSK, JNK1, JNK2, PDGF-R, p38, p70S6K, TGFβ, SRC, EGFR, c-Kit, trkB, FGFR3, Fes, Lck, Syk, RAF, MKK4, MKK6 and/or SAPK2β kinase related diseases. For example, leukemia and other proliferation disorders related to BCR-Abl can be treated through the inhibition of wild type and mutant forms of Bcr-Abl.

In one embodiment, with reference to compounds of Formula I, n is 0, 1 or 2;

Y is selected from —C(H)═ and —N═;
Z is selected from —C(H)═ and —N═;
$R_1$ is selected from hydrogen, halo and —$R_4$;
$R_2$ is selected from hydrogen and $C_{1-6}$alkyl;
$R_3$ is selected from halo, $C_{1-6}$alkyl and $C_{1-6}$alkoxy;
$R_4$ is selected from $C_{3-8}$heterocycloalkyl, —$XNR_5R_6$, —$XNR_5C(O)R_6$ and —$XNR_5S(O)_{0-2}R_6$; wherein X is a bond or $C_{1-4}$alkylene; $R_5$ is selected from hydrogen and $C_{1-6}$alkyl; $R_6$ is selected from $C_{1-6}$alkyl, $C_{6-10}$aryl-$C_{0-4}$alkyl, $C_{3-8}$heterocycloalkyl-$C_{0-4}$alkyl, $C_{5-10}$heteroaryl-$C_{0-4}$alkyl and $C_{3-12}$cycloalkyl-$C_{0-4}$alkyl; wherein any aryl, heteroaryl and cycloalkyl of $R_4$ is optionally substituted by 1 to 3 radicals independently selected from halo, hydroxy, nitro, $C_{1-6}$alkyl optionally substituted with hydroxy, $C_{1-6}$alkoxy, halo-substituted-$C_{1-6}$alkyl, halo-substituted-$C_{1-6}$alkoxy, —$XS(O)_{0-2}R_7$, —$XOXNR_7R_8$, —$XS(O)_{0-2}NR_7R_8$, —$XOR_7$, —$XC(O)NR_7R_8$, —$XNR_7R_8$ and —$XR_9$; wherein X is a bond or $C_{1-4}$alkylene; $R_7$ and $R_8$ are independently selected from hydrogen and $C_{1-6}$alkyl; $R_9$ is selected from $C_{5-10}$heteroaryl and $C_{3-8}$heterocycloalkyl; wherein any heteroaryl or heterocycloalkyl of $R_9$ is optionally substituted with 1 to 3 $C_{1-6}$alkyl radicals; and $R_{10}$ is hydrogen.

In another embodiment, $R_1$ is selected from hydrogen, halo, pyrrolidinyl and —$NHR_6$; wherein $R_6$ is selected from hydrogen, methyl, ethyl, diethyl-amino-propyl, morpholino-ethyl, hydroxy-ethyl, benzo[1,3]dioxolyl, pyrazolyl, pyridinyl, pyrazinyl, pyridinyl-methyl, 2-(2-oxo-pyrrolidin-1-yl)-ethyl and phenyl; wherein said pyrrolidinyl, pyridinyl, pyrazolyl, pyrazinyl, pyridinyl-methyl, 2-(2-oxo-pyrrolidin-1-yl)-ethyl or phenyl is optionally substituted by 1 to 2 radicals independently selected from amino, methoxy, dimethylamino, dimethylamino-methyl, dimethylamino-ethyl, dimethylamino-propyl, dimethylamino-ethoxy, methyl-sulfanyl, hydroxy, methylsulfonyl, hydroxymethyl, 1-hydroxy-ethyl, methane-sulfonyl-amino, morpholino, morpholino-ethyl, furanyl-methyl, 4-methyl-piperazin-1-yl, 4-methyl-piperazin-1-ylmethyl, benzyl, methyl-aminocarbonyl, methyl-carbonyl-amino, methyl-pyrazolyl, aminocarbonyl and amino-sulfonyl.

In a further embodiment, $R_4$ is selected from —NHC(O)R and —NHS(O)$_2R_6$; wherein & is selected from methyl, isobutyl, tert-butyl, cyclohexyl, furanyl, pyrrolyl, phenyl, pyridinyl, pyridazinyl, pyrazinyl, pyrazolyl, tetrazolyl-methyl and benzyl; wherein said cyclohexyl, furanyl, pyrrolyl, phenyl, pyridinyl, pyridazinyl, pyrazinyl, pyrazolyl, tetrazolyl-methyl or benzyl of $R_6$ is optionally substituted by 1 to 3 radicals selected from 4-methyl-piperazin-1-ylmethyl, 4-methyl-piperazin-1-yl, 4-ethyl-piperazin-1-ylmethyl, 4-ethyl-piperazin-1-yl, phenyl, ethyl, trifluoromethyl, morpholino, dimethylamino, halo, nitro, trifluoromethoxy, 1-methyl-pyrrol-2-yl, 4-methyl-imidazol-1-yl, 4-methyl-piperazin-1-yl, 4-methyl-piperazin-1-ylmethyl, isobutyl and tert-butyl.

Preferred compounds of Formula I are detailed in the Examples and Table I, infra.

Pharmacology and Utility

Compounds of the invention modulate the activity of protein tyrosine kinases and, as such, are useful for treating diseases or disorders in which protein tyrosine kinases, particularly Abl, BCR-Abl, CSK, JNK1, JNK2, PDGF-R, p38, p70S6K, TGFβ, SRC, EGFR, c-Kit, trkB, FGFR3, Fes, Lck, Syk, RAF, MKK4, MKK6 and/or SAPK2β kinases, contribute to the pathology and/or symptomology of the disease.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation. Compounds of the invention can inhibit the autophosphorylation of SCF receptors.

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

Syk is a tyrosine kinase that plays a critical role in mast cell degranulation and eosinophil activation. Accordingly, Syk kinase is implicated in various allergic disorders, in particular asthma. It has been shown that Syk binds to the phosphorylated gamma chain of the FcεR1 receptor via N-terminal SH2 domains and is essential for downstream signaling.

The Ras-Raf-MEK-ERK signaling pathway mediates cellular response to growth signals. Ras is mutated to an oncogenic form in ~15% of human cancer. The Raf family belongs to the serine/threonine protein kinase and it includes three members, A-Raf, B-Raf and c-Raf (or Raf-1). The focus on Raf being a drug target has centered on the relationship of Raf as a downstream effector of Ras. However, recent data suggests that B-Raf may have a prominent role in the formation of certain tumors with no requirement for an activated Ras allele (Nature 417, 949-954 (1 Jul. 2002). In particular, B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

Multiple forms of p38 MAPK ($\alpha, \beta, \gamma, \delta$), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNFα. P38 functions by phosphorylating downstream substrates that include other kinases and transcription factors. Agents that inhibit p38 kinase have been shown to block the production of cytokines including but not limited to TNFα, IL-6, IL-8 and IL-1β. Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS. P38 inhibitors are efficacious in animal models of inflammatory disease. The destructive effects of many disease states are caused by the over production of pro-inflammatory cytokines. The ability of p38 inhibitors to regulate this overproduction makes them useful as disease modifying agents.

Molecules that block p38's function have been shown to be effective in inhibiting bone resorption, inflammation, and other immune and inflammation-based pathologies. Thus, a safe and effective p38 inhibitor would provide a means to treat debilitating diseases that can be regulated by modulation of p38 signaling like, for example, RA. Therefore, compounds of the invention that inhibit p38 activity are useful for the treatment of inflammation, osteoarthritis, rheumatoid arthritis, cancer, autoimmune diseases, and for the treatment of other cytokine mediated diseases.

Transforming growth factor-beta (TGFβ) denotes a super-family of proteins that includes, for example, TGFβ1, TGFβ2, and TGFβ3, which are pleotropic modulators of cell growth and differentiation, embryonic and bone development, extracellular matrix formation, hematopoiesis, immune and inflammatory responses. The members of the TGFβ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication. Consequently, compounds of the invention that are inhibitors of the TGFβ intracellular signaling pathway are useful treatments for fibroproliferative diseases, including kidney disorders associated with unregulated TGFβ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGFβ activity include adult respiratory distress syndrome, COPD, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers.

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000 November; 267 (21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4):447-51) and cell growth (Prog. Nucleic Acid Res. Mol. Biol., 2000;65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Agents that inhibit SAPK activity in a cell prevent DNA repair and sensitize the cell to those cancer therapeutic modalities that act by inducing DNA damage.

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

Fes is strongly expressed in myeloid hematopoietic cells and is implicated in both differentiation and survival signaling pathways in myeloid leukocytes. CSK is implicated in cancers, particularly colorectal and breast cancers.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4lg. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In each of the three reaction schemes below, $R_{10}$ is shown as hydrogen. Compounds of Formula I, in which $R_2$ is hydrogen, can be prepared by proceeding as in the following Reaction Scheme I:

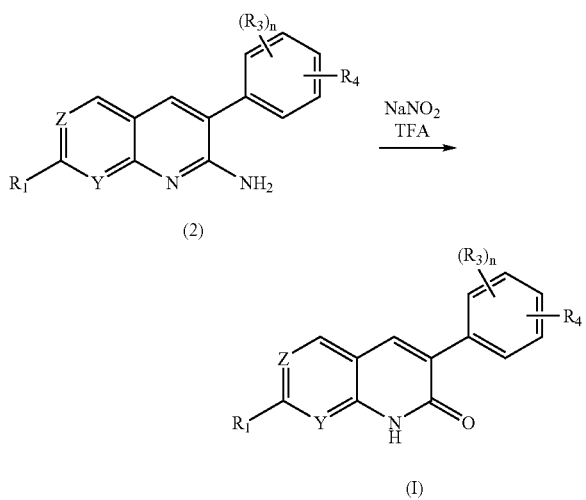

in which $R_1$, $R_3$, $R_4$, Y, Z and n are as defined for Formula I in the Summary of the Invention. A compound of Formula I can be prepared by reacting a compound of formula 2 with a suitable oxidizing agent (e.g., $NaNO_2$, and the like) in the presence of a suitable acid (e.g., TFA, and the like). The reaction is carried out at 20 to 40° C. and can take up to 4 hours to complete.

Compounds of Formula I, in which $R_2$ is $C_{1-6}$alkyl, can be prepared by proceeding as in the following Reaction Scheme II:

Reaction Scheme II

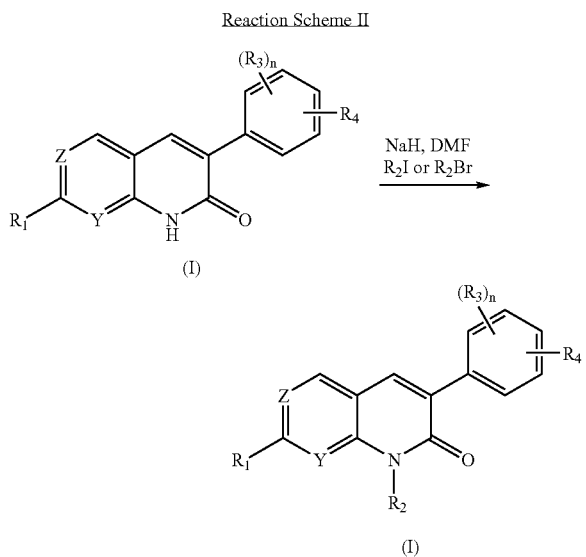

in which $R_1$, $R_3$, $R_4$, Y, Z and n are as defined for Formula I in the Summary of the Invention.

A compound of Formula I can be prepared by reacting a compound of Formula I, in which $R_2$ is hydrogen, with $R_2I$ or $R_2Br$ in the presence of a suitable solvent (e.g., DMF, and the like) and a suitable oxidizing agent (e.g., NaH, and the like). The reaction is carried out at 0 to 25° C. and can take up to 4 hours to complete.

Reaction Scheme III

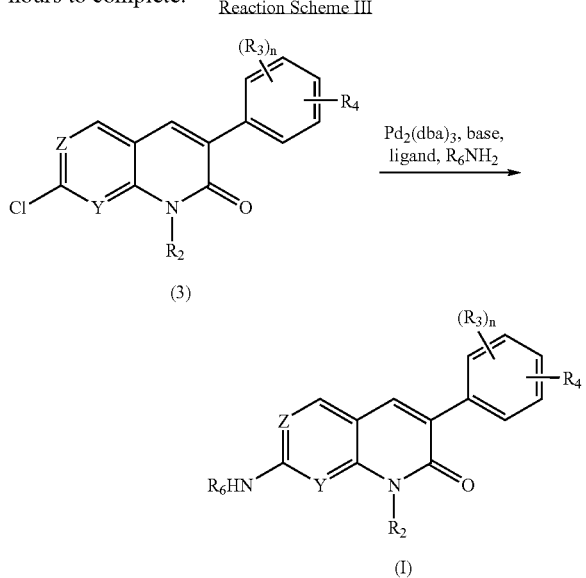

in which $R_2$, $R_3$, $R_4$, $R_6$, Y, Z and n are as defined for Formula I in the Summary of the Invention.

A compound of Formula I can be prepared by reacting a compound of Formula I with $R_6NH_2$ in the presence of a suitable solvent (e.g., dioxane, and the like), a suitable base (e.g., potassium phosphate, potassium tert-butanoxide, and the like), a suitable ligand (e.g., Xantphos, imidazolium ligand (see Example 8), and the like) and a suitable catalyst (e.g., $Pd_2(dba)_3$, $Pd(OAc)_2$ and the like). The reaction is carried out at about 80 to about 120° C. and can take up to 24 hours to complete.

Detailed descriptions of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I, II or III; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I (Examples) and intermediates (References) according to the invention.

Example 1

N-[2,4-dichloro-3-(1-methyl-2-oxo-1,2-dihydro-[1,6]naphthyridin-3-yl)-phenyl]-4-(4-methyl-piperazin-1-ylmethyl)-benzamide

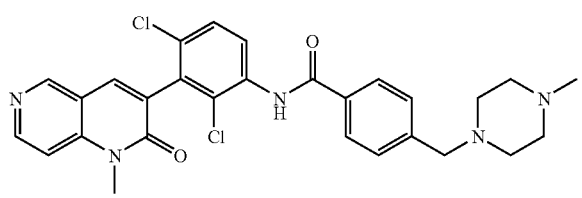

Step A: Preparation of 2,6-dichloro-3-nitrophenyl-acetonitrile

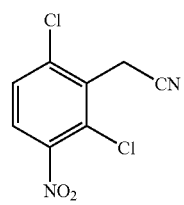

To a solution of 2,6-dichloro-phenyl-acetonitrile (15.0 g, 80.62 mmol) in the dichloromethane (50 mL) and $H_2SO_4$ (40 mL) is added (slowly) a mixture of $H_2SO_4$ (14 mL) and $HNO_3$ (5.5 mL) at 0° C. The reaction mixture is stirred at 0° C. for 20 minutes, warmed to room temperature for half hour, and then concentrated to remove organic solvent. The solution is poured into a beaker containing ice-water (400 mL) to give a crystalline precipitate, which is collected by vacuum filtration and washed with water to afford the product (20.44 g, 82.4%).

Step B: Preparation of 3-(2,6-dichloro-3-nitro-phenyl)-[1,6]naphthyridin-2-ylamine

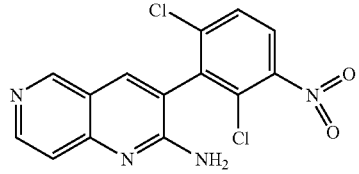

A solution of 2,6-dichloro-3-nitrophenyl-acetonitrile (1.02 g, 4.42 mmol), 4-amino-pyridine-3-carbaldehyde (0.4 g, 3.28 mmol) and NaOH (52 mg, 1.31 mmol) in EtOH (2.0 mL) is heated to 105° C. for 24 hours. The reaction mixture is diluted with EtOAc (50 ml) and washed with saturated $K_2CO_3$ and brine. The organic layer is dried, filtered and concentrated to give crude product. Flash silica gel column purification eluting with $CH_2Cl_2$ (100%) gradient to $CH_2Cl_2$/MeOH (2N $NH_3$) (100/6) affords the titled intermediate as a solid (257 mg, 23.4%).

Step C: Preparation of 3-(2,6-dichloro-3-nitro-phenyl)-1H-[1,6]naphthyridin-2-one

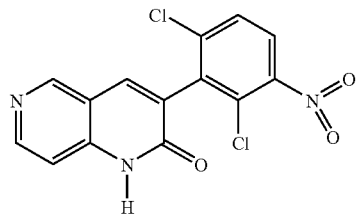

To a solution of 3-(2,6-dichloro-3-nitro-phenyl)-[1,6]naphthyridin-2-ylamine (50 mg, 0.149 mmol) in TFA (3.0 mL) is slowly added $NaNO_2$ at 0° C. The reaction mixture is stirred at 0° C. for 15 minutes, warmed to room temperature and stirred for three hours. The solution is poured into a beaker containing ice-water (50 mL) and NaCO3, then extracted with EtOAc (3×50 ml) and washed with saturated $K_2CO_3$ and brine. The organic layer is dried, filtered and concentrated to give the title intermediate as a solid (50 mg, 100%).

Alternative method to preparation of 3-(2,6-dichloro-3-nitro-phenyl)-1H-[1,6]naphthyridin-2-one:

Step A': Preparation of (2,6-dichloro-3-nitro-phenyl)-acetic acid

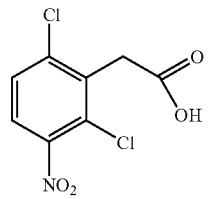

A solution of 2,6-dichloro-3-nitrophenyl-acetonitrile (15.0 g, 64.94 mmol) in water (100 mL) and $H_2SO_4$ (con. 100 mL) is heated to 120° C. for three hours. The reaction mixture is cooled to room temperature and is poured into a beaker containing ice-water (250 mL) to give a crystalline precipitate, which is collected by vacuum filtration and washed with water to afford the product (16.0 g, 98.6%).

Step B': Preparation of 2-(2,6-dichloro-3-nitro-phenyl)-N-(3-formyl-pyridin-4-yl)-acetamide

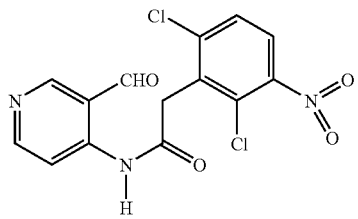

A solution of (2,6-dichloro-3-nitro-phenyl)-acetic acid (15.0 g, 60.0 mmol) in thionyl chloride (60 mL) is refluxed for one hour. The solvent is removed by concentration; dry toluene is added and concentrated to thoroughly remove thionyl chloride. To the solution of acid chloride in dry dichloromethane (200 mL) is added (drop-wise) a solution of 4-amino-pyridine-3-carbaldehyde (6.6 g, 54 mmol) in dichloromethane (50 mL) and DIEDA (10.7 mL, 60 mmol). The mixture is at room temperature for 2 hours. The reaction mixture is diluted with EtOAc (300 ml) and washed with saturated $K_2CO_3$ and brine. The organic layer is dried, filtered and concentrated to give crude product. Recrystallization with dichloromethane/hexane results in the titled compound as a solid (18.2 g, 95.2%).

Step C': Preparation of 3-(2,6-dichloro-3-nitro-phenyl)-1H-[1,6]naphthyridin-2-one A solution of 2-(2,6-dichloro-3-nitro-phenyl)-N-(3-formyl-pyridin-4-yl)-acetamide (5.0 g, 14.12 mmol) and $Na_2CO_3$ (2.5 g) in MeOH (300 mL) is heated for 15 minutes at 70° C. After filtration of the reaction mixture, the solvent is removed by concentration to give crude product, which is purified by flash silica gel column elute with $CH_2Cl_2$ (100%) gradient to $CH_2Cl_2$/MeOH (2N $NH_3$) (93/7%) to give the titled intermediate as a solid (3.75 g, 77.7%).

Step D: Preparation of 3-(2,6-dichloro-3-nitro-phenyl)-1-methyl-1H-[1,6]naphthyridin-2-one

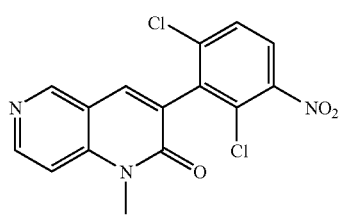

To a solution of 3-(2,6-dichloro-3-nitro-phenyl)-1H-[1,6]naphthyridin-2-one (2.0 g, 5.95 mmol) in DMF (50 mL) is added HNa (286 mg, 60%, 7.14 mmol) and IMe (0.5 mL, 8.03 mmol) at 0° C. The mixture is stirred for two hours at 0° C., diluted with EtOAc (300 ml) and washed with saturated $K_2CO_3$, brine and water. The organic layer is dried, filtered and concentrated to give crude product, which is purified by flash silica gel column elute with $CH_2Cl_2$ (100%) gradient to $CH_2Cl_2$/MeOH (2N $NH_3$)(98.5/1.5) to give the titled intermediate as a solid (1.67 g, 80.3%).

Step E: Preparation of 3-(3-amino-2,6-dichloro-phenyl)-1-methyl-1H-[1,6]naphthyridin-2-one

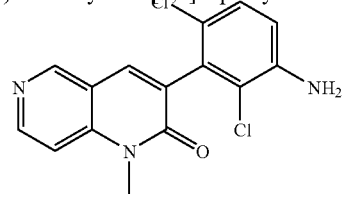

To a suspended solution of 3-(2,6-dichloro-3-nitro-phenyl)-1-methyl-1H-[1,6]naphthyridin-2-one (1.55 g, 4.427 mmol) in EtOH (12 mL) is added a solution of $Sn(II)Cl_2$ (3.80 g, 19.92 mmol) in HCl (con. 16 mL) at 75° C. After stirring for 30 minutes at 75° C., the mixture is diluted with EtOAc and neutralized with $K_2CO_3$ to a pH of 8. The organic layer is washed with saturated $K_2CO_3$, brine and dried, filtered and concentrated to give crude product. The crude product is purified by recrystallization with $CH_2Cl_2$/EtOAc/Hexane to give the titled intermediate as a solid (1.32 g, 93.15%).

Step F: Preparation of 4-chloromethyl-N-[2,4-dichloro-3-(1-methyl-2-oxo-1,2-dihydro-[1,6]naphthyridin-3-yl)-phenyl]-benzamide

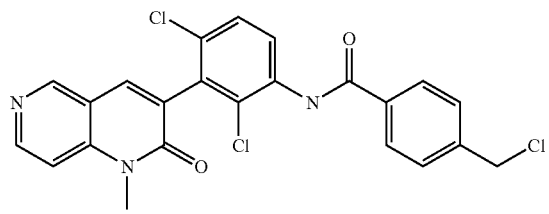

To a solution of 3-(3-amino-2,6-dichloro-phenyl)-1-methyl-1H-[1,6]-naphthyridin-2-one (30 mg, 0.0937 mmol) in the dichloromethane (7 mL) is added 4-(chloromethyl)benzoyl chloride (53.2 mg, 0.28 mmol). After the mixture is stirred 24 hours at room temperature, it is diluted with EtOAc and washed with saturated $K_2CO_3$, brine and water. The organic layer is dried, filtered and concentrated to give crude product, which is purified by flash silica gel column elute with $CH_2Cl_2$ (100%) gradient to $CH_2Cl_2$/MeOH ($NH_3$, 2N)(95/5%) to give the titled intermediate as a solid (32.4 mg, 73.1%).

Step G: Preparation of N-[2,4-dichloro-3-(1-methyl-2-oxo-1,2-dihydro-[1,6]naphthyridin-3-yl)-phenyl]-4-(4-methyl-piperazin-1-ylmethyl)-benzamide

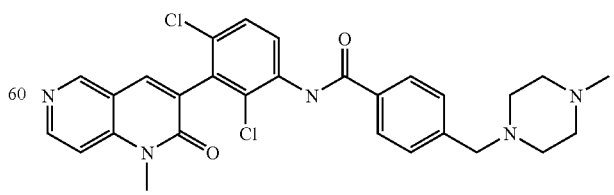

To a solution of 4-chloromethyl-N-[2,4-dichloro-3-(1-methyl-2-oxo-1,2-dihydro-[1,6]naphthyridin-3-yl)-phenyl]- benzamide (25 mg, 0.0529 mmol) in DMF (2.5 mL) is added CsCO₃ (51.7 mg, 0.1587 mmol) and (53.2 mg, 0.28 mmol). After the mixture is stirred for 30 minutes at room temperature, it is diluted with EtOAc and washed with saturated K₂CO₃ and brine. The organic layer is dried, filtered and concentrated to give crude product, which is purified by flash silica gel column eluting with CH₂Cl₂ (100%) gradient to CH₂Cl₂/MeOH(NH₃, 2N) (98/8) to give N-[2,4-dichloro-3-(1-methyl-2-oxo-1,2-dihydro-[1,6]naphthyridin-3-yl)-phenyl]-4-(4-methyl-piperazin-1-ylmethyl)-benzamide as a solid (21 mg, 73.9%): $^1$H NMR 400 MHz (CDCl₃) δ 8.86 (s, 1H), 8.69 (s, 1H), 8.63 (d, 1H), 8.44 (s, 1H), 7.84-7.86 (m, 2H), 7.77 (s, 1H), 7.46-7.52 (m, 3H), 7.29 (d, 1H), 3.78 (s, 3H), 3.58 (s, 2H), 2.50 (m, 8H), 2.30 (s, 3H); MS m/z 537.2 (M+1).

Example 2

N-[2,4-dichloro-3-(1-methyl-2-oxo-1,2-dihydro-[1,6]naphthyridin-3-yl-phenyl]-3-trifluoromethyl-benzenesulfonamide

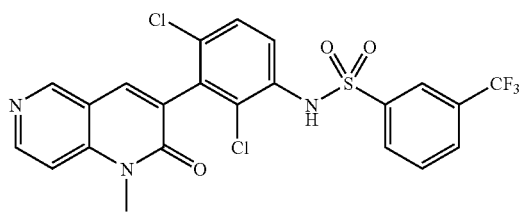

3-(3-Amino-2,6-dichloro-phenyl)-1-methyl-1H-[1,6]naphthyridin-2-one (35 mg, 0.1093 mmol) is dissolved in dry THF (2 mL). 4-trifluoromethylbenzenesulfonyl chloride (26.74 mg, 0.1093 mmol) and pyridine (12.95 mg, 0.1640 mmol) are added. The reaction is refluxed for 2 hours, diluted with ethyl acetate (150 mL) and washed with saturated K₂CO₃ and brine. The organic phase is dried using MgSO₄ and the crude product is purified by column chromatography on silica gel column and eluted with a 0-4% methanol/methylene chloride gradient to give N-[2,4-Dichloro-3-(1-methyl-2-oxo-1,2-dihydro-[1,6]naphthyridin-3-yl-phenyl]-3-trifluoromethyl-benzenesulfonamide as a white solid (20.6 mg): $^1$H NMR (CD₃OD): δ3.70 (s, 3H), 7.44 (d, 1H), 7.53 (d, 1H), 7.63 (t, 1h), 7.82 (m, 3H), 7.91 (s, 1H), 7.98 (s, 1H), 8.62 (d, 1H), 9.03 (s, 1H); MS m/z 528 (M+1).

Example 3

N-[2,4-Dichloro-3-(1-methyl-2-oxo-1,2-dihydro-quinolin-3-yl)-phenyl]-3-trifluoromethyl-benzamide

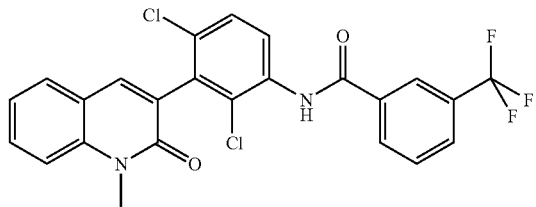

Step A: Preparation of 2-(2,6-dichloro-3-nitro-phenyl)-N-(2-formyl-phenyl)-acetamide

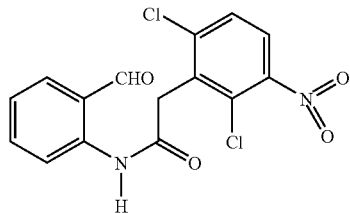

A solution of (2,6-dichloro-3-nitro-phenyl)-acetic acid (0.90 g, 3.35 mmol) in thionyl chloride (15 mL) is refluxed for one hour. The solvent is removed by concentration and dry toluene is added to thoroughly remove thionyl chloride. To the solution of acid chloride in dry dichloromethane (30 mL) is added (drop-wise) a solution of 2-aminobenzaldehyde (0.365 g, 3.02 mmol) in dichloromethane (5.0 mL). The mixture is stirred at room temperature for 2 hours. The reaction mixture is diluted with EtOAc and washed with saturated K₂CO₃ and brine. The organic layer is dried, filtered and concentrated to give crude product (0.94 g, 88.6%).

Step B: Preparation of 3-(2,6-dichloro-3-nitro-phenyl)-1H-quinolin-2-one

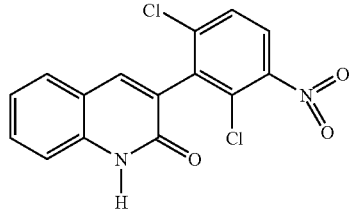

A solution of 2-(2,6-dichloro-3-nitro-phenyl)-N-(2-formyl-phenyl)-acetamide (0.7 g, 1.99 mmol) and Na₂CO₃ (1.0 g) in MeOH (150 mL) is heated for 30 minutes at 70° C. After filtration of the reaction mixture, the solvent is removed by concentration to give crude product. The crude product is purified by flash silica gel column, eluting with CH₂Cl₂ (100%) gradient to CH₂Cl₂/MeOH (2N NH₃) (97/3%), resulting in the titled intermediate as a solid (0.288 g, 41.3%).

Step C: Preparation of 3-(2,6-dichloro-3-nitro-phenyl)-1-methyl-1H-quinolin-2-one

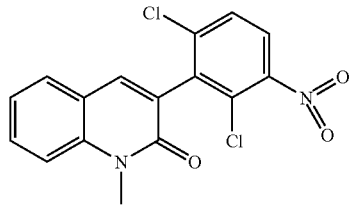

To a solution of 3-(2,6-dichloro-3-nitro-phenyl)-1H-quinolin-2-one (0.21 g, 0.6266 mmol) in DMF (5.0 mL) is added HNa (30.1 mg, 60%, 0.752 mmol) and IMe (120.1 mg, 0.846 mmol) at 0° C. After the mixture is stirred for two hours at 0° C., the mixture is diluted with EtOAc and washed with saturated K$_2$CO$_3$, brine and water. The organic layer is dried, filtered and concentrated to give crude product, which is purified by flash silica gel column, eluting with CH$_2$Cl$_2$ (100%) gradient to CH$_2$Cl$_2$/MeOH (2N NH$_3$) (95/5), t give the titled intermediate as a solid (78 mg, 35.8%).

Step D: Preparation of 3-(3-amino-2,6-dichloro-phenyl)-1-methyl-1H-quinolin-2-one

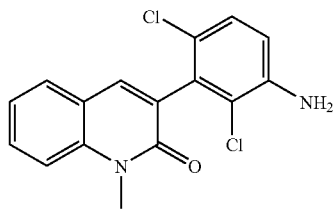

To a suspended solution of 3-(2,6-dichloro-3-nitro-phenyl)-1-methyl-1H-quinolin-2-one (50 mg, 0.143 mmol) in EtOH (3.0 mL) is added a solution of Sn(II)Cl$_2$ (122 mg, 0.644 mmol) in concentrated HCl (2.0 mL) at 75° C. After the mixture is stirred for 30 minutes at 75° C., the mixture is diluted with EtOAc and neutralized with K$_2$CO$_3$ until a pH of 8 is achieved. The organic layer is washed with saturated K$_2$CO$_3$, brine and dried, filtered and concentrated to give crude product (44.2 mg, 96.7%).

Step E: Preparation of N-[2,4-dichloro-3-(1-methyl-2-oxo-1,2-dihydro-quinolin-3-yl)-phenyl]-3-trifluoromethyl-benzamide

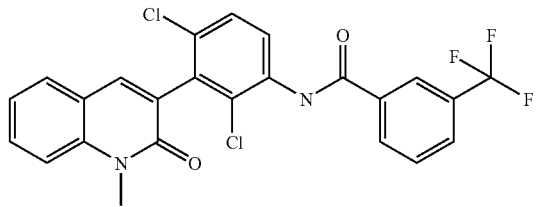

To a solution of 3-(3-amino-2,6-dichloro-phenyl)-1-methyl-1H-quinolin-2-one (30 mg, 0.094 mmol) in the dichloromethane (5.0 mL) is added 4-(chloromethyl)benzoyl chloride (58.7 mg, 0.283 mmol). After the mixture is stirred for 24 hours at room temperature, it is diluted with EtOAc and washed with saturated K$_2$CO$_3$, brine and water. The organic layer is dried, filtered and concentrated to give crude product, which is purified by flash silica gel column elute with CH$_2$Cl$_2$ (100%) gradient to CH$_2$Cl$_2$/MeOH(NH$_3$, 2N)(95/5) to give N-[2,4-dichloro-3-(1-methyl-2-oxo-1,2-dihydro-quinolin-3-yl)-phenyl]-3-trifluoromethyl-benzamide as a solid (34.5 mg, 75.0%): $^1$H NMR 400 MHz (CDCl$_3$) δ 8.53 (d, 1H), 8.47 (s, 1H), 8.20 (s, 1H), 8.05 (d, 1H), 7.84 (d, 1H), 7.72 (s, 1H), 7.61-7.69 (m, 3H), 7.51 (d, 1H), 7.46 (d, 1H), 7.30 (m, 1H), 3.83 (s, 3H); MS m/z 491.20 (M+1).

Example 4

N-[3,5-Dichloro-4-(1-methyl-2-oxo-1,2-dihydro-[16] naphthyridin-3-yl-phenyl]-3-trifluoromethyl-benzamide

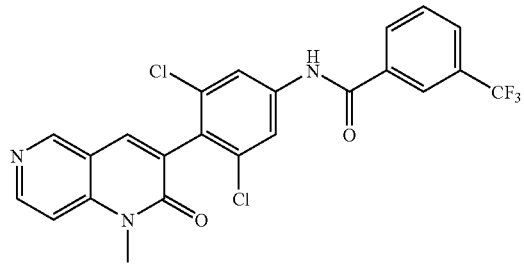

To a solution of 3,5-dichloronitrobenzene (50.00 g, 260.6 mmol) and methyl thioacetonitrile (22.71 g, 260.6 mmol) in DMSO (400 mL) is added NaOH (20.84 g, 521.2 mmol) at 0° C. The reaction mixture is warmed to room temperature, with stirring for 24 hours, at room temperature under N$_2$. The reaction is diluted with ice water and acidified by 3N HCl to a pH of 1. The mixture is extracted by ethyl acetate (3×500 mL), washed by H$_2$O, dried by MgSO$_4$ and concentrated to get a black oil. The oil is purified by column chromatography on silica gel column, eluting with a 0-10% ethyl acetate/hexanes gradient, to give 2,6-dichloro-4-nitrobenzylnitrile as a yellow solid (11.00 g).

A stirred suspension of 2,6-dichloro-4-nitrobenzylnitrile (10.86 g, 47.0 mmol) in concentrated H$_2$SO$_4$ (45 mL) and H$_2$O (50 mL) is heated for 2.5 hours at 150° C. The reaction mixture is then poured into water (300 mL). The precipitate is collected by filtration to give 2,6-dichloro-4-nitrobenzyl-carboxylic acid as a white solid (10.41 g).

2,6-Dichloro-4-nitrobenzyl-carboxylic acid (3.00 g, 11.98 mmol) is suspended in thionyl chloride (12 mL). The suspension is heated to 80° C. and refluxed for 30 minutes. Excess thionyl chloride is evaporated completely by adding dry toluene. The residue is dissolved in dry methylene chloride (50 mL) and then added to a solution of 4-amino-3-pyridylcarboxyaldehyde (1.76 g, 14.38 mmol) in dry methylene chloride (5 mL) and triethylamine (2.91 g, 28.76 mmol). After stirring for 2 hours at room temperature, the reaction mixture is diluted by ethyl acetate (500 mL), washed with saturated K$_2$CO$_3$ solution and brine. The organic phase is dried by MgSO$_4$ and the crude product is purified by column chromatography on silica gel column, eluting with a 0-4% methanol/methylene chloride gradient, to give 2-(2,6-dichloro-4-nitrophenyl)-N-(3-formyl-pyridin-4-yl)-acetamide a white solid (3.00 g).

2-(2,6-Dichloro-4-nitro-phenyl)-N-(3-formyl-pyridin-4-yl)-acetamide (3.0 g, 8.47 mmol) is dissolved in dry methanol (240 mL). Na$_2$CO$_3$ (1.80 g, 16.94 mmol) is added. The reaction is refluxed for 30 minutes, diluted by ethyl acetate (210 mL) and filtered. The solvents are evaporated to give crude product, which is recrystallized by ethyl acetate/hexanes to give 3-(2,6-dichloro-4-nitro-phenyl)-1H-[1,6]-naphthyridin-2-one as a slightly yellow solid (3.07 g).

3-(2,6-Dichloro-4-nitro-phenyl)-1H-[1,6]-naphthyridin-2-one (1.50 g, 4.46 mmol) is dissolved in dry DMF (60 mL) and cooled to 0° C. NaH (0.20 g, 60% in mineral oil, 4.91 mmol) and iodomethane (0.76 g, 5.35 mmol) are added with stirring for 1.5 hours at 0° C. The solvent is removed by evaporation, the residue dissolved in ethyl acetate (300 mL), washed with saturated K₂CO₃ and brine, dried with MgSO₄ and concentrated to get crude product (1.30 g), which was used in the next step directly without further purification.

The crude of the last step (437 mg) is suspended in anhydrous ethanol (45 mL). SnCl₂ (946 mg, 4.99 mmol) dissolved in concentrated HCl (6 mL) is added into the suspension. The reaction is heated to 75° C. and refluxed for 30 minutes. The reaction is diluted by ethyl acetate (200 mL) and washed with saturated K₂CO₃ and brine. The organic phase is dried by MgSO₄ and the crude product is purified by column chromatography on silica gel column, eluting with a 0-4% 2.0N ammonia methanol solution/methylene chloride gradient, to give 3-(4-amino-2,6-dichloro-phenyl)-1-methyl-1H-[1,6] naphthyridin-2-one as a yellow solid (265 mg).

To a solution 3-(4-amino-2,6-dichloro-phenyl)-1-methyl-1H-[1,6]naphthyridin-2-one (30 mg, 0.0937 mmol) in dry methylene chloride (12 mL) is added 3-trifluoromethylbenzoyl chloride (39.08 mg, 0.1874 mmol). The reaction is kept stirring for 2 hours at room temperature. The reaction is diluted by ethyl acetate (100 mL), and washed with saturated K₂CO₃ and brine. The organic phase is dried by MgSO₄ and the crude product purified by column chromatography on silica gel column, eluting with a 0-4% methanol/methylene chloride gradient, to give N-[3,5-dichloro-4-(1-methyl-2-oxo-1,2-dihydro-[1,6]naphthyridin-3-yl-phenyl]-3-trifluoromethyl-benzamide as a white solid (42 mg). ¹H NMR 400 MHz (CD₃OD): δ3.80 (s, 3H), 7.62 (d, 1H), 7.76 (t, 1H), 7.92 (d, 1H), 8.01 (s, 2H), 8.06 (s, 1H), 8.23 (d, 1H), 8.30 (s, 1H), 8.64 (d, 1H), 8.92 (s, 1H). MS m/z 492.2 (M+1).

Example 5

N-[4-chloro-3-(2-oxo-1,2-dihydro-[1,6]naphthyridin-3-yl)-phenyl]-3-trifluoromethyl-benzamide

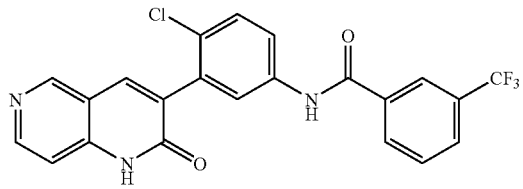

To a solution of 2-chloro-5-nitro-phenylacetic acid (3.08 g, 14.28 mmol) in dichloromethane (150 mL) is added oxalyl chloride (6.2 mL, 71.00 mmol) and the mixture is refluxed for 1 hour. After cooling to room temperature, it is concentrated and the residue is co-evaporated with anhydrous toluene (2×30 mL). This residue is then dissolved in dichloromethane (60 mL) and a solution of 4-amino-pyridine-3-carbaldehyde (1.744 g, 14.28 mmol) in dichloromethane (30 mL) is added. This mixture is stirred for 20 minutes before N,N'-diisopropylethylamine (2.56 mL, 14.28 mmol) is added. The stirring is continued for another two hours before diluting with dichloromethane (500 mL). The mixture is washed with water (100 mL), brine (100 mL), dried over MgSO₄, filtered and concentrated. This crude product is used without further purification.

The above crude product and sodium carbonate (3.0 g, 28.3 mmol) in methanol (50 mL) are refluxed for 30 minutes. The solid is removed by filtration and the filtrate concentrated. The residue is dissolved in EtOAc (500 mL), washed with water (2×50 mL), the organic phase is separated and concentrated. The final product is obtained after crystallization (2.78 g).

3-(2-Chloro-5-nitro-phenyl)-1H-[1,6]-naphthyridin-2-one (0.96 g, 3.18 mmol) is suspended in ethanol (15 mL). SnCl₂ (2.71 g, 14.3 mmol) and HCl (20 mL) is added and the mixture is refluxed for two hours before cooling to room temperature. EtOAc (100 mL) is added and the mixture is neutralized by the addition of sodium carbonate. Extracted with EtOAc (3×100 mL), the combined organics are washed with brine (50 mL), dried over MgSO₄, to obtain the final product as a light yellow solid (0.62 g, 71.7%).

To a solution of 3-(5-amino-2-chloro-phenyl)-1H-[1,6]-naphthyridin-2-one (60 mg, 0.23 mmol) and DIPEA (82 µl, 0.46 mmol) in anhydrous THF (2.5 mL), is added a solution of 3-trifluoromethyl-benzoyl chloride (44 µl). This mixture is stirred for 30 minutes at room temperature, diluted with EtOAc (50 mL), washed with water (10 mL) and brine (10 mL), dried over MgSO₄, concentrated and purified by preparative HPLC, to give N-[4-chloro-3-(2-oxo-1,2-dihydro-[1,6]naphthyridin-3-yl)-phenyl]-3-trifluoromethyl-benzamide (18.3 mg).

Example 6

N-(2,4-Dichloro-3-{2-[3-(1-hydroxy-ethyl)-phenylamino]-8-methyl-7-oxo-7,8-dihydro-pyrido[2,3-d] pyrimidin-6-yl}-phenyl)-3-trifluoromethyl-benzamide

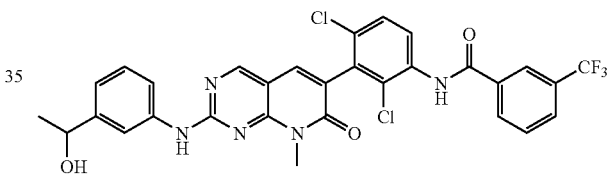

Step A: Preparation of 4-Amino-2-methylsulfanyl-pyrimidine-5-carbaldehyde

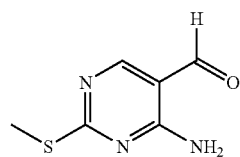

To a solution of 4-amino-2-(methylthio)pyrimidine-5-carbonitrile (3.0 g, 18.05 mmol) in THF (100 mL) is added diisobutylaluminum hydride (41.52 mL, 1.0 M in CH₂Cl₂, 41.52 mmol) at 0° C. After the mixture is stirred for 2.5 hours at 0° C., hydrochloric acid (2N, 30 mL) is added and stirring is continued for 20 minutes. To the reaction mixture is added saturated Na₂CO₃ until a pH of 8 is achieved. The suspended material is filtered through Celit pad and washed with K₂CO₃ solution. The solution is diluted with EtOAc and washed with saturated K₂CO₃, brine and dried, filtered and concentrated to give crude product, which is purified by flash silica gel column, eluting with hexane (100%) gradient to hexane/ether (60/40%), to give the title intermediate as a solid (1.62 g, 53.1%).

Step B: Preparation of 6-(3-Amino-2,6-dichloro-phenyl)-2-methylsulfanyl-pyrido[2,3-d]pyrimidin-7-ylamine

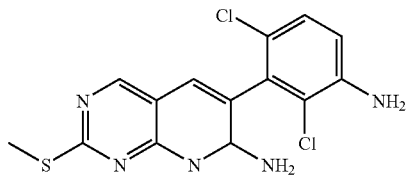

A mixture of 4-amino-2-methylsulfanyl-pyrimidine-5-carbaldehyde (2.0 g, 11.82 mmol), (3-amino-2,6-dichloro-phenyl)-acetonitrile (2.85 g, 14.18 mmol) and $K_2CO_3$ (4.9 g, 35.49 mmol) in DMF (20 mL) is heated to 110° C. for 30 hours. The solution is cooled to room temperature and the solid is removed by filter paper and concentrated to give crude product. Flash silica gel column purification, eluting with $CH_2Cl_2$ (100%) gradient to $CH_2Cl_2$/MeOH (2N $NH_3$) (100/7%), gives the title intermediate as a solid (3.31 g, 80.0%).

Step C: Preparation of N-[3-(7-Amino-2-methylsulfanyl-pyrido[2,3-d]pyrimidin-6-yl)-2,4-dichloro-phenyl]-3-trifluoromethyl-benzamide

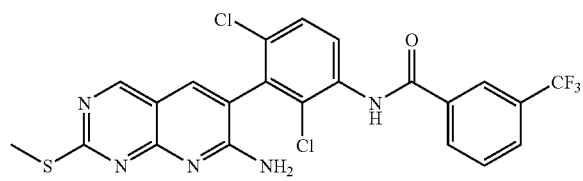

To a solution of 6-(3-amino-2,6-dichloro-phenyl)-2-methylsulfanyl-pyrido[2,3-d]-pyrimidin-7-ylamine (0.5 g, 1.42 mmol) in $CH_2Cl_2$ (40 mL) is added 3-(trifluoromethyl)benzoyl chloride (1.07 mL, 7.1 mmol). After the mixture is stirred for 24 hours at room temperature, the mixture is diluted with EtOAc and washed with saturated $K_2CO_3$, brine and water. The organic layer is dried, filtered and concentrated to give crude product, which is purified by a flash silica gel column, eluting with $CH_2Cl_2$ (100%) gradient to $CH_2Cl_2$/MeOH ($NH_3$, 2N)(95/5%), to give the title intermediate as a solid (0.591 g, 79.4 %).

Step D: Preparation of N-[2,4-Dichloro-3-(2-methylsulfanyl-7-oxo-7,8-dihydro-pyrido[2,3-d]pyrimidin-6-yl)-phenyl]-3-trifluoromethyl-benzamide

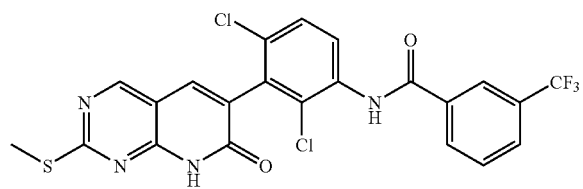

To a solution of N-[3-(7-amino-2-methylsulfanyl-pyrido[2,3-d]pyrimidin-6-yl)-2,4-dichloro-phenyl]-3-trifluoromethyl-benzamide (1.7 g, 3.24 mmol) in TFA (15 mL) is slowly added $NaNO_2$ (783 mg, 11.35 mmol) at 0° C. with stirring for 20 minutes. The solvents are evaporated and diluted with EtOAc and washed with saturated $K_2CO_3$, brine and water. The organic layer is dried, filtered and concentrated to give the crude product. The crude product is purified by flash silica gel column, eluting with $CH_2Cl_2$ (100%) gradient to $CH_2Cl_2$/MeOH($NH_3$, 2N)(93/7%), to give the title intermediate as a solid (1.64 g, 96.5%).

Step E: Preparation of N-[2,4-Dichloro-3-(8-methyl-2-methylsulfanyl-7-oxo-7,8-dihydro-pyrido[2,3-d]pyrimidin-6-yl)-phenyl]-3-trifluoromethyl-benzamide

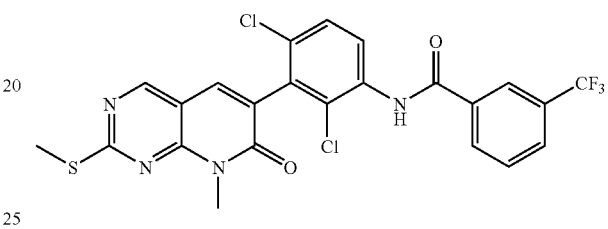

To a solution of N-[2,4-dichloro-3-(2-methylsulfanyl-7-oxo-7,8-dihydro-pyrido[2,3-d]pyrimidin-6-yl)-phenyl]-3-trifluoromethyl-benzamide (1.14 g, 2.17 mmol) in DMF (35 mL) is slowly added NaH (117.2 mg, 60%, 2.93 mmol) with stirring for 30 minutes a 0° C. Iodomethane (369 mg, 2.60 mmol) is added to above solution with stirring for 40 minutes at 0° C. The solvents are evaporated and diluted with EtOAc and washed with saturated $K_2CO_3$, brine and water. The organic layer is dried, filtered and concentrated to give crude product, which is purified by flash silica gel column, eluting with $CH_2Cl_2$ (100%) gradient to $CH_2Cl_2$/MeOH($NH_3$, 2N) (93/7), to give the title intermediate as a solid (1.14 g, 98.0%).

Step F: Preparation of N-[2,4-Dichloro-3-(2-methanesulfonyl-8-methyl-7-oxo-7,8-dihydro-pyrido[2,3-d]pyrimidin-6-yl)-phenyl]-3-trifluoromethyl-benzamide

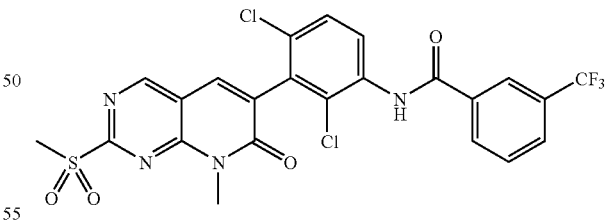

A solution of N-[2,4-dichloro-3-(8-methyl-2-methylsulfanyl-7-oxo-7,8-dihydro-pyrido[2,3-d]pyrimidin-6-yl)-phenyl]-3-trifluoromethyl-benzamide (1.1 g, 2.04 mmol) and MCPBA (983 mg, 60%, 4.38 mmol) in $CH_2Cl_2$ (50 mL) is stirred for one hour at room temperature. The mixture is diluted with EtOAc and washed with saturated $K_2CO_3$, brine and water. The organic layer is dried, filtered and concentrated to give crude product, which is purified by a flash silica gel column, eluting with hexane (100%) gradient to hexane/EtOAc (65/35), to give the title intermediate as a solid (472 mg, 40.7%).

Step G: Preparation of N-(2,4-Dichloro-3-{2-[3-(1-hydroxy-ethyl)-phenylamino]-8-methyl-7-oxo-7,8-dihydro-pyrido[2,3-d]pyrimidin-6-yl}-phenyl)-3-trifluoromethyl-benzamide

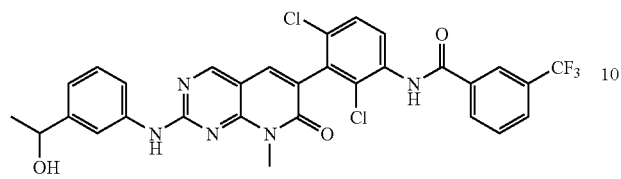

A mixture of N-[2,4-dichloro-3-(2-methanesulfonyl-8-methyl-7-oxo-7,8-dihydro-pyrido[2,3-d]pyrimidin-6-yl)-phenyl]-3-trifluoromethyl-benzamide (20 mg, 0.035 mmol) and 3-(1-hydroxyethyl)-aniline (50 mg, 0.364 mmol) is heated at 120° C. for ten minutes. The mixture is diluted with EtOAc and washed with saturated K$_2$CO$_3$, brine and water. The organic layer is dried, filtered and concentrated to give crude product, which is purified by prep-HPLC to give N-(2,4-dichloro-3-{2-[3-(1-hydroxy-ethyl)-phenylamino]-8-methyl-7-oxo-7,8-dihydro-pyrido[2,3-d]pyrimidin-6-yl}-phenyl)-3-trifluoromethyl-benzamide as a white solid. (17.9 mg, 81.4%). $^1$H NMR (CD$_3$OD): δ 10.50 (s, 1H), 8.57 (d, 1H), 8.52 (s, 1H), 8.41 (s, 1H), 8.19 (s, 1H), 8.06 (d, 1H), 7.92 (s, 1H), 7.86 (d, 1H), 7.68 (t, 1H), 7.59 (d, 1H), 7.56 (s, 1H), 7.52 (d, 1H), 7.41 (t, 1H), 7.21 (s, 1H), 7.20 (d, 1H), 4.98 (q, 1H), 3.83 (s, 3H), 1.54 (d, 2H); MS m/z 629.10 (M+1).

Example 7

N-{3-[2-(3-Amino-phenylamino)-8-methyl-7-oxo-7,8-dihydro-pyrido[2,3-d]pyrimidin-6-yl]-4-chloro-phenyl}-3-trifluoromethyl-benzamide

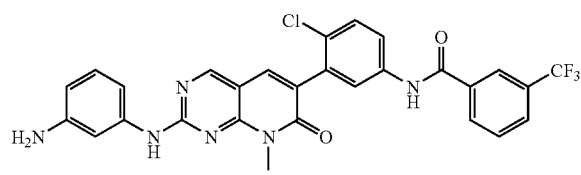

Step A: Preparation of (2-Chloro-5-nitro-phenyl)-acetonitrile

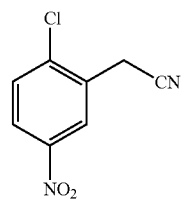

To a solution of 2-chloro-phenyl-acetonitrile (15.0 g, 99.0 mmol) in the dichloromethane (50 mL) and H$_2$SO$_4$ (40 mL) is slowly added a mixture of H$_2$SO$_4$ (14 mL) and HNO$_3$ (5.5 mL) at 0° C. The reaction mixture is stirred at 0° C. for 20 minutes, warmed to room temperature for 30 minutes and then concentrated to remove organic solvent. The solution is poured into a beaker containing ice-water (400 mL) to give a crystalline precipitate, which is collected by vacuum filtration and washed with water to give the title intermediate (13.4 g, 69.0%).

Step B: Preparation of (5-Amino-2-chloro-phenyl)-acetonitrile

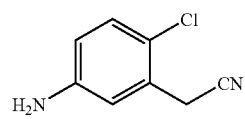

To a suspended solution of (2-Chloro-5-nitro-phenyl)-acetonitrile (4.0 g, 20.0 mmol) in EtOH (10 mL) is added a solution of Sn(II)Cl$_2$ (15.36 g, 81.0 mmol) in concentrated HCl (14 mL) at 75° C. After the mixture is stirred for 30 minutes at 75° C., the mixture is diluted with EtOAc and neutralized with K$_2$CO$_3$ until a pH of 8 is achieved. The organic layer is washed with saturated K$_2$CO$_3$, brine and dried, filtered and concentrated to give crude product, which is purified by recrystallization with CH$_2$Cl$_2$/EtOAc/Hexane to give the title intermediate as a solid (3.04 g, 89.7%).

Step C: Preparation of 6-(5-amino-2-chloro-phenyl)-2-methylsulfanylpyrido[2,3d]pyrimidin-7-ylamine

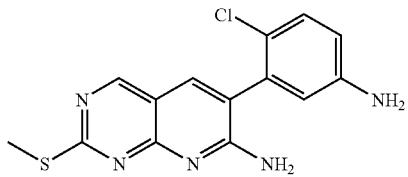

A solution of 4-amino-2-methylsulfanyl-pyrimidine-5-carbaldehyde (1.8 g, 10.64 mmol), (5-Amino-2-chloro-phenyl)-acetonitrile (2.3 g, 13.83 mmol) and K$_2$CO$_3$ (4.41 g, 31.92 mmol) in DMF (20 mL) is heated to 110° C. for 36 hours. The solution is cooled to room temperature and the solid is removed by filter paper. Then the mixture is concentrated to give crude product. Flash silica gel column purification elute with CH$_2$Cl$_2$ (100%) gradient to CH$_2$Cl$_2$/MeOH (2N NH$_3$) (97/3%) gives the title intermediate as a solid (1.24 g, 36.7%).

Step D: Preparation of N-[3-(7-Amino-2-methylsulfanyl-pyrido[2,3-d]pyrimidin-6-yl)-4-chloro-phenyl]-3-trifluoromethyl-benzamide

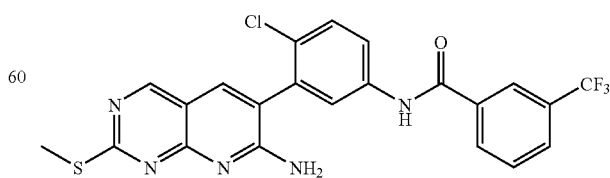

To a solution of 6-(5-amino-2-chloro-phenyl)-2-methylsulfanylpyrido[2,3d]-pyrimidin-7-ylamine (0.65 g, 2.046 mmol) in CH$_2$Cl$_2$ (80 mL) is added 3-(trifluoromethyl)benzoyl chloride (2.13 g, 10.23 mmol). After the mixture is stirred for 24 hours at room temperature, the mixture is diluted with EtOAc and washed with saturated K$_2$CO$_3$, brine and water. The organic layer is dried, filtered and concentrated to give crude product as a solid (1.0 g, ~100%).

Step E: Preparation of N-[4-chloro-3-(2-methylsulfanyl-7-oxo-7,8-dihydro-pyrido[2,3-d]pyrimidin-6-yl)-phenyl]-3-trifluoromethyl-benzamide

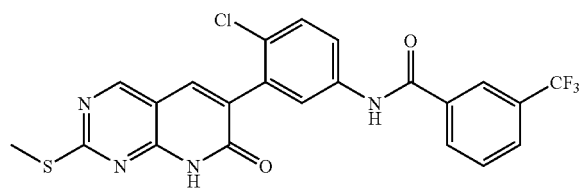

To a solution of N-[3-(7-amino-2-methylsulfanyl-pyrido[2,3-d]pyrimidin-6-yl)-4-chloro-phenyl]-3-trifluoromethyl-benzamide (1.0 g, 2.04 mmol) in TFA (10 mL) is slowly added NaNO$_2$ (423 mg, 6.12 mmol) at 0° C. with stirring for 20 minutes. The solvents are evaporated, diluted with EtOAc and washed with saturated K$_2$CO$_3$, brine and water. The organic layer is dried, filtered and concentrated to give crude product, which is purified by flash silica gel column, eluting with CH$_2$Cl$_2$ (100%) gradient to CH$_2$Cl$_2$/MeOH(NH$_3$, 2N) (93/7%), to give the title intermediate as a solid (0.644 g, 64.4%).

Step F: Preparation of N-[4-Dichloro-3-(8-methyl-2-methylsulfanyl-7-oxo-7,8-dihydro-pyrido[2,3-d]pyrimidin-6-yl)-phenyl]-3-trifluoromethyl-benzamide

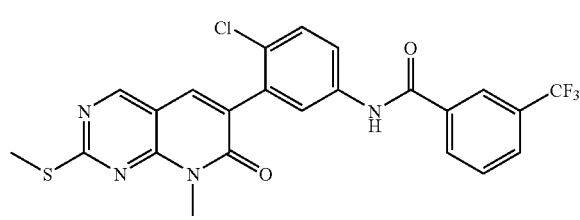

To a solution of N-[4-dichloro-3-(2-methylsulfanyl-7-oxo-7,8-dihydro-pyrido[2,3-d]pyrimidin-6-yl)-phenyl]-3-trifluoromethyl-benzamide (370 mg, 0.75 mmol) in DMF (35 mL) is slowly added NaH (40.7 mg, 60%, 1.02 mmol) with stirring for 30 minutes at 0° C. Iodomethane (133.7 mg, 0.94 mmol) is added to the above solution, stirring for 40 minutes at 0° C. The solvents are evaporated and diluted with EtOAc and washed with saturated K$_2$CO$_3$, brine and water. The organic layer is dried, filtered and concentrated to give crude product, which is used for the next reaction without further purification.

Step G: Preparation of N-[4-Dichloro-3-(2-methanesulfonyl-8-methyl-7-oxo-7,8-dihydro-pyrido[2,3-d]pyrimidin-6-yl)-phenyl]-3-trifluoromethyl-benzamide

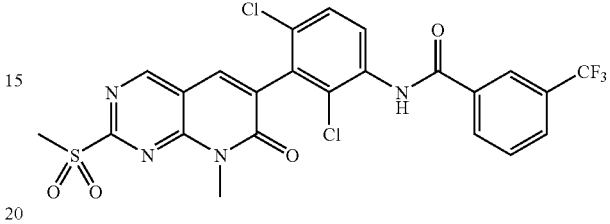

A solution of N-[4-dichloro-3-(8-methyl-2-methylsulfanyl-7-oxo-7,8-dihydro-pyrido[2,3-d]pyrimidin-6-yl)-phenyl]-3-trifluoromethyl-benzamide (380 mg, 0.75 mmol) and MCPBA (386 mg, 60%, 1.72 mmol) in CH$_2$Cl$_2$ (25 mL) is stirred for one hour at room temperature. The mixture is diluted with EtOAc and washed with saturated K$_2$CO$_3$, brine and water. The organic layer is dried, filtered and concentrated to give crude product, which is purified by a flash silica gel column, eluting with hexane (100%) gradient to hexane/EtOAc (65/35%), to give the title intermediate as a solid (126 mg, 31.1%).

Step H: Preparation of N-{3-[2-(3-Amino-phenylamino)-8-methyl-7-oxo-7,8-dihydro-pyrido[2,3-d]pyrimidin-6-yl]-4-chloro-phenyl}-3-trifluoromethyl-benzamide 3-Aminoaniline (121.1 mg, 1.12 mmonl) is heated to 110° C. When melted, N-[4-chloro-3-(2-methanesulfonyl-8-methyl-7-oxo-7,8-dihydro-pyrido[2,3-d]pyrimidin-6-yl)-phenyl]-3-trifluoromethyl-benzamide 34 (15 mg, 0.028 mmol) is added. The reaction is stirred at 110° C. for 25 minutes. The reaction is diluted with MeOH (1 mL) and purified by prep-HPLC to give the final product as a yellow solid: $^1$H NMR (CDCl$_3$): δ3.64 (s, 3H), 6.66 (d, 1H), 7.17 (t, 1H), 7.28 (d, 1H), 7.42 (m, 2H), 7.48 (t, 1H), 7.50 (dd, 1H), 7.57 (s, 1H), 7.63 (m, 2H), 7.97 (d, 1H), 8.07 (s, 1H), 8.49 (s, 1H); MS m/z 565.0 (M+1).

Example 8

N-{3-[7-(6-Methoxy-pyridin-3-ylamino-1-methyl-2-oxo-1,2-dihydro-[1,6]naphthyridin-3-yl]-4-methyl-phenyl}-3-trifluoromethyl-benzamide

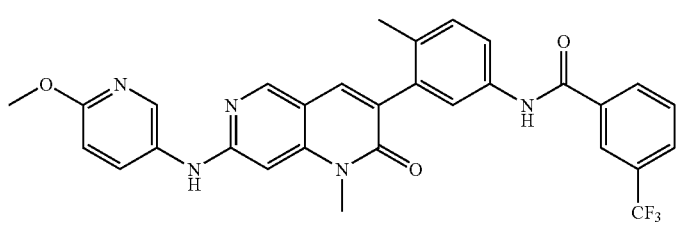

-continued
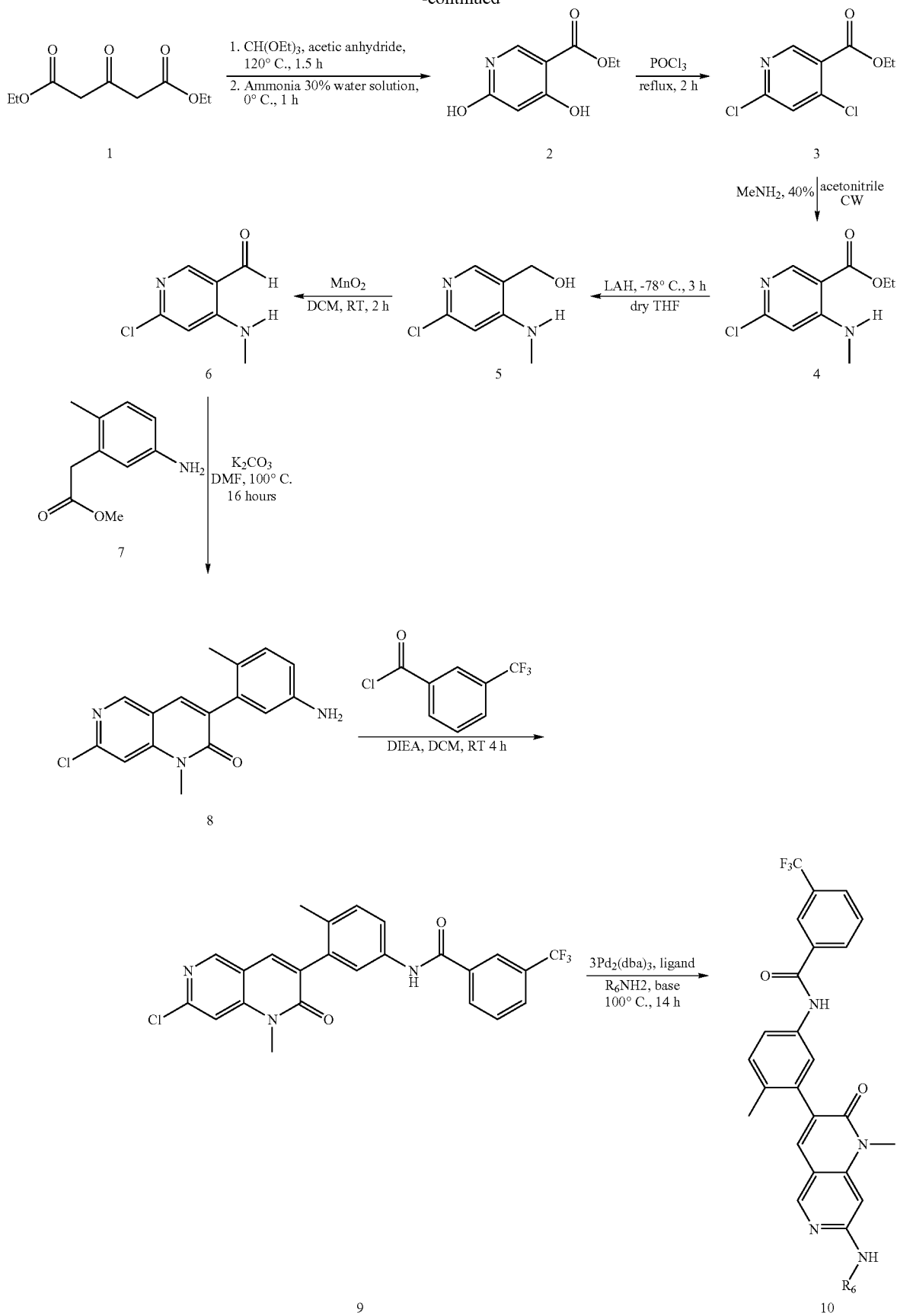

For the above reaction scheme, $R_6NH_2$ is 6-methoxy-pyridin-3-ylamine. Mix the diethyl 1,3-acetonedicarboxylate (10.11 g, 50 mmol) with triethyl orthoformate (8.14 g, 55 mmol) and acetic anhydride (10.20 g, 100 mmol) in a 100 mL flask and heat up to 120° C. for 1.5 hours. The crude product is distilled under vacuum (150-200 mmHg) around 90-100° C., the light yellow oil solution will be collected in the condenser. The left residue is cooled in ice and mixed with 30% ammonia (4 ml). The reaction is continued in ice bath for 1 hour and then acidified with 2N HCl to pH<5. Remove the solvent under the vacuum. The crude product is purified by flash chromatography using EA/Hexane(1:1). The final product compound (2) 4,6-dihydroxy-nicotinic acid ethyl ester is the clear oil, 2.85 g.

4,6-Dihydroxy-nicotinic acid ethyl ester (2.85 g) is mixed with pure POCl3 25 mL in a 100 mL flask and heated up to 110° C. for 2 hours. After cooling down, most of the POCl3 is removed under vacuum. The crude dark color product is pooled into small amount ice-water mixture, and neutralized with saturated sodium carbonate solution. Extracted the product by using 200 mL ethyl acetate for a couple of times. The combined organic layer is washed by saturated sodium chloride solution and dried by $Na_2SO_4$. After removing the solvent, the crude product is purified by flash chromatography using EA/Hexane (15%:85%). The final compound (3) 4,6-dichloro-nicotinic acid ethyl ester is white solid, 3.05 g.

4,6-Dichloro-nicotinic acid ethyl ester (2.19 g, 10 mmol) is dissolved in 30 mL acetonitrile and cooled down to 0° C., slowly add 4 mL methylamine solution (40% methylamine water solution, 50 mmol). The reaction is stirred at 0° C. for 30 minutes and warmed up to RT for another 2 hours. Remove the solvent under the vacuum and purify the crude product by flash chromatography using EA/Hexane (30%:70%). The final compound (4) 6-chloro-4-methylamino-nicotinic acid ethyl ester is white solid, 2.03 g.

6-chloro-4-methylamino-nicotinic acid ethyl ester (2.03 g, 9.5 mmol) is dissolved in 30 mL anhydrous THF and cooled down to −78° C. Add 20 mL LAH THF solution (1M THF solution, 20 mmol) slowly and continue the reaction for 3 hours at −78° C. Warm up the reaction to the RT slowly and check TLC to make sure no starting materials left. Add small amount MeOH/EA (1:1) mixture slowly to destroy the excess LAH. The crude product goes through a celite plug and is washed by EA for a couple of times. After removing the solvent under vacuum, the crude product is purified by flash chromatography using MeOH/DCM (5%:95%). The final compound (5) (6-chloro-4-methylamino-pyridin-3-yl)-methanol is white solid, 1.40 g.

(6-chloro-4-methylamino-pyridin-3-yl)-methanol (1.40 g, 8.1 mmol) is dissolved in 40 mL DCM and 7.0 g $MnO_2$ (81 mmol) is added. The reaction is stirred in RT for 2 hours. Then the reaction solution goes through a celite plug and washed by EA. After removing the solvent under the vacuum, the crude product is purified by flash chromatography using EA/Hexane (3:7). The final compound (6) 6-chloro-4-methylamino-pyridine-3-carbaldehyde is the white solid, 1.30 g.

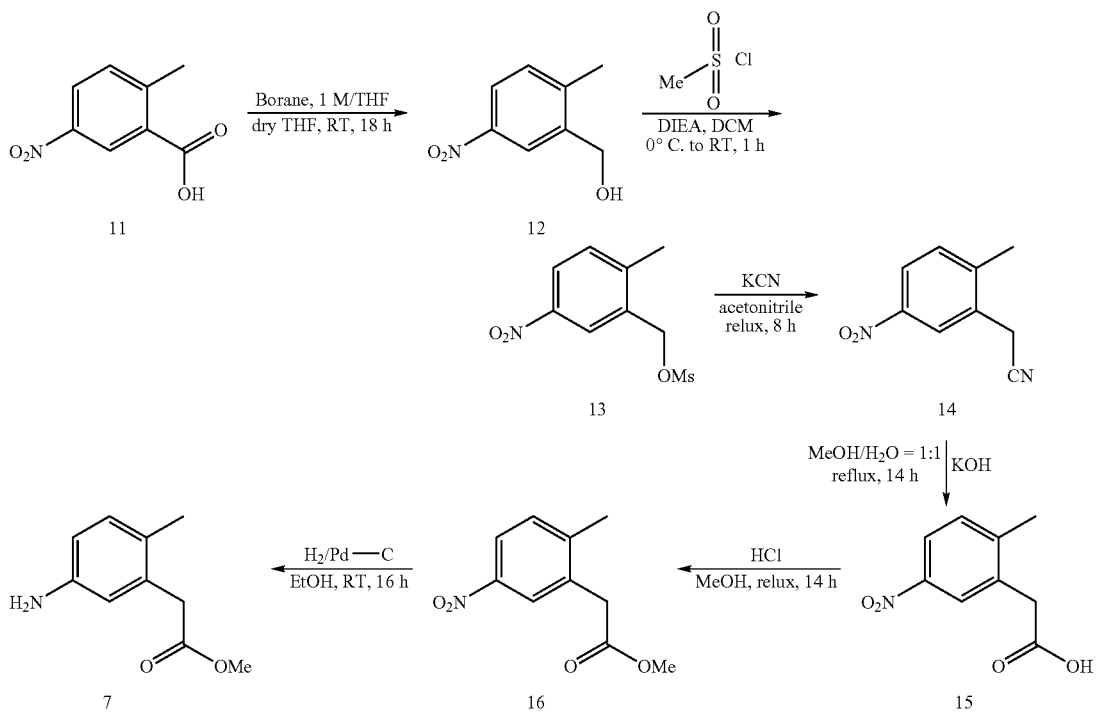

2-Methyl-5-nitrobenzoic acid (5.0 g, 27.5 mmol) is dissolved in 50 mL anhydrous THF. After adding 41.3 mL 1M borane in THF solution (41.3 mmol), the reaction is stirred in RT for 18 hours. The reaction is quenched by a solution of potassium carbonate (4.5 g) in 100 mL water. After removing THF under vacuum, the aqueous solution is extracted with DCM and the combined organic layer is washed by brine and dried over sodium sulfate. After filtering and removing the solvent under the vacuum, the final product compound (12) (2-methyl-5-nitrophenyl)-methanol is the pale yellow solid, 4.3 g.

(2-methyl-5-nitrophenyl)-methanol (4.3 g, 25.7 mmol) is dissolved in 100 mL anhydrous DCM and cooled down to 0° C. and treated with methanesulfonyl chloride (3.22 g, 28.3 mmol) and DIEA (5.36 mL, 30.8 mmol) for 30 minutes. The reaction is warmed up to the room temperature and stirred for another 30 minutes. The reaction is quenched by adding 30 mL water. The organic layer is washed with brine and dried over sodium sulfate and filtered. After removing the solvent under the vacuum, the final product compound (13) (2-methyl-5-nitrophenyl)-methyl methylsulfonate is the yellow oil, 6.2 g.

(2-Methyl-5-nitrophenyl)-methyl methylsulfonate (6.2 g, 25.3 mmol) and potassium cyanide (5.0 g, 76 mmol) are refluxed in 200 mL acetonitrile for 8 hours and cooled down to RT. After removing solvent under the vacuum, the crude product is dissolved in DCM and filtered. The filtrate is washed by brine and dried over sodium sulfate. After removing solvent under the vacuum, the crude product is purified by flash chromatography using EA/Hexane (1:1). The final product compound (14) 2-(2-methyl-5-nitrophenyl)-ethanenitrile is the yellow solid, 3.1 g.

2-(2-methyl-5-nitrophenyl)-ethanenitrile (2.5 g, 14.2 mmol) is dissolved in 50 mL methanol. Potassium hydroxide (8.0 g, 142 mmol) in 50 mL water is added and the reaction is heated to reflux for 14 hours. After cooling down and removing the methanol, the aqueous layer is washed with DCM and ether. The combined organic layer is washed with brine and dried over sodium sulfate and filtered. After removing the solvent under the vacuum, the final product compound (15) 2-(2-methyl-5-nitrophenyl)-acetic acid is the orange solid, 1.9 g.

2-(2-methyl-5-nitrophenyl)-acetic acid (1.9 g, 9.7 mmol) is dissolved in 50 mL methanol and 5 mL 4M HCl in 1,4-dioxane is added. The reaction is heated to reflux for 14 hours. After cooling down and removing solvent, the crude product is dissolved in 50 mL water and basified by 2N sodium hydroxide water solution to pH>12. The solution is extracted by ethyl acetate, and the combined organic layer is washed by brine and dried over sodium sulfate and filtered. After removing solvent, the final product compound (16) 2-(2-methyl-5-nitrophenyl)-acetic acid methyl ester is the dark yellow solid, 1.85 g.

2-(2-methyl-5-nitrophenyl)-acetic acid methyl ester (1.85 g, 8.85 mmol) is dissolved in 40 mL ethanol. 180 mg 10% palladium carbon is added and a hydrogen balloon is used. The reaction is stirred in RT for 16 hours. After removing the palladium carbon by going through a celite plug and removing the solvent, the crude product is purified by flash chromatography using MeOH/DCM (7%:93%). The final product compound (7) 2-(5-amino-2-methyl-phenyl)-acetic acid methyl ester is the yellow oil, 1.5 g.

6-chloro-4-methylamino-pyridine-3-carbaldehyde (850 mg, 5 mmol) is mixed with 2-(5-amino-2-methyl-phenyl)-acetic acid methyl ester (compound 7, 1.35 g, 7.5 mmol) and potassium carbonate (2.07 g, 15 mmol) in 15 mL DMF, heat up to 100° C. for 16 hours. After cooling down and removing solvent under the vacuum, the crude product is purified by flash chromatography using EA/Hexane (6:4). The final compound (8) 3-(4-amino-2-methyl-phenyl)-7-chloro-1-methyl-1H-[1,6]naphthyridin-2-one is the pale solid, 1.30 g.

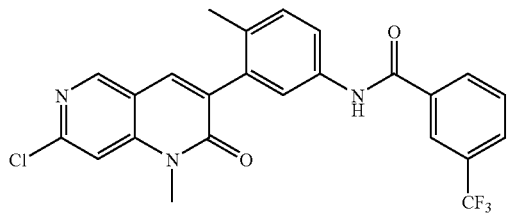

3-(4-Amino-2-methyl-phenyl)-7-chloro-1-methyl-1H-[1,6]naphthyridin-2-one (600 mg, 2.0 mmol) is mixed with 3-trifluoromethyl-benzoyl chloride (440 mg, 2.1 mmol) and 520 µL DIEA (3.0 mmol) in 20 mL anhydrous DCM. The reaction is stirred in RT for 4 hours. After removing solvent under the vacuum, the crude product is purified by flash chromatography using EA/Hexane (1:1). The final compound (9) N-[3-(7-Chloro-1-methyl-2-oxo-1,2-dihydro-[1,6]naphthyridin-3-yl)-4-methyl-phenyl]-3-trifluoromethyl-benzamide is the white solid, 900 mg: $^1$H NMR 400 MHz (CDCl$_3$) δ 8.58 (s, 1H), 8.25 (s, 1H), 8.13 (s, 1H), 8.08 (d, 1H, J=7.8 Hz), 7.78 (d, 1H, J=7.8 Hz), 7.71 (s, 1H), 7.62 (m, 2H), 7.44 (d, 1H, J=5.8 Hz), 7.31 (s, 1H), 7.20 (d, 1H, J=8.2 Hz), 3.76 (s, 3H), 2.03 (s, 3H); MS m/z 560.3 (M+1).

N-[3-(7-Chloro-1-methyl-2-oxo-1,2-dihydro-[1,6]naphthyridin-3-yl)-4-methyl-phenyl]-3-trifluoromethyl-benzamide (50 mg, 0.106 mmol) is mixed with 6-methoxy-pyridin-3-ylamine (20 mg, 0.16 mmol), Pd$_2$(dba)$_2$ (2.4 mg, 2.5%), 1,3-Bis(2,6-di-i-propylphenyl)imidazolium chloride (2.3 mg, 5%) and potassium tert-butanoxide (17.8 mg, 0.159 mmol) under an argon environment. 6 mL of anhydrous 1,4-dioxane is added and the reaction is continued at 100° C. for 14 hours. After cooling down and removing solvent under vacuum, the crude product is dissolved in DMSO and purified by reverse phase preparative HPLC to give the final product as a pale solid: $^1$H NMR 400 MHz (CDCl$_3$) δ 11.61 (s, 1H), 8.26 (d, 1H, J=2.6 Hz), 8.16 (s, 1H), 8.10 (s, 1H), 8.05 (d, 1H, J=7.9 Hz), 7.95 (s, 1H), 7.80 (d, 1H, J=7.7 Hz), 7.69 (d, 1H, J=2.1 Hz), 7.61 (m, 2H), 7.51 (s, 1H), 7.42 (dd, 1H, J=6.0 Hz), 6.89 (d, 1H, J=8.7 Hz), 6.38 (s, 1H), 4.00 (s, 3H), 3.52 (s, 3H), 2.15 (s, 3H), MS m/z 560.3 (M+1).

Example 9

N-[3-(7-Ethylamino-1-methyl-2-oxo-1,2-dihydro-[1,6]naphthyridin-3-yl)-4-methyl-phenyl]-3-trifluoromethyl-benzamide

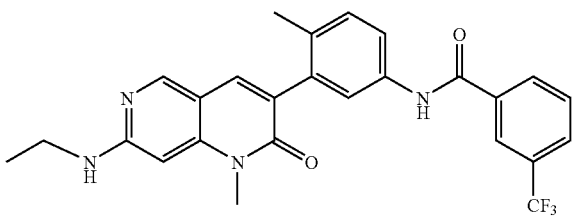

N-[3-(7-Chloro-1-methyl-2-oxo-1,2-dihydro-[1,6]naphthyridin-3-yl)-4-methyl-phenyl]-3-trifluoromethyl-benzamide (50 mg, 0.106 mmol) is mixed with ethylamine (0.14 mL 70% in water, 2.2 mmol) in a sealed tube. 1 mL of n-butanol is added and the reaction is stirred at 100° C. for 16 hours. After cooling and removal of solvent under vacuum, the crude product is dissolved in DMSO and purified by reverse phase preparative HPLC to give the final product as white solid: $^1$H NMR 400 MHz (DMSO-d$_6$) δ 10.47 (s, 1H), 8.48 (s, 1H), 8.29 (s, 1H), 8.25 (d, 1H, J=8.0 Hz), 7.96 (d, 1H, J=7.8 Hz), 7.78 (m, 2H), 7.66 (m, 2H), 7.26 (d, 1H, J=9.0 Hz), 6.46 (s, 1H), 3.57 (s, 3H), 3.39 (q, 2H, J=7.1 Hz), 2.13 (s, 3H), 1.22 (t, 3H, J=7.1 Hz); MS m/z 481.2 (M+1).

Example 10

N-(4-Methyl-3-{1-methyl-2-oxo-7-[(pyridin-3-ylmethyl)-amino]-1,2-dihydro-[1,6]naphthyridin-3-yl}-phenyl)-3-trifluoromethyl-benzamide

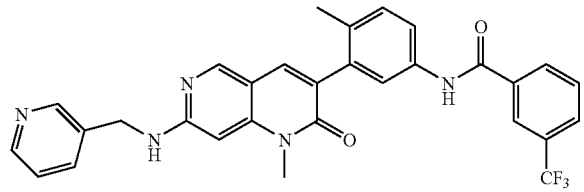

N-[3-(7-Chloro-1-methyl-2-oxo-1,2-dihydro-[1,6]naphthyridin-3-yl)-4-methyl-phenyl]-3-trifluoromethyl-benzamide (50 mg, 0.106 mmol) is mixed with 3-(aminomethyl)-pyridine (18 mg, 0.16 mmol), Pd$_2$(dba)$_2$ (2.4 mg, 2.5%), 1,3-Bis(2,6-di-i-propylphenyl)-imidazolium chloride (2.3 mg, 5%) and potassium tert-butanoxide (17.8 mg, 0.159 mmol) under an argon environment. 6 mL of anhydrous 1,4-dioxane is added and the reaction is continued at 100° C. for 14 hours. After cooling and removal of solvent under vacuum, the crude product is dissolved in DMSO and purified by reverse phase preparative HPLC to give the final product as a pale solid: $^1$H NMR 400 MHz (DMSO-d$_6$) δ 10.46 (s, 1H), 8.79 (s, 1H), 8.68 (d, 1H, J=4.6 Hz), 8.44 (s, 1H), 8.29 (s, 1H), 8.24 (t, 2H, J=7.5 Hz), 7.96 (d, 2H, J=7.8 Hz), 7.76 (m, 3H), 7.65 (m, 2H), 7.24 (d, 1H, J=8.3 Hz), 6.46 (s, 1H), 4.74 (s, 2H), 3.52 (s, 3H), 2.11 (s, 3H); MS m/z 544.3 (M+1).

Example 11

N-{3-[7-(3-Dimethylaminomethyl-phenylamino)-1-methyl-2-oxo-1,2-dihydro-[1,6]naphthyridin-3-yl]-4-methyl-phenyl}-3-trifluoromethyl-benzamide

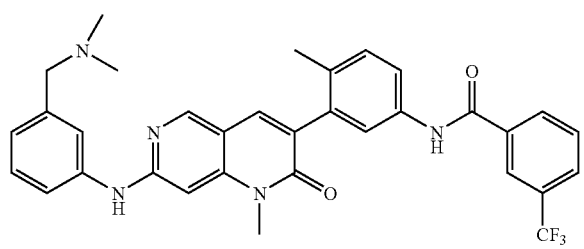

N-[3-(7-Chloro-1-methyl-2-oxo-1,2-dihydro-[1,6]naphthyridin-3-yl)-4-methyl-phenyl]-3-trifluoromethyl-benzamide (50 mg, 0.106 mmol) is mixed with 3-dimethyl-aminomethyl-phenylamine (24 mg, 0.16 mmol), Pd$_2$(dba)$_2$ (2.4 mg, 2.5%), 1,3-Bis(2,6-di-1-propylphenyl)imidazolium chloride (2.3 mg, 5%) and potassium tert-butanoxide (17.8 mg, 0.159 mmol) under an argon environment. 6 mL of anhydrous 1,4-dioxane is added and the reaction is continued at 100° C. for 14 hours. After cooling and removal of solvent under vacuum, the crude product is dissolved in DMSO and purified by reverse phase preparative HPLC to give the final product as a pale solid: $^1$H NMR 400 MHz (DMSO-d$_6$) δ 10.48 (s, 1H), 9.64 (s, 1H), 8.60 (s, 1H), 8.30 (s, 1H), 8.26 (d, 1H, J=8.9 Hz), 7.96 (d, 1H, J=7.8 Hz), 7.87 (s, 2H), 7.79 (t, 1H, J=7.8 Hz), 7.67 (m, 3H), 7.41 (t, 1H, J=7.8 Hz), 7.27 (d, 1H, J=9.1 Hz), 7.08 (d, 1H, J=7.7 Hz), 6.78 (s, 1H), 4.28 (d, 2H, J=5.0 Hz), 3.58 (s, 3H), 2.77 (d, 6H, J=4.6 Hz), 2.14 (s, 3H); MS m/z 586.3 (M+1).

Example 12

N-(4-Methyl-3-{1-methyl-7-[3-(4-methyl-piperazin-1-yl)-phenylamino]-2-oxo-1,2-dihydro-[1,6]naphthyridin-3-yl}-phenyl)-3-trifluoromethyl-benzamide

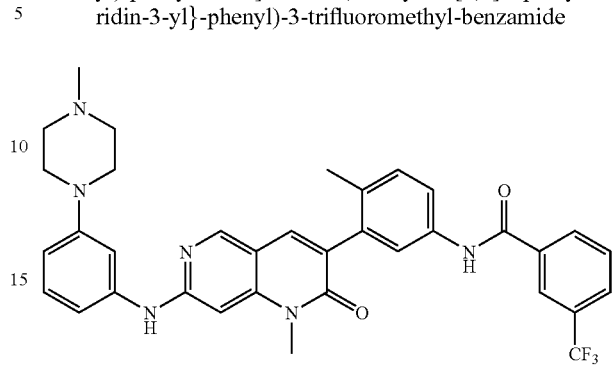

N-[3-(7-Chloro-1-methyl-2-oxo-1,2-dihydro-[1,6]naphthyridin-3-yl)-4-methyl-phenyl]-3-trifluoromethyl-benzamide (50 mg, 0.106 mmol) is mixed with 3-(4-Methyl-piperazin-1-yl)-phenylamine (31 mg, 0.16 mmol), Pd$_2$(dba)$_2$ (2.4 mg, 2.5%), 1,3-Bis(2,6-di-1-propylphenyl)imidazolium chloride (2.3 mg, 5%) and potassium tert-butanoxide (17.8 mg, 0.159 mmol) under an argon environment. 6 mL of anhydrous 1,4-dioxane is added and the reaction is continued at 100° C. for 14 hours. After cooling and removal of solvent under vacuum, the crude product is dissolved in DMSO and purified by reverse phase preparative HPLC to give the final product as a pale solid: $^1$H NMR 400 MHz (DMSO-d$_6$) δ 10.47 (s, 1H), 9.43 (s, 1H), 8.58 (s, 1H), 8.30 (s, 1H), 8.26 (d, 1H, J=8.1 Hz), 7.21 (d, 1H, J=7.9 Hz), 7.83 (s, 1H), 7.79 (t, 1H, J=7.8 Hz), 7.69 (m, 2H), 7.37 (s, 1H), 7.21 (m, 3H), 6.74 (s, 1H), 6.65 (d, 1H, J=6.5 Hz), 3.80 (d, 2H, J=13.9 Hz), 3.56 (s, 3H), 3.54 (d, 2H, J=13.9 Hz), 3.18 (m, 2H), 2.98 (m, 2H), 2.88 (d, 3H, J=3.8 Hz), 2.14 (s, 3H); MS m/z 627.3 (M+1).

Example 13

N-[3-(7-Amino-1-methyl-2-oxo-1,2-dihydro-[1,6]naphthyridin-3-yl)-4-methyl-phenyl]-3-trifluoromethyl-benzamide

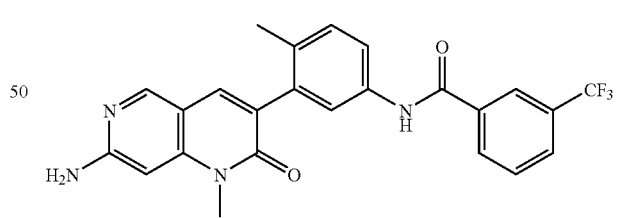

N-[3-(7-Chloro-1-methyl-2-oxo-1,2-dihydro-[1,6]naphthyridin-3-yl)-4-methyl-phenyl]-3-trifluoromethyl-benzamide (100 mg, 0.21 mmol) is mixed with benzylamine (35 mg, 0.32 mmol), Pd$_2$(dba)$_2$ (4.8 mg, 2.5%), 1,3-Bis(2,6-di-i-propylphenyl)imidazolium chloride (4.6 mg, 5%) and potassium tert-butanoxide (35.6 mg, 0.32 mmol) under an argon environment. 6 mL of anhydrous 1,4-dioxane is added and the reaction is continued at 100° C. for 14 hours. After cooling and removal of solvent under vacuum, the crude product is dissolved in DMSO and purified by reverse phase preparative HPLC to give the product N-[3-(7-Benzylamino-1-methyl-2- oxo-1,2-dihydro-[1,6]naphthyridin-3-yl)-4-methyl-phenyl]-3-trifluoromethyl-benzamide as pale solid. This product is dissolved into 10 mL of ethanol and 8 mg of 10% palladium carbon powder is added. The reaction is stirred at room temperature under a 50 psi hydrogen environment for 16 hours. After passing through a celite plug to remove the palladium carbon and removing the solvent, the crude product is dissolved in DMSO and purified by reverse phase preparative HPLC to give the final product as a white solid: $^1$H NMR 400 MHz (DMSO-$d_6$) δ 10.42 (s, 1H), 8.35 (s, 1H), 8.31 (s, 1H), 8.26 (d, 1H, J=7.8 Hz), 7.96 (d, 1H, J=7.7 Hz), 7.78 (t, 1H, J=7.8 Hz), 7.69 (m, 2H), 7.61 (s, 1H), 7.24 (d, 1H, J=8.1 Hz), 6.53 (s, 2H), 6.29 (s, 1H), 3.49 (s, 3H), 2.12 (s, 3H); MS m/z 453.2 (M+1).

By repeating the procedures described in the above examples, using appropriate starting materials, the following compounds of Formula I, as identified in Table 1, are obtained.

TABLE 1

| Compound Number | Structure | Physical Data $^1$H NMR and MS (m/z) |
|---|---|---|
| 14 | 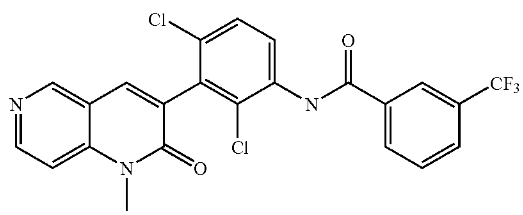 | $^1$H NMR 400 MHz (CDCl$_3$) δ 8.87 (s, 1H), 8.70 (d, 1H), 8.56 (d, 1H), 8.454 (s, 1H), 8.19 (s, 1H), 8.07 (d, 1H), 7.84 (t, 1H), 7.78 (s, 1H), 7.67 (t, 1H), 7.52 (d, 1H), 7.29 (d, 1H), 3.78 (s, 3H); MS m/z 642.3 (M + 1). |
| 15 | 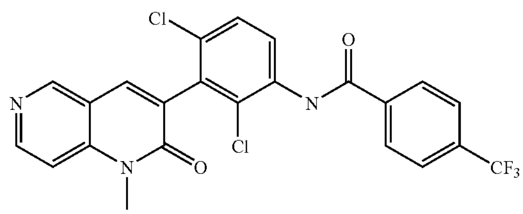 | $^1$H NMR 400 MHz (CDCl$_3$) δ 8.87 (s, 1H), 8.70 (d, 1H), 8.58 (d, 1H), 8.46 (s, 1H), 8.01–8.03 (m, 2H), 7.78–7.83 (m, 3H), 7.52 (d, 1H), 7.30 (d, 1H), 3.78 (s, 3H); MS m/z 493.2 (M + 1). |
| 16 | 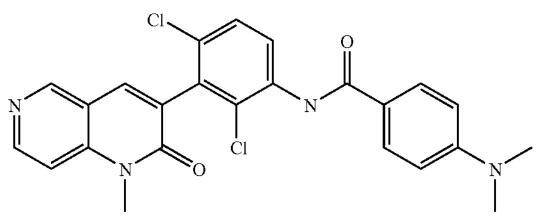 | $^1$H NMR 400 MHz (CDCl$_3$) δ 8.87 (s, 1H), 8.69 (s, 1H), 8.64 (d, 1H), 8.37 (s, 1H), 7.76–7.83 (m, 3H), 7.47 (d, 1H), 7.30 (m, 1H), 6.72 (m, 2H), 6.58 (m, 1H), 3.76 (s, 3H), 3.06 (s, 6H); MS m/z 468.15 (M + 1). |
| 17 | 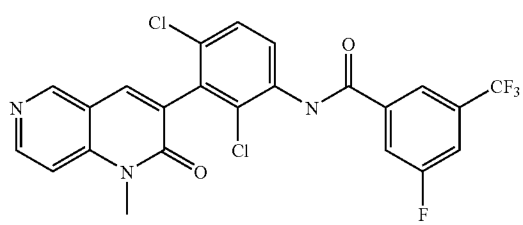 | $^1$H NMR 400 MHz (CDCl$_3$) δ 8.87 (s, 1H), 8.70 (d, 1H), 8.46 (d, 1H), 8.45 (s, 1H), 7.96 (s, 1H), 7.81 (m, 1H), 7.78 (s, 1H), 7.55 (m, 1H), 7.51 (d, 1H), 7.30 (d, 1H), 3.78 (s, 3H); MS m/z 511.1 (M + 1). |
| 18 | 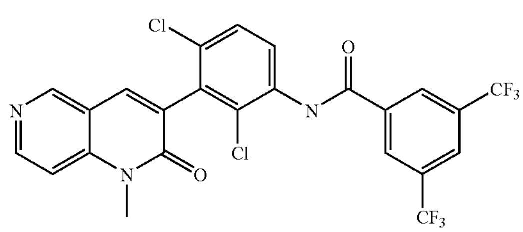 | $^1$H NMR 400 MHz (CDCl$_3$) δ 9.02 (s, 1H), 8.78 (d, 1H), 8.57 (s, 1H), 8.60 (d, 1H), 8.11 (m, 3H), 7.86 (s, 1H), 7.54 (d, 1H), 7.42 (d, 1H), 3.82 (s, 3H); MS m/z 562.2 (M + 1). |

TABLE 1-continued

| Compound Number | Structure | Physical Data $^1$H NMR and MS (m/z) |
|---|---|---|
| 19 | 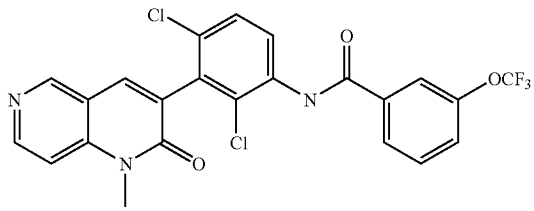 | $^1$H NMR 400 MHz (CDCl$_3$) δ 8.86 (s, 1H), 8.70 (d, 1H), 8.57 (d, 1H), 8.43 (s, 1H), 7.78–7.83 (m, 3H), 7.56–7.60 (m, 2H), 7.45 (m, 1H), 7.29 (d, 1H), 3.78 (s, 3H); MS m/z 509.15 (M + 1). |
| 20 | 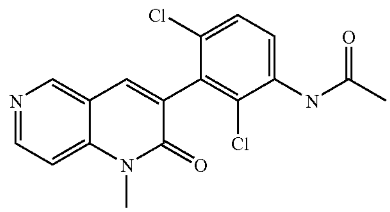 | $^1$H NMR 400 MHz (CDCl$_3$) δ 8.85 (s, 1H), 8.68 (d, 1H), 8.40 (d, 1H), 7.73 (s, 1H), 7.69 (s, 1H), 7.43 (d, 1H), 7.27 (d, 1H), 3.77 (s, 3H), 2.25 (s, 3H); MS m/z 363.2 (M + 1). |
| 21 | 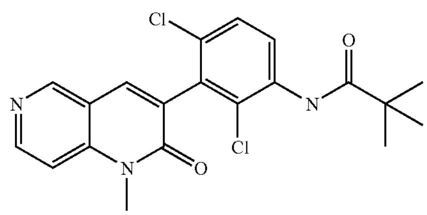 | $^1$H NMR 400 MHz (CDCl$_3$) δ 8.87 (s, 1H), 8.69 (d, 1H), 8.48 (d, 1H), 8.04 (s, 1H), 7.74 (s, 1H), 7.44 (d, 1H), 7.29 (d, 1H), 3.77 (s, 3H), 1.33 (s, 9H); MS m/z 405.20 (M + 1). |
| 22 | 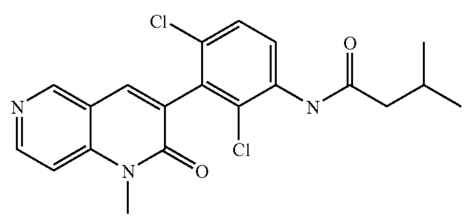 | $^1$H NMR 400 MHz (CDCl$_3$) δ 8.85 (s, 1H), 8.68 (d, 1H), 8.45 (d, 1H), 7.74 (s, 1H), 7.63 (s, 1H), 7.43 (d, 1H), 7.28 (s, 1H), 3.76 (s, 3H), 2.31 (d, 2H), 1.26 (m, 1H), 1.03 (d, 6H); MS m/z 405.20 (M + 1). |
| 23 | 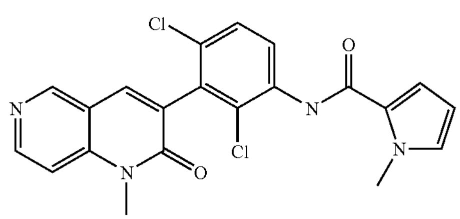 | $^1$H NMR 400 MHz (CDCl$_3$) δ 8.86 (s, 1H), 8.69 (d, 1H), 8.50 (d, 1H), 8.21 (s, 1H), 7.76 (s, 1H), 7.45 (d, 1H), 7.28 (d, 1H), 6.83 (d, 1H), 6.76 (dd, 1H), 6.16 (dd, 1H), 4.00 (s, 3H), 3.73 (s, 3H); MS m/z 428.2 (M + 1). |
| 24 | 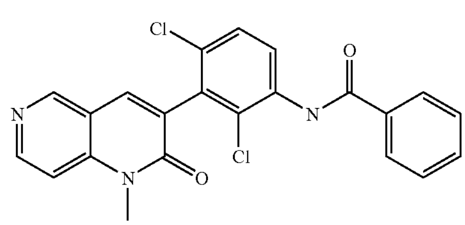 | $^1$H NMR 400 MHz (CDCl$_3$) δ 9.16 (s, 1H), 8.80 (d, 1H), 8.65 (d, 1H), 8.44 (s, 1H), 8.89–7.92 (m, 3H), 7.58–7.63 (m, 2H), 4.46–7.56 (m, 3H), 3.86 (s, 3H); MS m/z 625.2 (M + 1). |
| 25 | 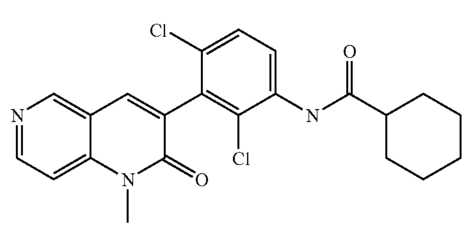 | $^1$H NMR 400 MHz (CDCl$_3$) δ 8.86 (s, 1H), 8.68 (d, 1H), 8.46 (d, 1H), 7.73 (s, brod. 1H), 7.43 (d, 1H), 7.28 (d, 1H), 3.77 (s, 3H), 2.31 (m, 1H), 1.20–2.02 (m, 10H); MS m/z 431.00 (M + 1). |

TABLE 1-continued

| Compound Number | Structure | Physical Data $^1$H NMR and MS (m/z) |
|---|---|---|
| 26 | 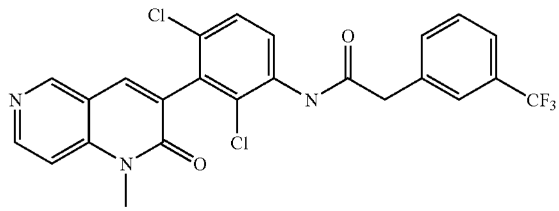 | $^1$H NMR 400 MHz (CDCl$_3$) δ 8.84 (s, 1H), 8.67 (d, 1H), 8.36 (d, 1H), 7.77 (s, 1H), 7.69 (s, 1H), 7.64 (s, 1H), 7.51–7.59 (m, 3H), 7.41 (d, 1H), 7.28 (d, 1H), 3.86 (s, 2H), 3.74 (s, 3H); MS m/z 507.2 (M + 1). |
| 27 | 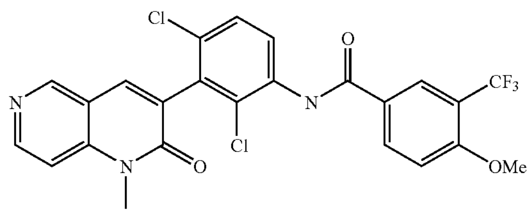 | $^1$H NMR 400 MHz (CDCl$_3$): δ3.78 (s, 3H), 3.93 (s, 3H), 7.05(d, 1H), 7.43 (d, 1H), 7.52 (bs, 1H), 7.80 (s, 1H), 7.99 (dd, 1H), 8.07 (s, 1H), 8.27 (s, 1H), 8.50 (d, 1H), 8.72 (bs, 1H), 9.05 (bs, 1H). MS m/z 522.2 (M + 1). |
| 28 | 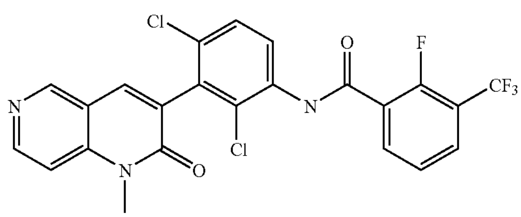 | $^1$H NMR 400 MHz (DMSO-d$_6$) δ3.68 (s, 3H), 7.54–7.58(m, 2H), 7.66 (d, 1H), 7.83 (d, 1H), 7.97 (t, 1H), 8.03 (t, 1H), 8.16 (s, 1H), 8.66 (d, 1H), 8.96 (s, 1H), 10.52(s, 1H). MS m/z 510.2 (M + 1). |
| 29 | 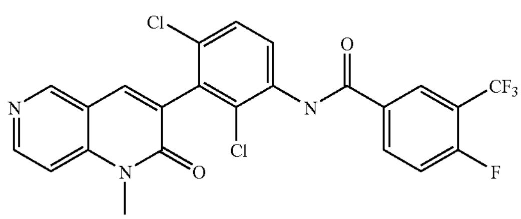 | $^1$H NMR 400 MHz (DMSO-d$_6$) δ3.62 (s, 3H), 7.51 (d, 1H), 7.60–7.69 (m, 3H), 8.11 (s, 1H), 8.34–8.36 (m, 2H), 8.60 (d, 1H), 8.91 (s, 1H), 10.47 (s, 1H). MS m/z 510.2 (M + 1). |
| 30 | 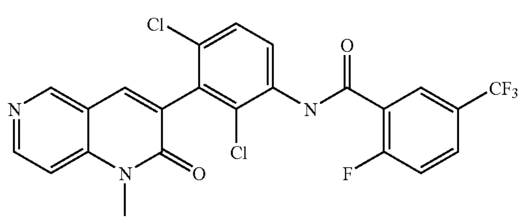 | $^1$H NMR 400 MHz (DMSO-d$_6$) δ3.69 (s, 3H), 7.60 (d, 1H), 7.64 (t, 1H), 7.68 (d, 1H), 7.90 (d, 1H), 8.02–8.04 (m, 1H), 8.12 (dd, 1H), 8.18 (s, 1H), 8.67 (d, 1H), 8.97 (s, 1H), 10.41 (s, 1H). MS m/z 510.2 (M + 1). |
| 31 | 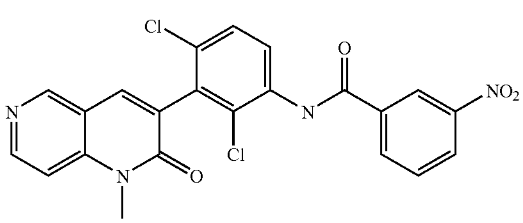 | $^1$H NMR 400 MHz (CDCl$_3$) δ8.79 (s, 1H), 8.71 (t, 1H), 8.60 (m, 2H), 8.36 (m, 2H), 8.19 (dd, 1H), 7.71 (s, 1H), 7.65 (m, 1H), 7.44 (m, 1H), 7.23 (m, 1H), 3.70 (s, 3H); MS m/z 470.2 (M + 1). |
| 32 | 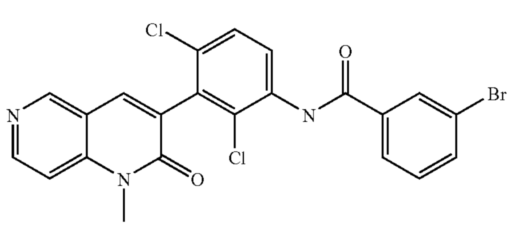 | $^1$H NMR 400 MHz (CDCl$_3$) δ8.80 (s, 1H), 8.62 (d, 1H), 8.46 (m, 1H), 8.34 (s, 2H), 7.99 (t, 1H), 7.72 (dd, 1H), 7.71 (s, 1H), 7.64 (dd, 1H), 7.43 (d, 1H), 7.32 (t, 1H), 7.24 (d, 1H), 3.71 (s, 3H); MS m/z 504.2 (M + 1). |

TABLE 1-continued

| Compound Number | Structure | Physical Data $^1$H NMR and MS (m/z) |
|---|---|---|
| 33 | 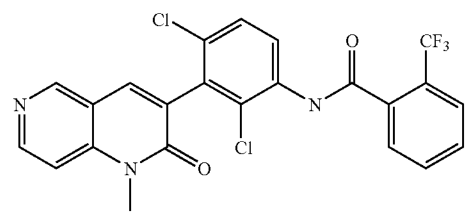 | $^1$H NMR 400 MHz (CDCl$_3$) δ8.87 (s, 1H), 8.69 (s, 1H), 8.57 (d, 1H), 7.99 (s, 1H), 7.78 (d, 1H), 7.78 (s, 1H), 7.76–7.69 (m, 3H), 7.52 (d, 1H), 7.31 (d, 1H), 3.77 (s, 3H); MS m/z 493.2 (M + 1). |
| 34 | 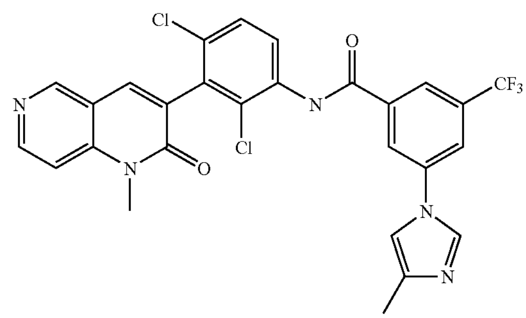 | $^1$H NMR 400 MHz (CDCl$_3$) δ8.86 (s, 1H), 8.73 (s, 1H), 8.70 (d, 1H), 8.36 (d, 1H), 8.16 (t, 1H), 8.08 (s, 1H), 7.90 (s, 1H), 7.80 (d, 1H), 7.79 (s, 1H), 7.49 (d, 1H), 7.30 (d, 1H), 7.12 (s, 1H), 3.75 (s, 3H), 2.29 (s, 3H); MS m/z 573.10 (M + 1). |
| 35 | 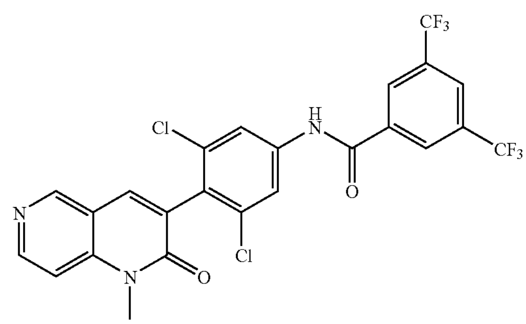 | $^1$H NMR 400 MHz (CD$_3$OD) δ3.75 (s, 3H), 7.76(d, 1H), 7.93 (s, 2H), 8.05 (s, 1H), 8.15 (s, 1H), 8.06 (s, 1H), 8.50 (s, 2H), 8.62(d, 1H), 9.00 (s, 1H). MS m/z 560.2 (M + 1). |
| 36 | 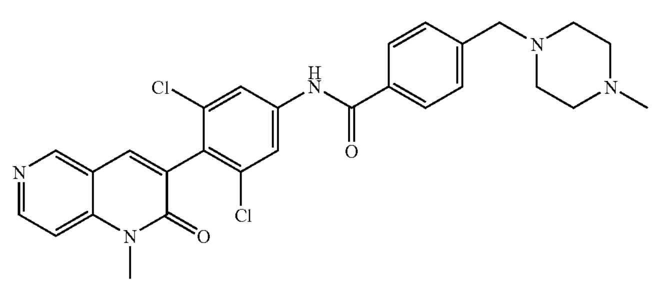 | $^1$H NMR 400 MHz (CD$_3$OD) δ2.30 (s, 3H), 2.53 (bs, 8H), 3.63 (s, 2H), 3.80 (s, 3H), 7.41 (d, 2H), 7.52 (d, 1h), 7.83 (d, 2H), 7.89 (s, 2h), 7.96 (s, 1H), 8.54 (d, 1H), 8.82 (s, 1H). MS m/z 536.2 (M + 1). |
| 37 | 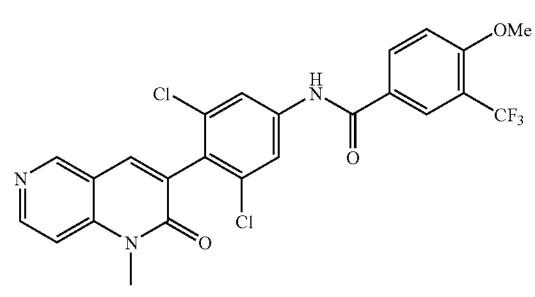 | $^1$H NMR 400 MHz (CDCl$_3$) δ3.81 (s, 3H), 3.90 (s, 3H), 7.01(d, 1H), 7.49 (d, 1H), 7.66 (s, 2H), 7.79 (s, 1H), 8.04 (s, 1H), 8.14 (dd, 1H), 8.70(d, 1H), 9.01 (s, 1H), 9.08 (s, 1H). MS m/z 522.2 (M + 1). |

TABLE 1-continued

| Compound Number | Structure | Physical Data $^1$H NMR and MS (m/z) |
|---|---|---|
| 38 | 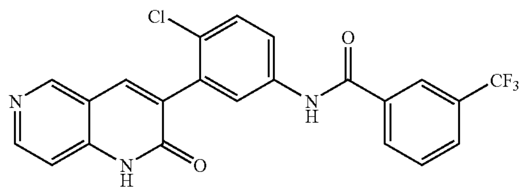 | $^1$H NMR 400 MHz (MEOD) δ 9.19 (s, 1H), 8.65 (d, 1H), 8.28 (s, 1H), 8.22 (m, 2H), 7.90 (d, 1H), 7.76 (m, 2H), 7.68 (d, 1H), 7.58 (d, 1H); MS m/z 444.1 (M + 1). |
| 39 | 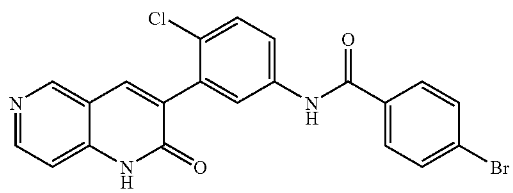 | $^1$H NMR 400 MHz (MEOD) δ 9.22 (s, 1H), 8.66 (d, 1H), 8.22 (s, 1H), 7.94 (d, 1H), 7.85 (d, 2H), 7.73 (m, 2H), 7.68 (d, 2H), 7.52 (d, 1H); MS m/z 454.0 (M + 1). |
| 40 | 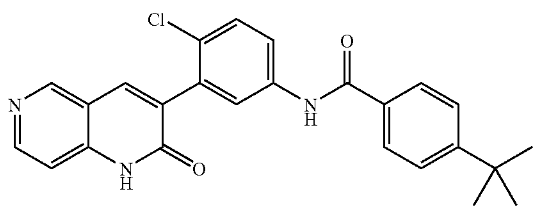 | $^1$H NMR 400 MHz (MEOD) δ 9.1 (s, 1H), 8.64 (d, 1H), 8.22 (s, 1H), 8.10 (s, 1H), 7.97 (d, 1H), 7.90 (d, 2H), 7.75 (dd, 1H), 7.69 (d, 1H), 7.58 (d, 2H), 7.54 (d, 1H), 1.40 (s, 9H); MS m/z 432.1 (M + 1). |
| 41 | 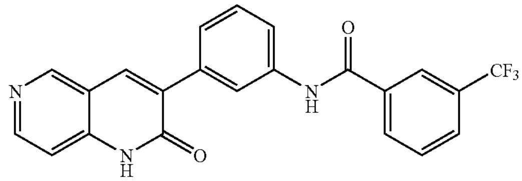 | $^1$H NMR 400 MHz (MEOD) δ 9.13 (s, 1H), 8.60 (d, 1H), 8.30 (s, 2H), 8.25–8.22 (m, 2H), 7.93 (d, 1H), 7.77–7.75 (m, 2H), 7.60 (m, 2H), 7.52 (t, 1H); MS m/z 410.1 (M + 1). |
| 42 | 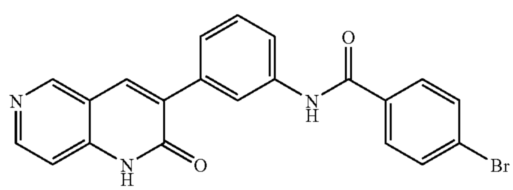 | $^1$H NMR 400 MHz (MEOD) δ 9.15 (s, 1H), 8.60 (d, 1H), 8.30 (s, 1H), 8.20 (d, 1H), 7.89 (d, 2H), 7.74–7.71 (m, 3H), 7.62 (d, 1H), 7.74 (s, 1H), 7.59 (d, 1H), 7.51 (t, 1H); MS m/z 420.0 (M + 1). |
| 43 | 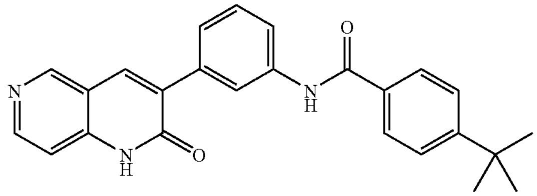 | $^1$H NMR 400 MHz (MEOD) δ 9.11 (s, 1H), 8.58 (d, 1H), 8.28 (s, 1H), 8.25 (d, 1H), 8.18 (s, 1H), 7.94 (d, 2H), 7.75 (d, 1H), 7.62–7.58 (m, 3H), 7.50 (t, 1H), 1.40 (s, 9H); MS m/z 398.1 (M + 1). |
| 44 | 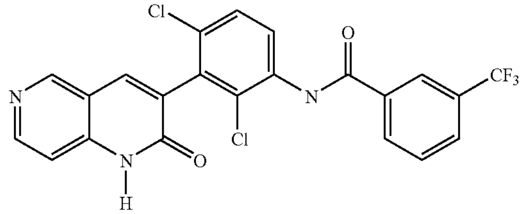 | $^1$H NMR 400 MHz (CDCl$_3$) δ 12.26 (s, 1H), 8.90 (d, 1H), 8.48–8.56 (m, 3H), 8.20 (s, 1H), 8.06 (d, 1H), 7.85 (m, 2H), 7.66 (m, 1H), 7.52 (d, 1H), 7.25 (s, 1H); MS m/z 479.05 (M + 1). |

TABLE 1-continued

| Compound Number | Structure | Physical Data ¹H NMR and MS (m/z) |
|---|---|---|
| 45 | 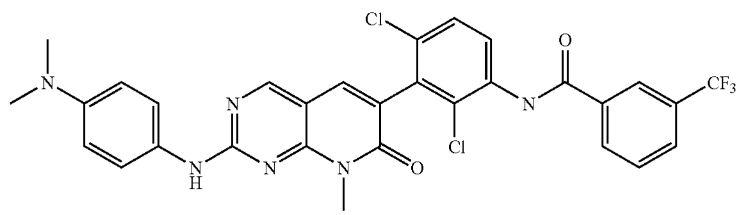 | ¹H NMR 400 MHz (CDCl$_3$) δ 8.59 (s, 1H), 8.57 (s, 1H), 8.41 (s, 1H), 8.19 (s, 1H), 8.06 (d, 1H), 7.86 (m, 3H), 7.58 (s, 1H), 7.53 (d, 1H), 7.44 (m, 2H), 3.82 (s, 3H), 3.18 (s, 6H); MS m/z 628.10 (M + 1). |
| 46 | 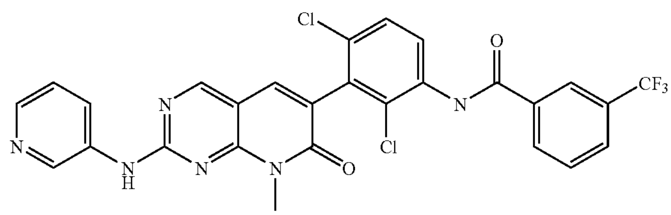 | ¹H NMR (CDCl$_3$): δ3.77 (s, 3H), 7.45(d, 1H), 7.57 (s, 1H), 7.61–7.65 (m, 2H), 7.78 (d, 1H), 7.99 (d, 1H), 8.12 (s, 1H), 8.35 (s, 1H), 8.37 (d, 1H), 8.43 (d, 1H), 8.48 (d, 1H), 8.65 (s, 1H), 9.42 (d, 1H). MS m/z 585.0 (M + 1). |
| 47 | 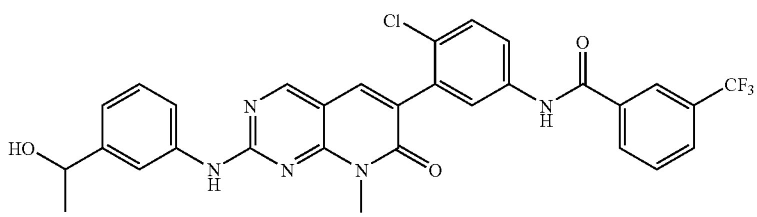 | ¹H NMR 400 MHz (CDCl$_3$) δ1.46(d, 3H), 3.75 (s, 3H), 4.89 (q, 1H), 7.09 (d, 1H), 7.32 (t, 2H), 7.44 (d, 1H), 7.50–7.53 (m, 1H), 7.55–7.57 (m, 2H), 7.71–7.74 (m, 2H), 7.82 (s, 1H), 8.01 (d, 1H), 8.08 (s, 1H), 8.33 (bs, 1H), 8.43 (s, 1H). MS m/z 594.0 (M + 1). |
| 48 | 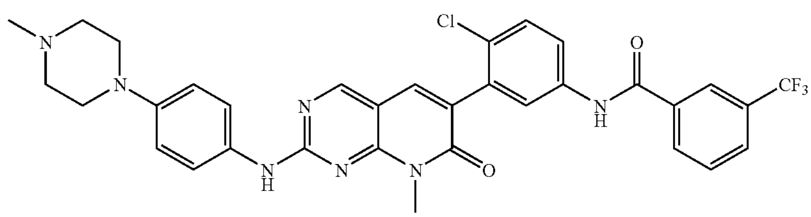 | ¹H NMR 400 MHz (CDCl$_3$) δ2.68 (s, 3H), 2.96–3.48 (m, 8H), 3.52 (s, 3H), 6.76 (d, 2H), 7.20 (d, 1H), 7.36–7.47 (m, 5H), 7.57 (s, 2H), 7.89 (d, 1H), 7.99 (s, 1H), 8.34 (s, 1H), 8.38 (s, 1H). MS m/z 648.1 (M + 1). |
| 49 | 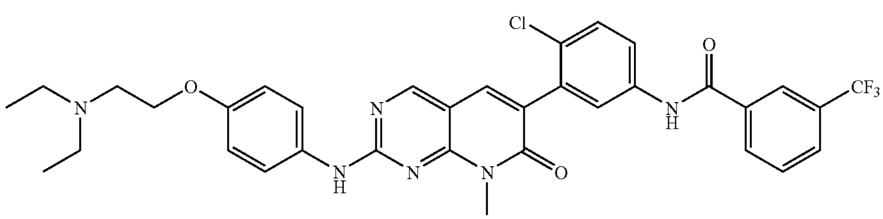 | ¹H NMR 400 MHz (CD$_3$OD) δ1.29 (t, 6H), 3.25 (m, 4H), 3.53 (m, 2H), 3.67 (s, 3H), 4.26 (m, 2H), 6.95 (d, 2H), 7.40 (d, 1H), 7.63–7.66 (m, 4H), 7.75 (s, 1H), 7.77 (d, 1H), 8.11 (d, 1H), 8.17 (s, 1H), 8.65 (s, 1H). MS m/z 665.1 (M + 1). |
| 50 | 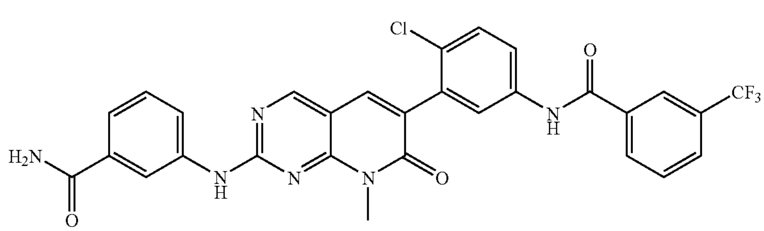 | ¹H NMR 400 MHz (CDCl$_3$) δ3.63 (s, 3H), 7.25 (d, 1H), 7.34 (d, 1H), 7.45 (t, 2H), 7.48 (dd, 1H), 7.55 (s, 1H), 7.58 (d, 1H), 7.60 (d 1H), 7.82 (d, 1H) 7.94 (d, 1H), 8.02–8.04 (m, 2H), 8.47 (s, 1H). MS m/z 593.0 (M + 1). |

TABLE 1-continued

| Compound Number | Structure | Physical Data $^1$H NMR and MS (m/z) |
|---|---|---|
| 51 | 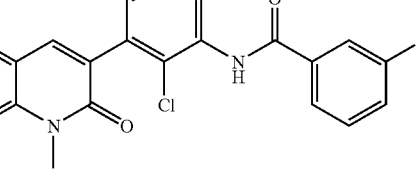 | $^1$H NMR (CDCl$_3$): δ3.72 (s, 3H), 7.37(d, 1H), 7.53 (t, 1H), 7.66 (s, 1H), 7.69 (d, 1H), 7.93 (d, 1H), 7.99 (d, 1H), 8.10 (s, 1H), 8.19 (d, 1H), 8.32 (d, 2H), 8.76 (s, 1H). MS m/z 585.0 (M + 1). |
| 52 | 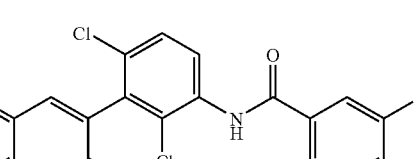 | $^1$H NMR 400 MHz (CDCl$_3$) δ3.75 (s, 3H), 6.97(d, 1H), 7.40 (t, 1H), 7.49 (d, 1H), 7.61 (d, 1H), 7.67 (t, 1H), 7.73 (d, 1H), 7.80 (s, 1H), 7.83 (d, 1H), 8.15 (m, 2H), 8.21 (s, 1H), 8.76 (s, 1H). MS m/z 599.1 (M + 1). |
| 53 | 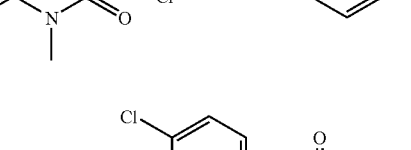 | $^1$H NMR 400 MHz (CDCl$_3$) δ3.74 (s, 3H), 4.69(s, 2H), 7.08 (d, 1H), 7.33 (t, 1H), 7.43 (d, 1H), 7.48 (s, 1H), 7.55–7.62 (m, 2H), 7.77 (m, 2H), 7.97 (d, 1H), 8.11 (s, 1H), 8.34 (s, 1H), 8.48 (d, 1H). MS m/z 614.0 (M + 1). |
| 54 | 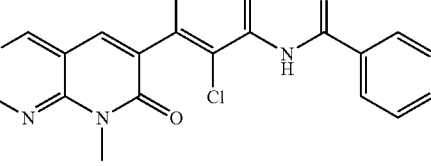 | $^1$H NMR 400 MHz (CDCl$_3$) δ3.19 (m, 4H), 3.71 (s, 3H), 3.87 (m, 4H), 7.04 (d, 1H), 7.43 (d, 1H), 7.46 (s, 1H), 7.58–7.63 (m, 3H), 7.77 (d, 1H), 7.97 (d, 1H), 8.10 (s, 1H), 8.33 (s, 1H), 8.42 (s, 1H), 8.48 (d, 1H). MS m/z 668.1 (M + 1). |
| 55 | 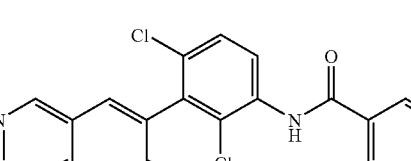 | $^1$H NMR 400 MHz (CDCl$_3$) δ2.82 (s, 3H), 2.97 (m, 2H), 3.30 (m, 2H), 3.56 (m, 4H), 3.71 (s, 3H), 6.91 (d, 2H), 7.43 (d, 1H), 7.47 (s, 1H), 7.57–7.62 (m, 3H), 7.77 (d, 1H), 7.97 (d, 1H), 8.11 (s, 1H), 8.34 (s, 1H), 8.44 (s, 1H), 8.48 (d, 1H). MS m/z 682.1 (M + 1). |
| 56 | 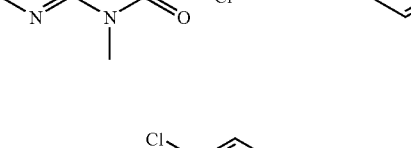 | $^1$H NMR 400 MHz (CDCl$_3$), δ3.77 (s, 3H), 6.39 (bs, 2H), 7.41–7.45 (m, 2H), 7.48–7.50 (m, 2H), 7.60 (t, 1H), 7.77 (t, 2H), 7.97 (d, 1H), 8.11 (s, 1H), 8.34 (s, 1H), 8.44 (s, 1H), 8.46–8.48 (m, 2H). MS m/z 627.0 (M + 1). |

TABLE 1-continued

| Compound Number | Structure | Physical Data $^1$H NMR and MS (m/z) |
|---|---|---|
| 57 | 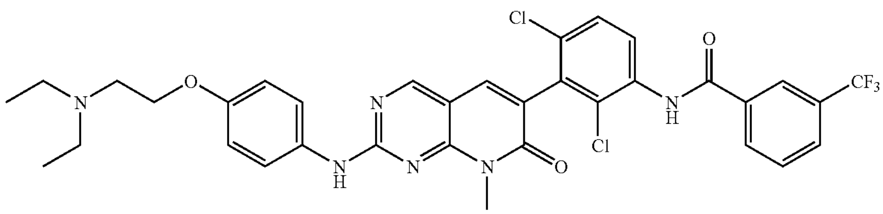 | $^1$H NMR 400 MHz (CD$_3$OD) δ1.27 (t, 6H), 3.25 (m, 4H), 3.52 (m, 2H), 3.67(s, 3H), 4.26 (m, 2H), 6.95 (d, 2H), 7.48 (d, 1H), 7.62–7.66 (m, 3H), 7.71–7.74 (m, 2H), 7.82 d, 1H), 8.14 (d, 1H), 8.20 (s, 1H), 8.65 (s, 1H). MS m/z 699.1 (M + 1). |
| 58 | 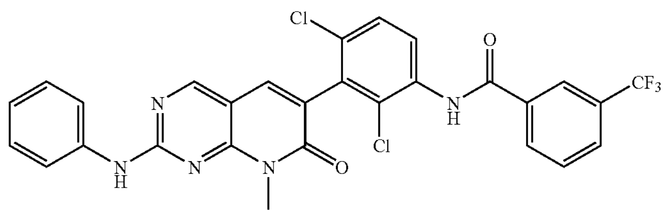 | $^1$H NMR (CD$_3$OD): δ 8.64 (d, 1H), 8.43 (s, 1H), 8.19(s, 1H), 8.06 (d, 1H), 8.06 (d, 1H), 7.92 (m, 1H), 7.85 (d, 1H), 7.66–7.74 (m, 3H), 7.51–7.57 (m, 3H), 7.25 (m, 2H), 7.18 (t, 1H), 3.82 (s, 3H); MS m/z 629.10 (M + 1). |
| 59 | 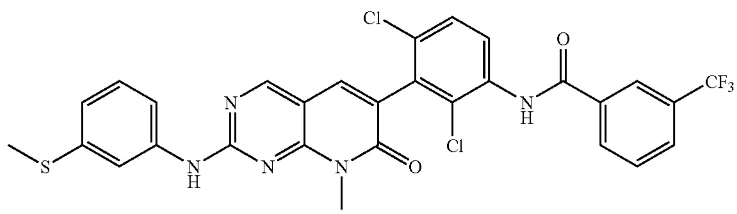 | $^1$H NMR 400 MHz (CDCl$_3$) δ2.45 (s, 3H), 3.74 (s, 3H), 6.98(d, 1H), 7.25 (t, 1H), 7.34 (d, 1H), 7.43 (d, 1H), 7.48 (s, 1H), 7.60 (t, 1H), 7.69 (s, 1H), 7.77 (d, 1H), 7.97 (d, 1H), 8.10 (s, 1H), 8.33 (s, 1H), 8.45 (s, 1H), 8.48 (d, 1H). MS m/z 630.0 (M + 1). |
| 60 | 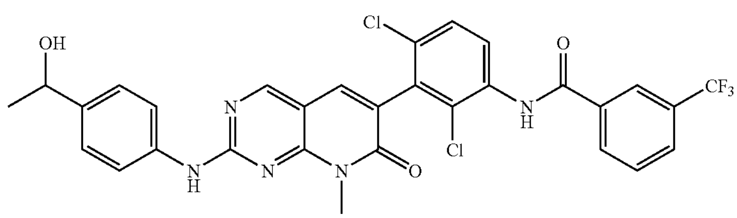 | $^1$H NMR 400 MHz (CDCl$_3$) δ1.45 (d, 3H), 3.73 (s, 3H), 4.86 (q, 1H), 7.36 (d, 2H), 7.43 (d, 1H), 7.48 (s, 1H), 7.60 (t, 1H), 7.64 (d, 2H), 7.77 (d, 1H), 7.97 (d, 1H), 8.10 (s, 1H), 8.33 (s, 1H), 8.44 (s, 1H), 8.48 (d, 1H). MS m/z 628.0 (M + 1). |
| 61 | 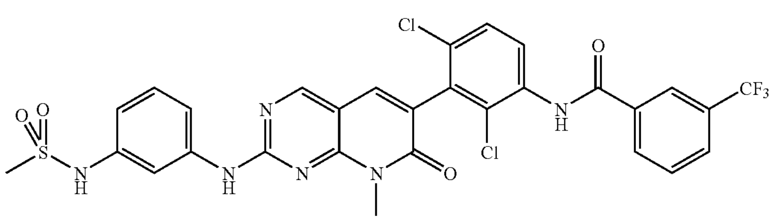 | $^1$H NMR 400 MHz (CD$_3$OD) δ2.91(s, 3H), 3.73 (s, 3H), 6.84(d, 1H), 7.23 (t, 1H), 7.36 (d, 1H), 7.48 (d, 1H), 7.66 (t, 1H), 7.73 (d, 1H), 7.75 (s, 1H), 7.82 (d, 1H), 7.87 (s, 1H), 8.14 (d, 1H), 8.20 (s, 1H), 8.70 (s, 1H). MS m/z 677.0 (M + 1). |
| 62 | 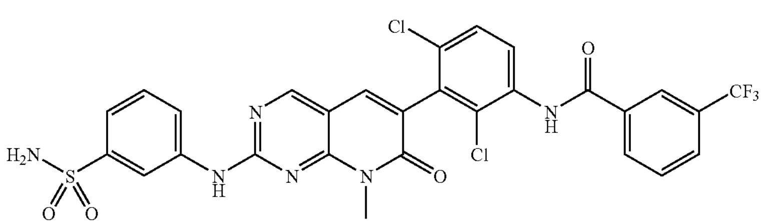 | $^1$H NMR 400 MHz (CDCl$_3$): δ3.59 (s, 3H), 7.24 (d, 2H), 7.34 (d, 1H), 7.43 (t, 1H), 7.45 (s, 1H), 7.58 (d, 2H), 7.69 (d, 1H), 7.91 (d, 1H), 8.00 (s, 1H), 8.36 (bs, 1H), 8.47 (s, 1H). MS m/z 663.0 (M + 1). |

TABLE 1-continued

| Compound Number | Structure | Physical Data $^1$H NMR and MS (m/z) |
|---|---|---|
| 63 | 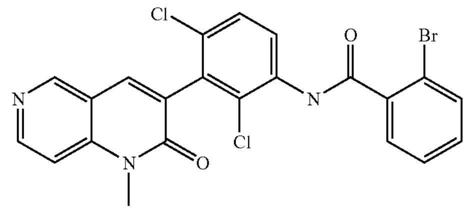 | $^1$H NMR 600 MHz (CD$_3$OD) δ 3.85 (s, 3H), 7.39 (m, 2H), 7.48 (dd, J = 7.43, 7.50 Hz, 1H), 7.61(m, 2H), 7.71 (m, 1H), 7.94 (m, 2H), 8.15 (m, 1H), 8.73 (m, 1H), 9.14 (m, 1H). MS m/z 503.95 (M + 1). |
| 64 | 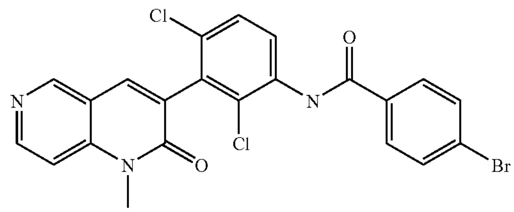 | $^1$H NMR 600 MHz (CD$_3$OD) δ 3.75 (s, 3H), 7.28 (m, 2H), 7.49 (m, 1H), 7.58 (m, 2H), 7.68 (m, 1H), 7.79 (m, 1H), 7.88 (br, 1H), 8.08 (s, 1H), 8.90 (br, 1H). MS m/z 503.95 (M + 1). |
| 65 | 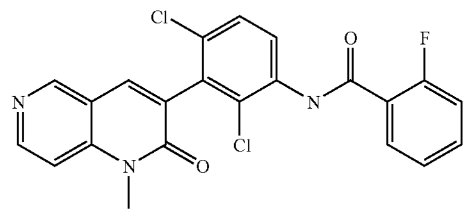 | $^1$H NMR 600 MHz (CD$_3$OD) δ 3.77 (s, 3H), 7.20 (dd, J = 8.36, 11.61 Hz, 1H), 7.28 (m, 1H), 7.52 (m, 2H), 7.88 (m, 2H), 8.10(m, 1H), 8.20 (m, 1H), 8.66(m, 1H), 9.09 (s, 1H). MS m/z 442.00 (M + 1). |
| 66 | 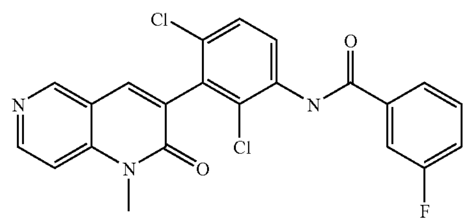 | $^1$H NMR 600 MHz (CD$_3$OD) δ 3.76 (s, 3H), 7.26 (m, 1H), 7.39 (m, 1H), 7.46 (m, 1H), 7.51 (m, 1H), 7.60 (m, 1H), 7.75 (m, 1H), 7.85 (m, 1H), 8.08 (s, 1H), 8.66 (br, 1H), 9.08 (br, 1H). MS m/z 442.00 (M + 1). |
| 67 | 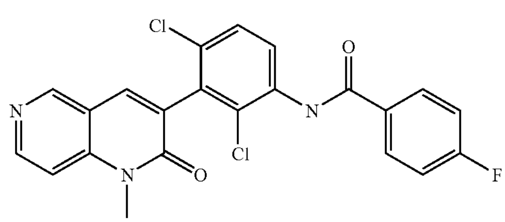 | $^1$H NMR 400 MHz (CD$_3$OD) δ 3.85 (s, 3H), 7.19 (m, 1H), 7.26 (m, 2H), 7.90 (m, 2H), 8.04 (m, 2H), 8.17 (s, 1H), 8.73 (m, br, 1H), 9.13 (s, 1H). MS m/z 442.05 (M + 1). |
| 68 | 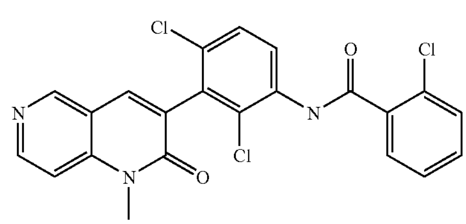 | $^1$H NMR 400 MHz (CD$_3$OD) δ 3.83 (s, 3H), 7.37 (m, 1H), 7.49 (m, 3H), 7.61 (m, 1H), 7.83 (m, 2H), 8.14 (s, 1H), 8.70 (m, 1H), 9.06 (s, 1H). MS m/z 458.00 (M + 1). |
| 69 | 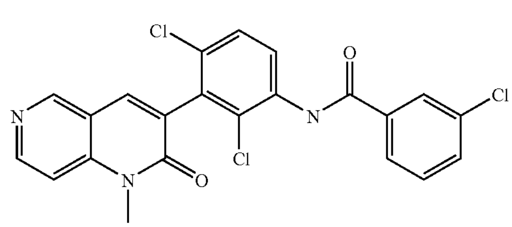 | $^1$H NMR 400 MHz (CD$_3$OD) δ 3.86 (s, 3H), 7.53 (dd, J = 7.86, 7.93 Hz, 1H), 7.62 (m, 2H), 7.89 (m, 2H), 7.99 (m, 2H), 8.20 (s, 1H), 8.76 (br, 1H), 9.20 (s, br, 1H). MS m/z 458.00 (M + 1). |

TABLE 1-continued

| Compound Number | Structure | Physical Data ¹H NMR and MS (m/z) |
|---|---|---|
| 70 | 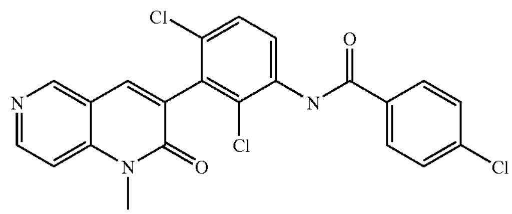 | ¹H NMR 400 MHz (CD$_3$OD) δ 3.86 (s, 3H), 7.55 (m, 2H), 7.60 (d, J = 8.76 Hz, 1H), 7.87 (d, J = 8.76 Hz, 1H), 7.99 (m, 3H), 8.20 (s, 1H), 8.76 (m, 1H), 9.20 (s, 1H). MS m/z 458.00 (M + 1). |
| 71 | 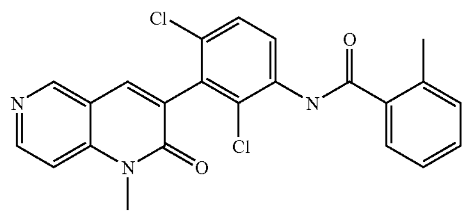 | ¹H NMR 400 MHz (CD$_3$OD) δ 2.51 (s, 3H), 3.86 (s, 3H), 7.30 (m, 2H), 7.40 (m, 1H), 7.60 (m, 2H), 7.95 (m, 2H), 8.19 (s, 1H), 8.74 (m, 1H), 9.16 (m, 1H). MS m/z 438.10 (M + 1). |
| 72 | 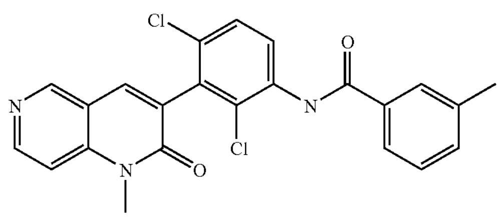 | ¹H NMR 400 MHz (CD$_3$OD) δ 2.43 (s, 3H), 3.86 (s, 3H), 7.40 (m, 2H), 7.60 (d, J = 8.78 Hz, 1H), 7.77 (m, 2H), 7.90 (d, J = 8.76 Hz, 1H), 7.97 (m, 1H), 8.20 (s, 1H), 8.75 (m, 1H), 9.19 (s, 1H). MS m/z 438.10 (M + 1). |
| 73 | 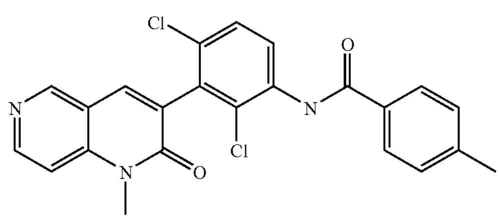 | ¹H NMR 400 MHz (CD$_3$OD) δ 2.43 (s, 3H), 3.85 (s, 3H), 7.35 (m, 2H), 7.59 (d, J = 8.78 Hz, 1H), 7.90 (m, 4H), 8.17 (s, 1H), 8.73 (m, 1H), 9.14 (s, 1H). MS m/z 438.10 (M + 1). |
| 74 | 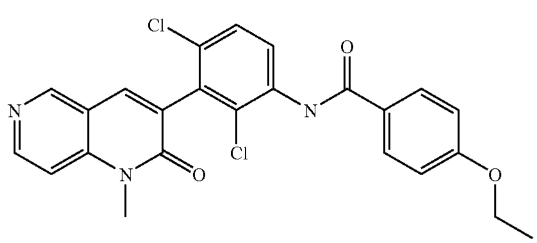 | ¹H NMR 400 MHz (CD$_3$OD) δ 1.43 (t, J = 6.99 Hz, 3H), 3.87 3H), 4.13 (q, J = 6.99 Hz, 2H), 7.04 (m, 2H), 7.59 (d, J = 8.77 Hz, 1H), 7.95 (m, 4H), 8.21 (s, 1H), 8.76 (m, 1H), 9.21 (s, 1H). MS m/z 468.10 (M + 1). |
| 75 | 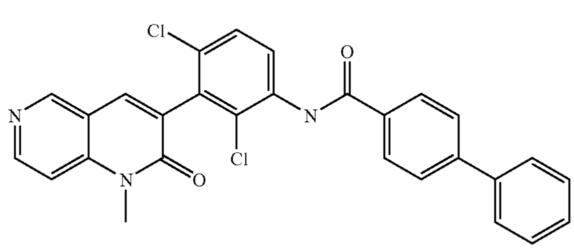 | ¹H NMR 600 MHz (CD$_3$OD) δ 3.77 (s, 3H), 7.30 (m, 1H), 7.38 (m, 2H), 7.52 (d, J = 8.74 Hz, 1H), 7.60 (d, J = 7.57 Hz, 2H), 7.70 (d, J = 8.35 Hz, 2H), 7.84 (m, 2H), 7.98 (d, J = 8.40 Hz, 2H), 8.09 (s, 1H), 8.64 (m, 1H), 9.06 (s, 1H). MS m/z 500.10 (M + 1). |

TABLE 1-continued

| Compound Number | Structure | Physical Data $^1$H NMR and MS (m/z) |
|---|---|---|
| 76 | 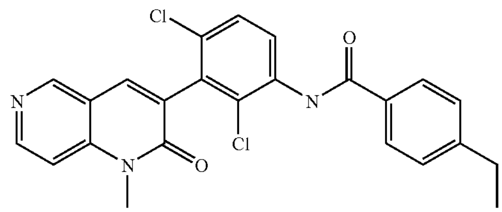 | $^1$H NMR 600 MHz (CD$_3$OD) δ 1.27 (t, J = 7.61 Hz, 3H), 2.74 (q, J = 7.61 Hz, 2H), 3.86 (s, 3H), 7.37 (m, 2H), 7.60 (d, J = 8.77 Hz, 1H), 7.90 (m, 3H), 7.96 (m, 1H), 8.19 (s, 1H), 8.74 (m, 1H), 9.18 (s, 1H). MS m/z 452.10 (M + 1). |
| 77 | 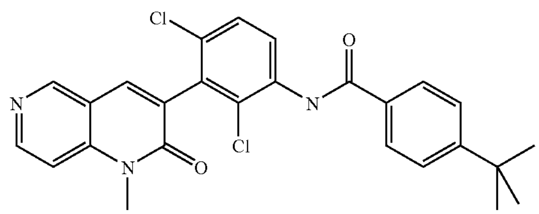 | $^1$H NMR 600 MHz (CD$_3$OD) δ 1.37 (s, 9H), 3.86 (s, 3H), 7.59 (m, 3H), 7.93 (m, 4H), 8.18 (s, 1H), (m, 8.74 1H), 9.16 (s, 1H). MS m/z 480.10 (M + 1). |
| 78 | 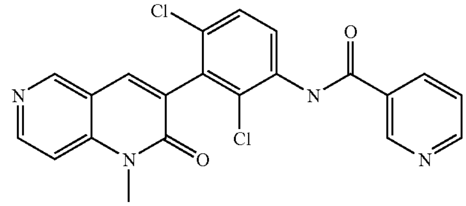 | $^1$H NMR 600 MHz (CD$_3$OD) δ 3.89 (s, 3H), 7.65 (d, J = 8.75 Hz, 1H), 7.78 (br, m, 1H), 7.91 (d, J = 8.75 Hz, 1H), 8.05 (d, J = 6.75 Hz, 1H), 8.25 (s, 1H), 8.58 (br, 1H), 8.81 (m, 2H), 9.23 (m, 2H). MS m/z 425.00 (M + 1). |
| 79 | 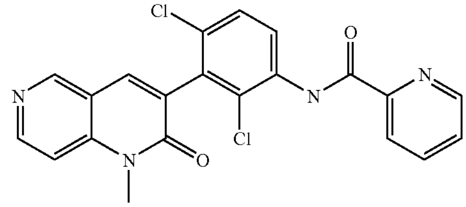 | MS m/z 425.00 (M + 1). |
| 80 | 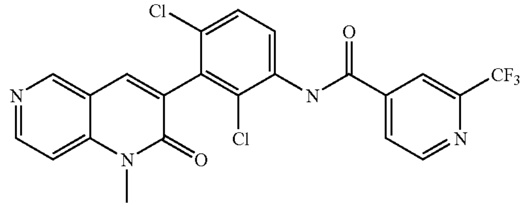 | $^1$H NMR 400 MHz (DMSO) δ 3.57 (s, 3H), 7.46 (d, J = 6.06 Hz, 1H), 7.57 (d, J = 8.67 Hz, 1H), 7.64 (d, J = 8.71 Hz, 1H), 8.01 (d, J = 8.30 Hz, 1H), 8.06 (s, 1H), 8.47 (m, 1H), 8.56 (d, J = 6.02 Hz, 1H), 8.85 (s, 1H), 9.16 (m, 1H), 10.56 (s, 1H). MS m/z 493.00 (M + 1). |
| 81 | 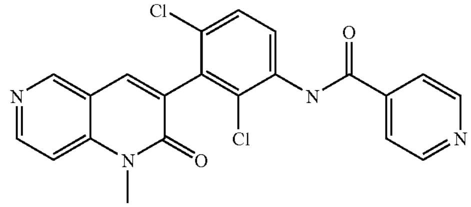 | $^1$H NMR 400 MHz (DMSO) δ 3.75 (s, 3H), 7.71 (d, J = 8.69 Hz, 1H), 7.76 (d, J = 8.72 Hz, 1H), 7.88 (m, 1H), 7.96 (d, J = 4.74 Hz, 1H), 8.30 (s, 1H), 8.84 (m, 3H), 9.20 (s, 1H), 10.62 (s, 1H). MS m/z 425.00 (M + 1). |

TABLE 1-continued

| Compound Number | Structure | Physical Data ¹H NMR and MS (m/z) |
|---|---|---|
| 82 | 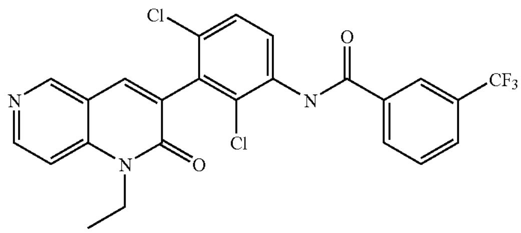 | MS m/z 506.00 (M + 1). |
| 83 | 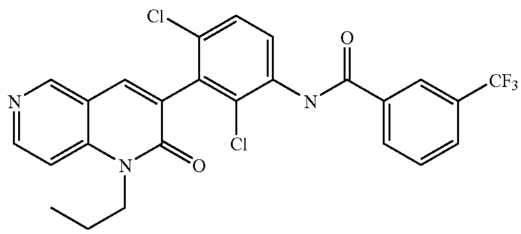 | ¹H NMR 400 MHz (DMSO) δ 0.94 (t, J = 7.40 Hz, 3H), 1.69 (m, 2H), 4.44 (m, 2H), 7.78 (m, 4H), 8.01 (d, J = 6.81 Hz, 1H), 8.22 (m, 2H), 8.30 (d, J = 7.90 Hz, 1H), 8.35 (s, 1H), 10.54 (s, 1H). MS m/z 520.10 (M + 1). |
| 84 | 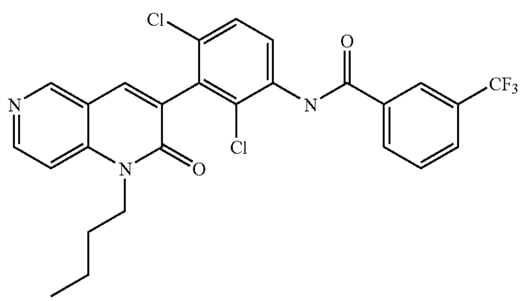 | ¹H NMR 400 MHz (DMSO) δ 1.11 (t, J = 7.33 Hz, 3H), 1.58 (m, 2H), 1.84 (m, 2H), 4.53 (m, 2H), 7.91 (q, J = 8.70 Hz, 2H), 8.01 (m, 2H), 8.21 (m, 1H), 8.44 (m, 1H), 8.50 (d, J = 7.87 Hz, 1H), 8.55 (s, 1H), 8.95 (br, 1H), 9.33 (br, 1H), 10.75 (s, 1H). MS m/z 534.10 (M + 1). |
| 85 | 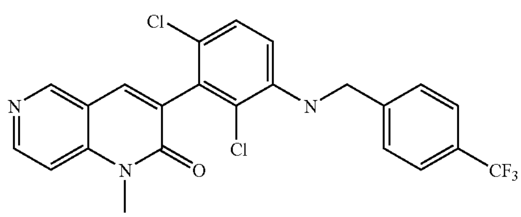 | ¹H NMR 400 MHz (DMSO) δ 3.77 (s, 3H), 5.93 (s, 2H), 6.91 (d, J = 8.81 Hz, 1H), 7.26 (d, J = 8.81 Hz, 1H), 7.75 (d, J = 8.15 Hz, 2H), 7.85 (d, J = 8.26 Hz, 2H), 8.20 (m, 2H), 9.09 (dd, J = 1.56, 7.33 Hz, 1H), 9.55 (s, 1H). MS m/z 478.10 (M + 1). |
| 86 | 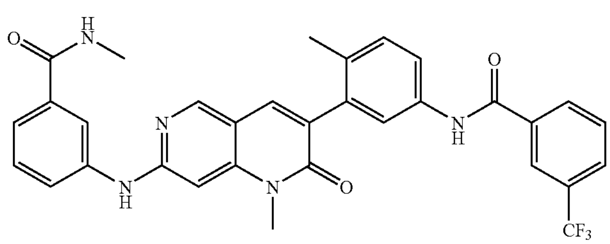 | 586.3 |
| 87 | 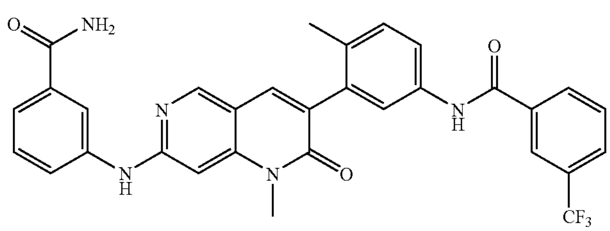 | 572.2 |

TABLE 1-continued

| Compound Number | Structure | Physical Data $^1$H NMR and MS (m/z) |
|---|---|---|
| 88 | 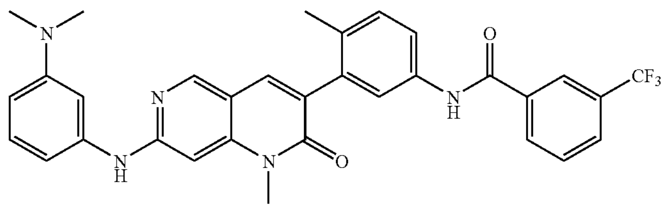 | 572.3 |
| 89 | 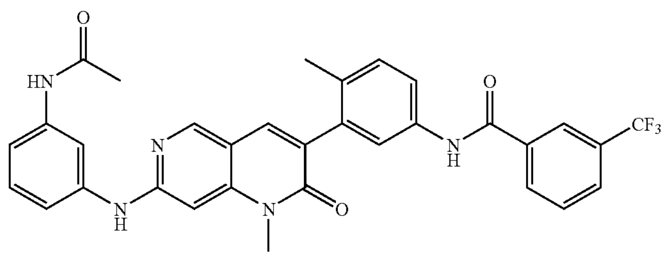 | 586.3 |
| 90 | 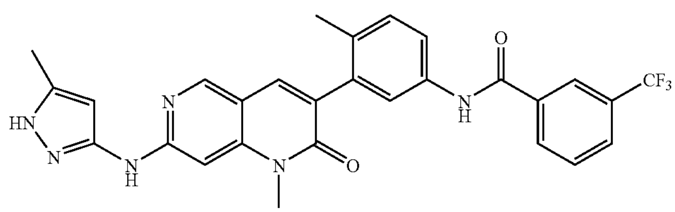 | 533.2 |
| 91 | 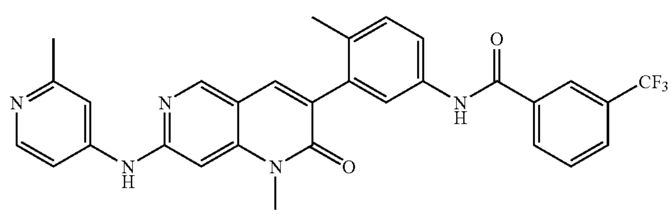 | 544.2 |
| 92 | 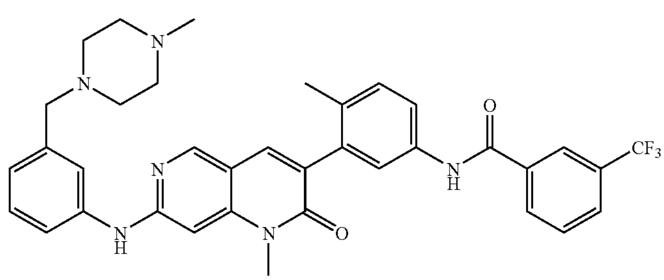 | 641.3 |
| 93 | 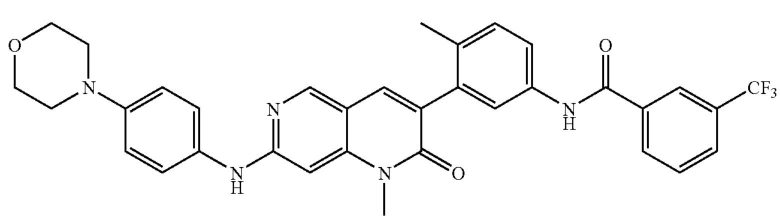 | 614.3 |

TABLE 1-continued

| Compound Number | Structure | Physical Data $^1$H NMR and MS (m/z) |
|---|---|---|
| 94 | 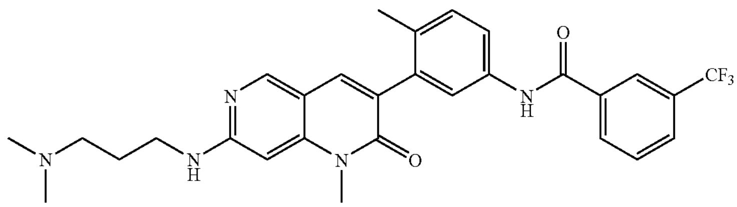 | 538.3 |
| 95 | 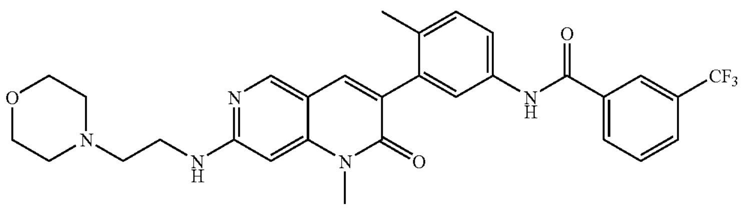 | 566.3 |
| 96 | 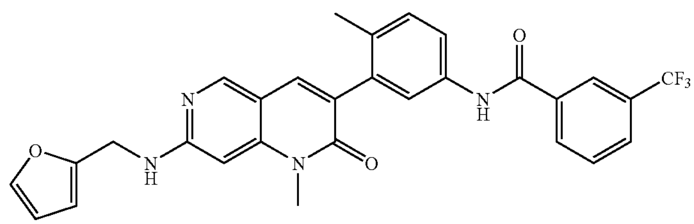 | 533.2 |
| 97 | 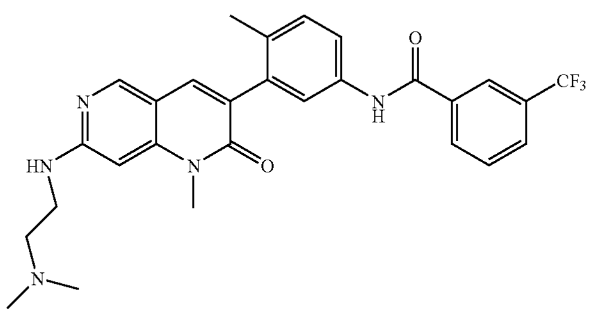 | 524.3 |
| 98 | 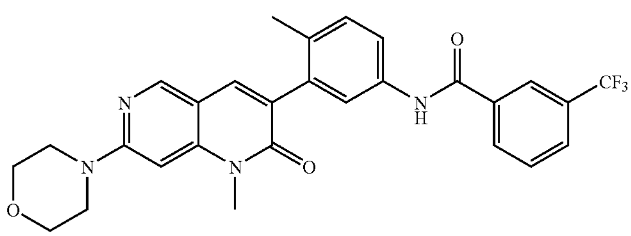 | 523.2 |
| 99 | 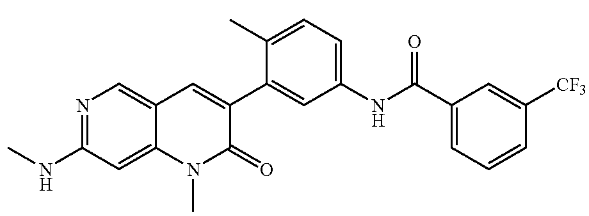 | 467.2 |

TABLE 1-continued

| Compound Number | Structure | Physical Data ¹H NMR and MS (m/z) |
|---|---|---|
| 100 | 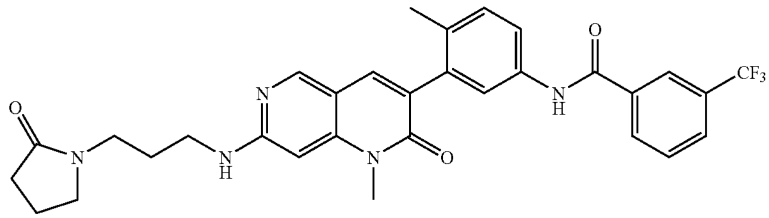 | 578.3 |
| 101 | 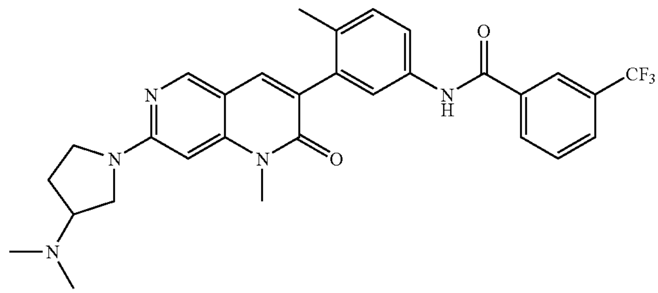 | 550.3 |
| 102 | 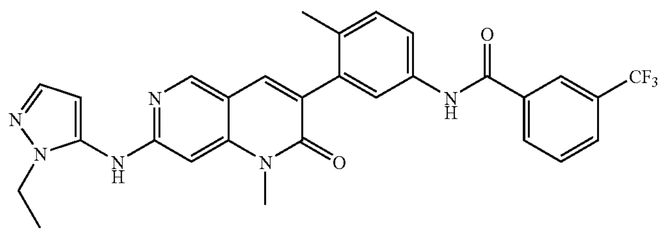 | δ 10.23 (s, 1H), 8.96 (s, 1H), 8.32 (s, 1H), 8.07 (s, 1H), 8.03 (d, J = 8.0 Hz, 1H), 7.74 (d, J = 7.8 Hz, 1H), 7.61 (s, 1H), 7.56 (t, J = 7.7 Hz, 1H), 7.48 (m, 1H), 7.41 (d, J = 2.1 Hz, 1H), 7.21 (d, J = 1.8 Hz, 1H), 7.03 (d, J = 8.4 Hz, 1H), 3.67 (s, 1H), 6.10 (d, J = 1.8 Hz, 1H), 3.83 (q, J = 7.1 Hz, 2H), 3.31 (s, 3H), 1.91 (s, 3H), 1.09 (t, J = 7.1 Hz, 3H);MS (EI) m/z 547.2 (M⁺ + 1). |
| 103 | 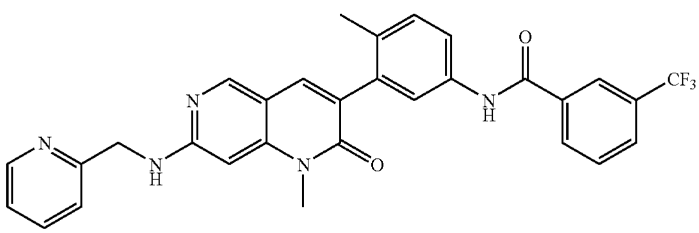 | 544.2 |
| 104 | 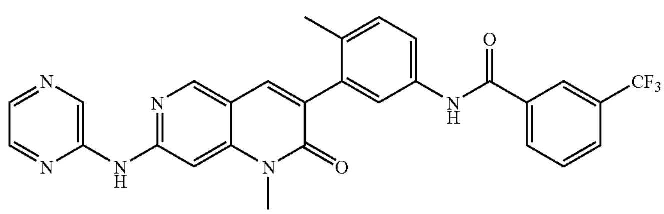 | 531.2 |
| 105 | 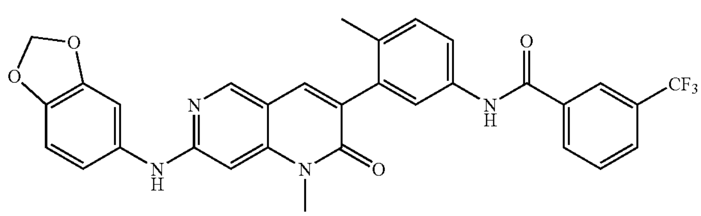 | 573.2 |

TABLE 1-continued

| Compound Number | Structure | Physical Data ¹H NMR and MS (m/z) |
|---|---|---|
| 106 | 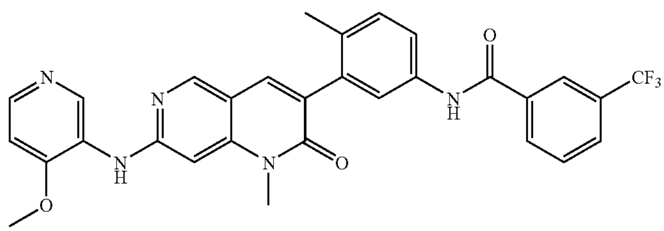 | 560.3 |
| 107 | 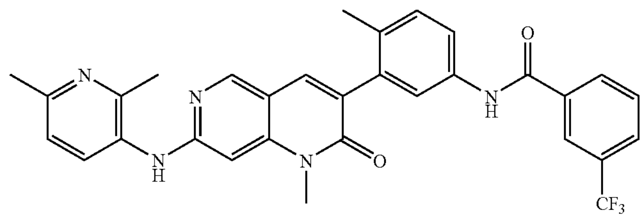 | 558.3 |
| 108 | 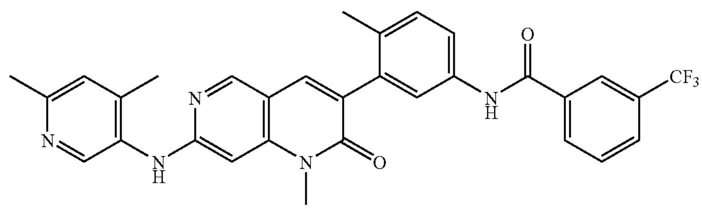 | 558.3 |
| 109 | 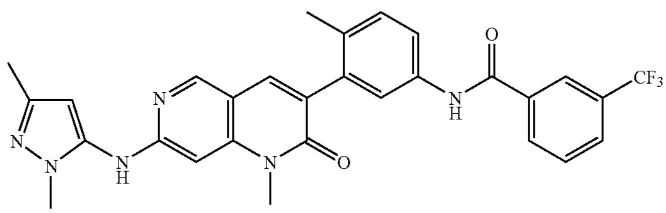 | 547.3 |
| 110 | 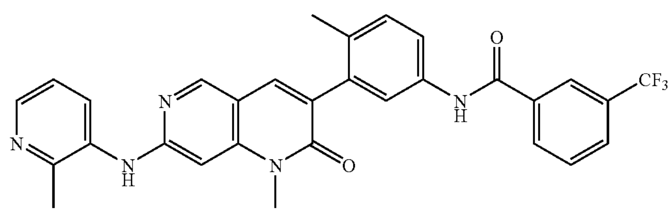 | 544.2 |
| 111 | 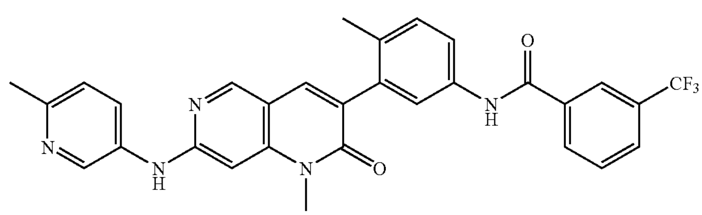 | 544.2 |

TABLE 1-continued

| Compound Number | Structure | Physical Data $^1$H NMR and MS (m/z) |
|---|---|---|
| 112 | 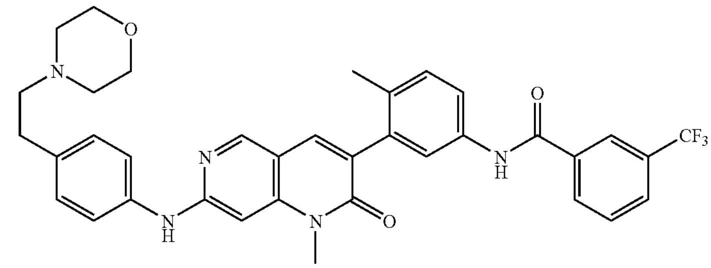 | 642.4 |
| 113 | 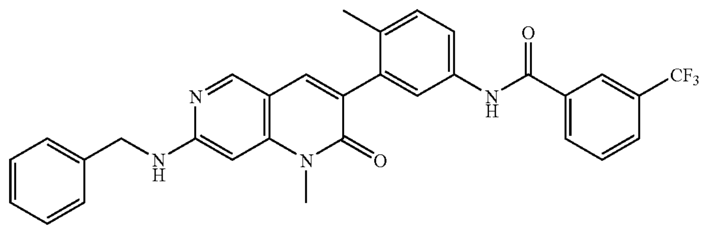 | 543.3 |
| 114 | 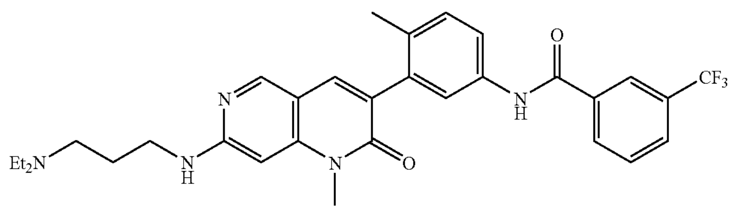 | 566.3 |
| 115 | 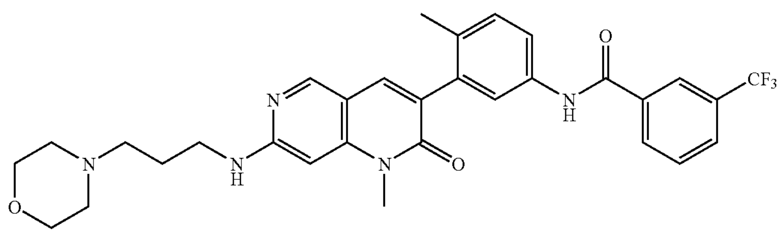 | 580.3 |
| 116 | 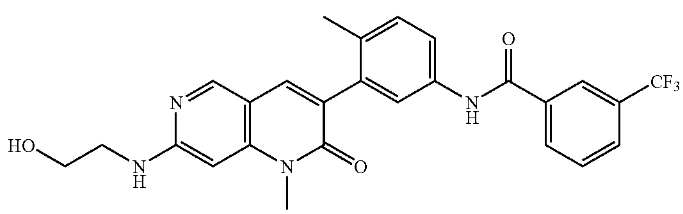 | 497.2 |
| 117 | 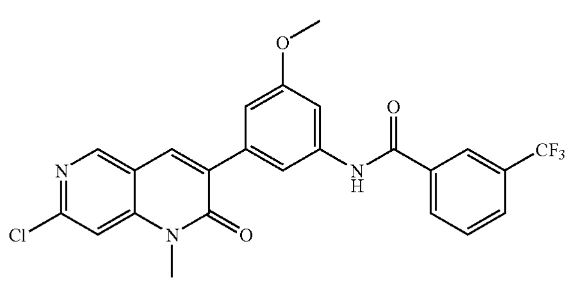 | δ 10.72 (s, 1H), 8.96 (s, 1H), 8.47 (s, 1H), 8.43 (d, J = 7.9 Hz, 1H), 8.38 (s, 1H), 8.13 (d, J = 7.6 Hz, 1H), 7.95 (t, J = 7.8 Hz, 1H), 7.88 (m, 1H), 7.82 (s, 1H), 7.70 (m, 1H), 7.18 (s, 1H), 3.97 (s, 3H), 3.81 (s, 3H); MS (EI) m/z 488.3 (M$^+$ + 1). |

TABLE 1-continued

| Compound Number | Structure | Physical Data $^1$H NMR and MS (m/z) |
|---|---|---|
| 118 | 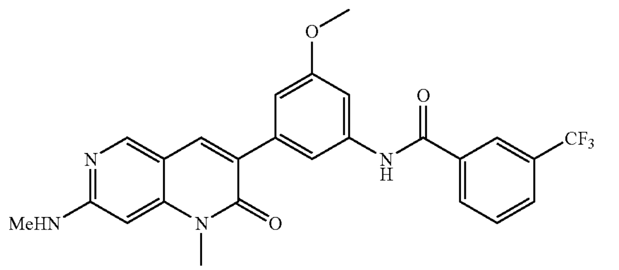 | δ 10.47 (s, 1H), 8.45 (s, 1H), 8.25 (s, 1H), 8.22 (d, J = 8.0 Hz, 1H), 7.94 (s, 1H), 7.92 (d, J = 8.4 Hz, 1H), 7.73 (t, J = 7.8 Hz, 1H), 7.63 (s, 1H), 7.50 (br, 1H), 7.42 (s, 1H), 6.94 (s, 1H), 6.25 (s, 1H), 3.74 (s, 3H), 3.50 (s, 3H), 2.86 (s, 3H); MS (EI) m/z 483.3 (M$^+$ + 1). |
| 119 | 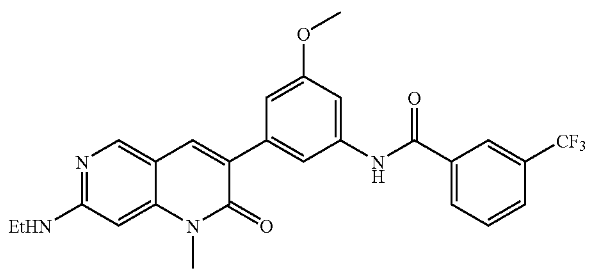 | 497.2 |
| 120 | 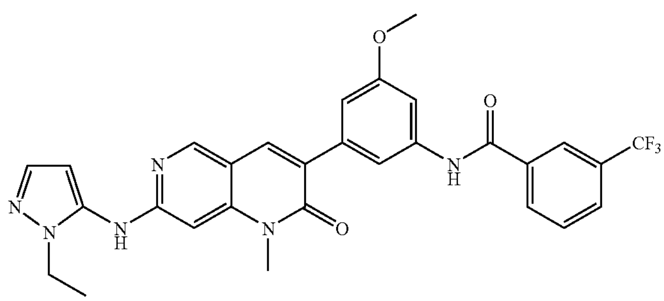 | δ 10.47 (s, 1H), 9.09 (s, 1H), 8.50 (s, 1H), 8.26 (s, 1H), 8.22 (d, J = 8.1 Hz, 1H), 7.99 (s, 1H), 7.92 (d, J = 7.6 Hz, 1H), 7.73 (d, J = 7.9 Hz, 1H), 7.62 (s, 1H), 7.46 (t, J = 2.0 Hz, 1H), 7.37 (t, J = 1.9 Hz, 1H), 6.96 (m, 1H), 6.52 (s, 1H), 6.24 (d, J = 1.8 Hz, 1H), 3.98 (q, J = 7.2 Hz, 2H), 3.75 (s, 3H), 3.48 2H), 3.75 (s, 3H), 1.24 2H), 3.75 (t, J = 7.2 Hz, #<br>3H); MS (EI) m/z 563.4 (M$^+$ + 1). |
| 121 | 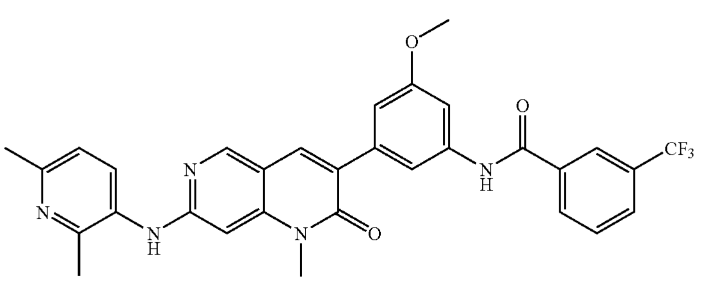 | δ 10.49 (s, 1H), 9.22 (s, 1H), 8.69 (d, J = 8.2 Hz, 1H), 8.54 (s, 1H), 8.26 (s, 1H), 8.22 (d, J = 8.2 Hz, 1H), 8.03 (s, 1H), 7.92 (d, J = 7.6 Hz, 1H), 7.73 (t, J = 7.8 Hz, 1H), 7.66 (s, 1H), 7.58 (d, J = 8.7 Hz, 1H), 7.44 (s, 1H), 6.98 (s, 1H), 6.86 (s, 1H), 3.75 (s, 3H), 3.54 (s, 3H), 2.60 (s, 3H), 2.58 (s, 3H); MS (EI) m/z 574.4 (M$^+$ + 1). |
| 122 | 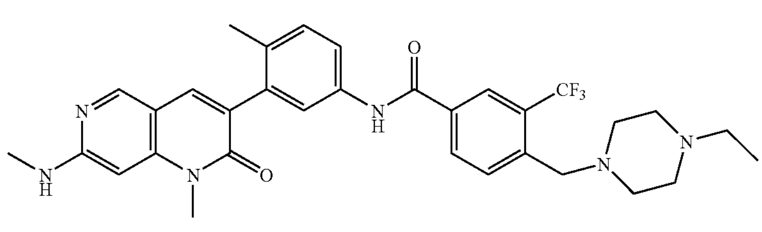 | 593.3 |

TABLE 1-continued
| Compound Number | Structure | Physical Data $^1$H NMR and MS (m/z) |
|---|---|---|
| 123 | 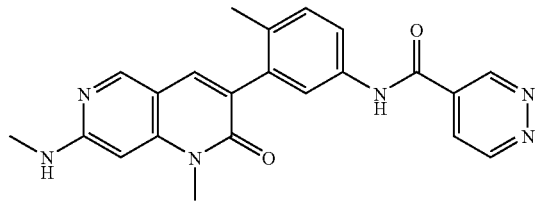 | δ 10.67 (s, 1H), 9.57 (s, 1H), 9.43 (d, J = 5.2 Hz, 1H), 8.46 (s, 1H), 8.04 (dd, J = 2.2, 5.2 Hz, 1H), 7.96 (br, 1H), 7.76 (s, 1H), 7.63 (s, 1H), 7.58 (dd, J = 2.0, 8.3 Hz, 1H), 7.23 (d, J = 8.4 Hz, 1H), 6.41 (s, 1H), 3.50 (s, 3H), 2.90 (s, 3H), 2.07 (s, 3H); MS (EI) m/z 401.4 (M$^+$ + 1). |
| 124 | 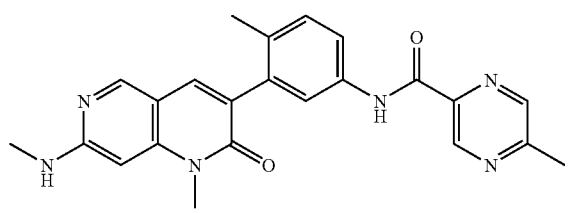 | δ 10.70 (s, 1H), 9.18 (s, 1H), 8.74 (s, 1H), 8.55 (s, 1H), 7.96 (br, 1H), 7.88 (d, J = 1.8 Hz, 1H), 7.86 (s, 1H), 7.80 (dd, J = 1.8, 8.2 Hz, 1H), 7.30 (d, J = 8.3 Hz, 1H), 6.49 (s, 1H), 3.61 (s, 3H), 3.00 (s, 3H), 2.67 (s, 3H), 2.17 (s, 3H); MS (EI) m/z 415.2 (M$^+$ + 1). |
| 125 | 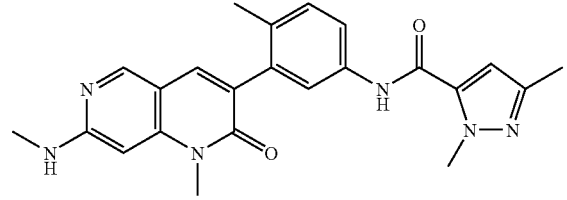 | δ 10.35 (s, 1H), 8.43 (s, 1H), 7.75 (br, 1H), 7.73 (s, 1H), 7.58 (s, 1H), 7.52 (dd, J = 1.4, 8.2 Hz, 1H), 7.45 (s, 1H), 7.20 (d, J = 8.3 Hz, 1H), 6.35 (s, 1H), 4.09 (s, 3H), 3.49 (s, 3H), 2.88 (s, 3H), 2.06 (s, 3H); MS (EI) m/z 471.1 (M$^+$ + 1). |
| 126 | 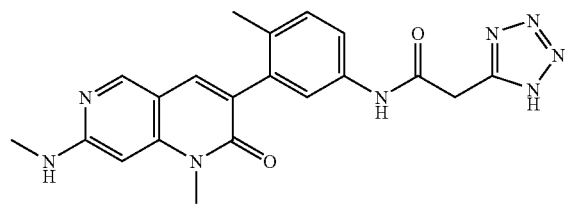 | 405.2 |
| 127 | 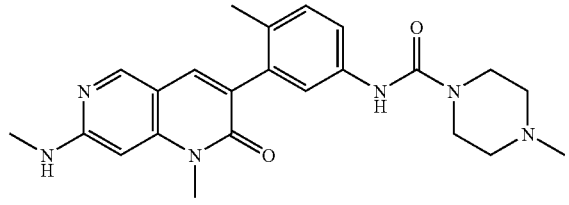 | 421.3 |
| 128 | 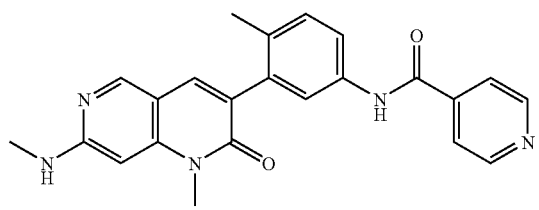 | δ 10.48 (s, 1H), 8.75 (d, J = 5.7 Hz, 2H), 8.45 (s, 1H), 7.95 (br, 1H), 7.83 (d, J = 5.7 Hz, 2H), 7.76 (s, 1H), 7.64 (s, 1H), 7.58 (dd, J = 1.8, 8.2 Hz, 1H), 7.21 (d, J = 8.3 Hz, 1H), 6.41 (s, 1H), 3.50 (s, 3H), 2.90 (s, 3H), 2.07 (s, 3H); MS (EI) m/z 400.4 (M$^+$ + 1). |

TABLE 1-continued

| Compound Number | Structure | Physical Data $^1$H NMR and MS (m/z) |
|---|---|---|
| 129 | 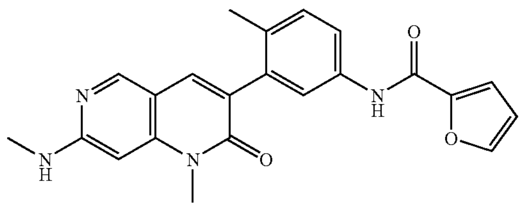 | δ 9.95 (s, 1H), 8.26 (s, 1H), 7.71 (s, 1H), 7.56 (s, 1H), 7.51 (br, 1H), 7.42 (s, 1H), 7.41 (d, J = 7.5 Hz, 1H), 7.10 (d, J = 3.5 Hz, 1H), 7.00 (d, J = 8.2 Hz, 1H), 6.48 (m, 1H), 6.17 (s, 1H), 3.33 (s, 3H), 2.72 (s, 3H), 1.89 (s, 3H); MS (EI) m/z 389.4 (M$^+$ + 1). |
| 130 | 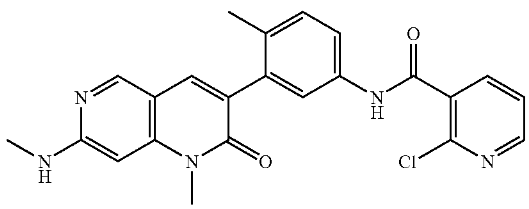 | 434.2 |
| 131 | 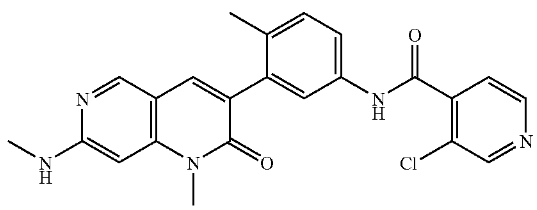 | 434.2 |
| 132 | 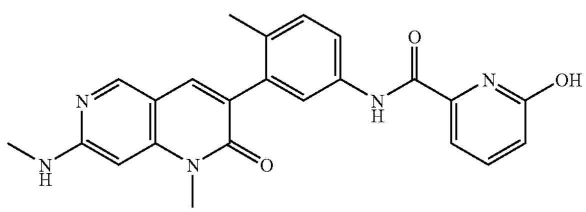 | 416.2 |
| 133 | 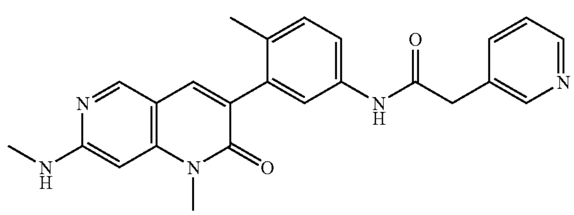 | 414.3 |
| 134 | 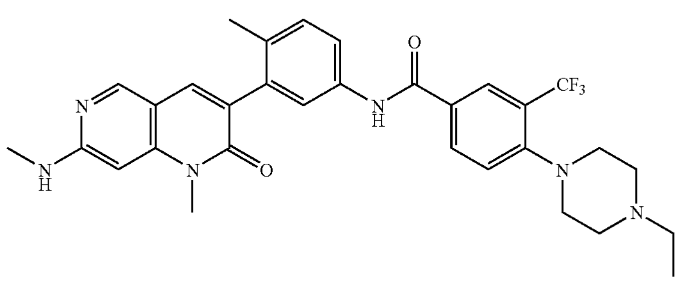 | 579.3 |

TABLE 1-continued

| Compound Number | Structure | Physical Data <sup>1</sup>H NMR and MS (m/z) |
|---|---|---|
| 135 | 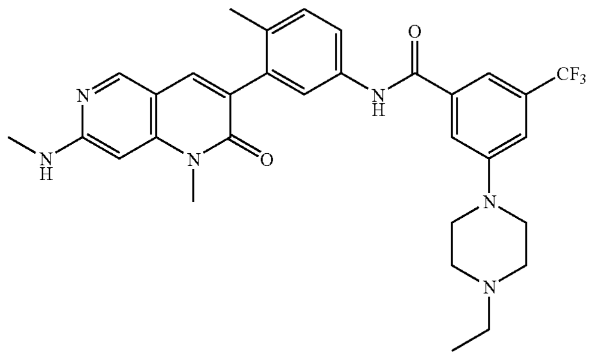 | 579.3 |
| 136 | 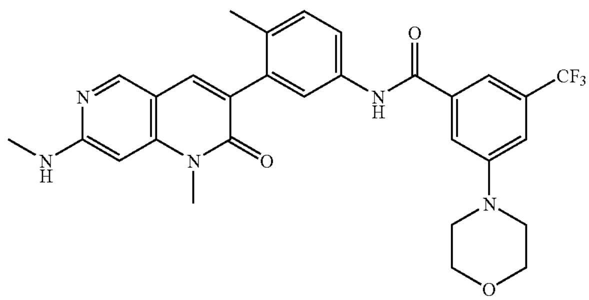 | 552.3 |
| 137 | 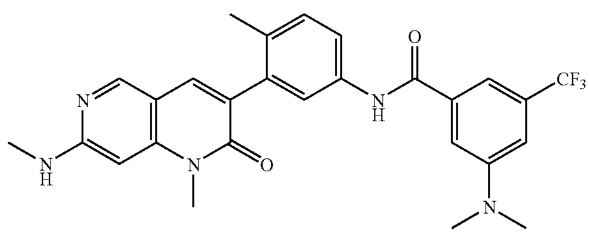 | 510.3 |
| 138 | 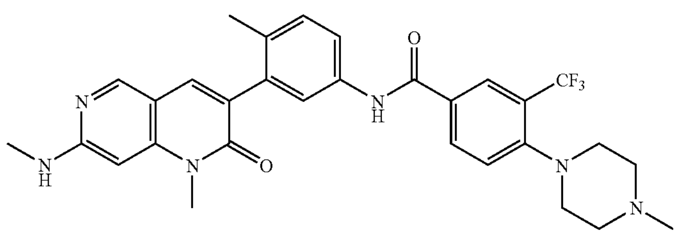 | 565.3 |
| 139 | 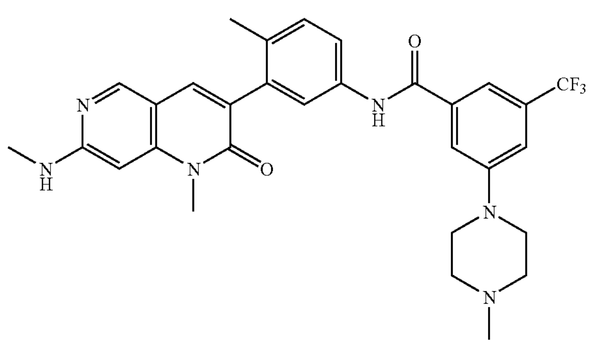 | 565.3 |

Assays

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl. In addition, compounds are assayed to measure their capacity to inhibit b-Raf.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (ST1571 is included as a positive control). The cells are incubated for 72 hours at 37° C., 5% $CO_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acques™ system (Molecular Devices).

Inhibition of Cellular BCR-Abl Dependent Proliferation 32D-p210 cells are plated into 96 well TC plates at a density of 15,000 cells per well. 50 μL of two fold serial dilutions of the test compound ($C_{max}$ is 40 μM) are added to each well (STI571 is included as a positive control). After incubating the cells for 48 hours at 37° C., 5% $CO_2$, 15 μL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at $2.5 \times 10^6$ cells per well in 5 ml of medium and test compound at 1 or 10 μM is added (ST1571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2 \times 10^5$ cells per well in 50 μL of medium. 50 μL of two fold serial dilutions of test compounds ($C_{max}$ is 10 μM) are added to each well (ST1571 is included as a positive control). The cells are incubated for 90 minutes at 37° C., 5% $CO_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to ST1571. The antiproliferative effect of these compounds on the mutant-BCR-Abl expressing cells and on the non transformed cells were tested at 10, 3.3, 1.1 and 0.37 μM as described above (in media lacking IL3). The $IC_{50}$ values of the compounds lacking toxicity on the untransformed cells were determined from the dose response curves obtained as describe above.

FGFR3 (Enzymatic Assay)

Kinase activity assay with purified FGFR3 (Upstate) is carried out in a final volume of 10 μL containing 0.25 μg/mL of enzyme in kinase buffer (30 mM Tris-HCl pH7.5, 15 mM $MgCl_2$, 4.5 mM $MnCl_2$, 15 μM $Na_3VO_4$ and 50 μg/mL BSA), and substrates (5 μg/mL biotin-poly-EY(Glu, Tyr) (CIS-US, Inc.) and 3 μM ATP). Two solutions are made: the first solution of 5 μl contains the FGFR3 enzyme in kinase buffer was first dispensed into 384-format ProxiPlate® (Perkin-Elmer) followed by adding 50 nL of compounds dissolved in DMSO, then 5 μl of second solution contains the substrate (poly-EY) and ATP in kinase buffer was added to each wells. The reactions are incubated at room temperature for one hour, stopped by adding 10 μL of HTRF detection mixture, which contains 30 mM Tris-HCl pH7.5, 0.5 M KF, 50 mM ETDA, 0.2 mg/mL BSA, 15 μg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 μM to 0.28 nM). In this assay, compounds of the invention have an $IC_{50}$ in the range of 10 nM to 2 μM.

FGFR3 (Cellular Assay)

Compounds of the invention are tested for their ability to inhibit transformed Ba/F3-TEL-FGFR3 cells proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 μL culture medium. Compounds of the invention are dissolved and diluted in dimethylsufoxide (DMSO). Twelve points 1:3 serial dilutions are made into DMSO to create concentrations gradient ranging typically from 10 mM to 0.05 μM. Cells are added with 50 nL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

b-Raf

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (10 μl) is added to each well followed by 100 nl or 500 nl of compound. B-Raf is diluted in the assay buffer (1 μl into 25 μl) and 10 μl of diluted b-Raf is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of Attophos AP substrate is added to each well and plates are incubated at room temperature for 15 minutes. Plates are read on Acquest or Analyst GT using a Fluorescence Intensity Nanxin BBT anion (505 dichroic mirror).

Upstate KinaseProfiler™—Radio-Enzymatic Filter Binding Assay

Compounds of the invention are assessed for their ability to inhibit individual members of a panel of kinases (a partial, non-limiting list of kinases includes: Abl, BCR-Abl, CSK, JNK1, JNK2, PDGF-R, p38, p70S6K, TGFβ, SRC, EGFR, c-Kit, trkB, FGFR3, Fes, Lck, Syk, RAF, MKK4, MKK6 and SAPK2μ). The compounds are tested in duplicates at a final concentration of 10 μM following this generic protocol. Note that the kinase buffer composition and the substrates vary for the different kinases included in the "Upstate KinaseProfiler™" panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing $MnCl_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 (or 33.75) mM $MgCl_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an $IC_{50}$ in the range of $1\times10^{-10}$ to $1\times10^{-5}$ M, preferably less than 50 nM for wild type BCR-Abl and G250E, E255V, T315I, F317L and M351T BCR-Abl mutants. For example:

a) N-{3-[7-(6-Methoxy-pyridin-3-ylamino)-1-methyl-2-oxo-1,2-dihydro-[1,6]naphthyridin-3-yl]-4-methyl-phenyl}-3-trifluoromethyl-benzamide (Example 8) has an $IC_{50}$ of <0.5 nM, 43 nM, 48 nM, 122 nM, <0.5 nM and 9 nM for wild type, G250E, E255V, T315I, F317L and M351T Bcr-abl, respectively;

b) N-{3-[7-(6-Methoxy-pyridin-3-ylamino)-1-methyl-2-oxo-1,2-dihydro-[1,6]naphthyridin-3-yl]-4-methyl-phenyl}-3-trifluoromethyl-benzamide (Example 8) has an IC50 of 107 nM and 3 nM for the FGFR3 enzyme and cellular assays respectively, and 500 nM and 17 nM for b-Raf and c-Raf enzyme assays respectively;

Compounds of Formula I, at a concentration of 10 μM, preferably show a percentage inhibition of greater than 50%, preferably greater than about 70%, against Abl, Bcr-abl, Bmx, c-RAF, CSK, Fes, FGFR3, Flt3, GSK3β, IR, JNK1α1, JNK2α2, Lck, MKK4, MKK6, p70S6K, PDGFRα, Rsk1, SAPK2α, SAPK2β, Syk and TrkB kinases. For example:

c) N-{3-[7-(6-Methoxy-pyridin-3-ylamino)-1-methyl-2-oxo-1,2-dihydro-[1,6]naphthyridin-3-yl]-4-methyl-phenyl}-3-trifluoromethyl-benzamide (Example 8), at a concentration of 10 μM, inhibits the following kinases by the percentage shown in brackets (for example, 100% means complete inhibition, 0% means no inhibition): wild-type Abl (100%), Bmx (100%), c-RAF (90%), CSK (100%), FGFR3 (96%), JNK1α1 (89%), JNK2 α2 (99%), Lck (99%), MKK4 (91%), MKK6 (97%), p70S6K (86%), SAPK2α (95%), SAPK2β (98%) and TrkB (97%).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

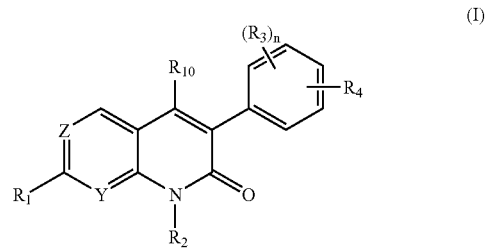

in which:
n is 0, 1 or 2;
Y is selected from —C(H)= and —N=;
Z is selected from —C(H)= and —N=;
$R_1$ is selected from hydrogen, halo and —$R_4$;
$R_2$ is selected from hydrogen and $C_{1-6}$alkyl;
$R_3$ is selected from halo, nitro, $C_{1-6}$alkyl and $C_{1-6}$alkoxy;

$R_4$ is selected from $C_{3-8}$heterocycloalkyl, —$XNR_5R_6$, —$XNR_5C(O)R_6$, —$XC(O)NR_5R_6$ and —$XNR_5S(O)_{0-2}R_6$; wherein X is a bond or $C_{1-4}$alkylene; $R_5$ is selected from hydrogen and $C_{1-6}$alkyl; $R_6$ is selected from $C_{1-6}$alkyl, $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any aryl, heteroaryl, cycloalkyl and heterocycloalkyl of $R_4$ is optionally substituted by 1 to 3 radicals independently selected from halo, hydroxy, nitro, cyano, $C_{1-6}$alkyl optionally substituted with hydroxy, $C_{1-6}$alkoxy, halo-substituted-$C_{1-6}$alkyl, halo-substituted-$C_{1-6}$alkoxy, —$XOXNR_7R_8$, —$XS(O)_{0-2}R_7$, —$XS(O)_{0-2}NR_7R_8$, —$XOR_7$, —$XC(O)NR_7R_8$, —$XNR_7R_8$, —$XNR_7S(O)_{0-2}R_7$ and —$XR_9$; wherein X is a bond or $C_{1-4}$alkylene; $R_7$ and $R_8$ are independently selected from hydrogen and $C_{1-6}$alkyl; $R_9$ is selected from $C_{6-10}$aryl, $C_{5-10}$heteroaryl $C_{3-12}$cycloalkyl and $C_{3-8}$heterocycloalkyl; wherein any aryl, heteroaryl, cycloalkyl or heterocycloalkyl of $R_9$ is optionally substituted with 1 to 3 $C_{1-6}$alkyl radicals;

$R_{10}$ is selected from hydrogen, halo and $C_{1-6}$alkyl; and the pharmaceutically acceptable salts, solvates and isomers thereof.

2. The compound of claim 1 in which:

n is 0, 1 or 2;

Y is selected from —C(H)= and —N=;

Z is selected from —C(H)= and —N=;

$R_1$ is selected from hydrogen, halo and —$R_4$;

$R_2$ is selected from hydrogen and $C_{1-6}$alkyl;

$R_3$ is selected from halo, $C_{1-6}$alkyl and $C_{1-6}$alkoxy;

$R_4$ is selected from $C_{3-8}$heterocycloalkyl, —$XNR_5R_6$, —$XNR_5C(O)R_6$ and —$XNR_5S(O)_{0-2}R_6$; wherein X is a bond or $C_{1-4}$alkylene; $R_5$ is selected from hydrogen and $C_{1-6}$alkyl; $R_6$ is selected from $C_{1-6}$alkyl, $C_{6-10}$aryl-$C_{0-4}$alkyl, $C_{3-8}$heterocycloalkyl-$C_{0-4}$alkyl, $C_{5-10}$heteroaryl-$C_{0-4}$alkyl and $C_{3-12}$cycloalkyl-$C_{0-4}$alkyl; wherein any aryl, heteroaryl and cycloalkyl of $R_4$ is optionally substituted by 1 to 3 radicals independently selected from halo, hydroxy, nitro, $C_{1-6}$alkyl optionally substituted with hydroxy, $C_{1-6}$alkoxy, halo-substituted-$C_{1-6}$alkyl, halo-substituted-$C_{1-6}$alkoxy, —$XS(O)_{0-2}R_7$, —$XOXNR_7R_8$, —$XS(O)_{0-2}NR_7R_8$, —$XOR_7$, —$XC(O)NR_7R_8$, —$XNR_7R_8$ and —$XR_9$; wherein X is a bond or $C_{1-4}$alkylene; $R_7$ and $R_8$ are independently selected from hydrogen and $C_{1-6}$alkyl; $R_9$ is selected from $C_{5-10}$heteroaryl and $C_{3-8}$heterocycloalkyl; wherein any heteroaryl or heterocycloalkyl of $R_9$ is optionally substituted with 1 to 3 $C_{1-6}$alkyl radicals; and $R_{10}$ is hydrogen.

3. The compound of claim 2 in which $R_1$ is selected from hydrogen, halo, pyrrolidinyl and —$NHR_6$; wherein $R_6$ is selected from hydrogen, methyl, ethyl, diethyl-amino-propyl, morpholino-ethyl, hydroxy-ethyl, benzo[1,3]dioxolyl, pyrazolyl, pyridinyl, pyrazinyl, pyridinyl-methyl, 2-(2-oxo-pyrrolidin-1-yl)-ethyl and phenyl; wherein said pyrrolidinyl, pyridinyl, pyrazolyl, pyrazinyl, pyridinyl-methyl, 2-(2-oxo-pyrrolidin-1-yl)-ethyl or phenyl is optionally substituted by 1 to 2 radicals independently selected from amino, methoxy, dimethylamino, dimethylamino-methyl, dimethylamino-ethyl, dimethylamino-propyl, dimethylamino-ethoxy, methyl-sulfanyl, hydroxy, methylsulfonyl, hydroxymethyl, 1-hydroxy-ethyl, methane-sulfonyl-amino, morpholino, morpholino-ethyl, furanyl-methyl, 4-methyl-piperazin-1-yl, 4-methyl-piperazin-1-ylmethyl, benzyl, methyl-aminocarbonyl, methyl-carbonyl-amino, methyl-pyrazolyl, aminocarbonyl and amino-sulfonyl.

4. The compound of claim 2 in which $R_4$ is selected from —$NHC(O)R_6$ and —$NHS(O)2R_6$; wherein $R_6$ is selected from methyl, isobutyl, tert-butyl, cyclohexyl, furanyl, pynolyl, phenyl, pyridinyl, pyridazinyl, pyrazinyl, pyrazolyl, tetrazolyl-methyl and benzyl; wherein said cyclohexyl, furanyl, pynolyl, phenyl, pyridinyl, pyridazinyl, pyrazinyl, pyrazolyl, tetrazolyl-methyl or benzyl of $R_6$ is optionally substituted by 1 to 3 radicals selected from 4-methyl-piperazin-1-ylmethyl, 4-methyl-piperazin-1-yl, 4-ethyl-piperazin-1-ylmethyl, 4-ethyl-piperazin-1-yl, phenyl, ethyl, trifluoromethyl, morpholino, dimethylamino, halo, nitro, trifluoromethoxy, 1-methyl-pymol-2-yl, 4-methyl-imidazol-1-yl, 4-methyl-piperazin-1-yl, 4-methyl-piperazin-1-ylmethyl, isobutyl and tert-butyl.

5. A pharmaceutical composition comprising a therapeutically effective amount of a compound of claim 1 in combination with a pharmaceutically acceptable excipient.

* * * * *